US009308275B2

(12) United States Patent
Epshtein

(10) Patent No.: US 9,308,275 B2
(45) Date of Patent: *Apr. 12, 2016

(54) METHOD OF INCREASING THE EFFECT OF AN ACTIVATED-POTENTIATED FORM OF AN ANTIBODY

(75) Inventor: Oleg Iliich Epshtein, Moscow (RU)

(73) Assignee: Oleg Iliich Epshtein, Moscow (RU)

( * ) Notice: Subject to any disclaimer, the term of this patent is extended or adjusted under 35 U.S.C. 154(b) by 182 days.

This patent is subject to a terminal disclaimer.

(21) Appl. No.: 13/135,901

(22) Filed: Jul. 15, 2011

(65) Prior Publication Data
US 2014/0079696 A1   Mar. 20, 2014

(30) Foreign Application Priority Data

| Jul. 15, 2010 | (RU) | 2010129290 |
| Jul. 15, 2010 | (RU) | 2010129291 |
| Jul. 15, 2010 | (RU) | 2010129292 |
| Jul. 15, 2010 | (RU) | 2010129294 |
| Jul. 15, 2010 | (RU) | 2010129295 |
| Jul. 15, 2010 | (RU) | 2010129298 |
| Jul. 21, 2010 | (RU) | 2010130348 |
| Jul. 21, 2010 | (RU) | 2010130353 |
| Jul. 21, 2010 | (RU) | 2010130355 |
| Jul. 21, 2010 | (RU) | 2010130356 |
| Jul. 21, 2010 | (RU) | 2010130358 |
| Mar. 17, 2011 | (RU) | 2011110106 |
| Jul. 1, 2011 | (RU) | 2011127051 |
| Jul. 1, 2011 | (RU) | 2011127052 |
| Jul. 1, 2011 | (RU) | 2011127053 |
| Jul. 1, 2011 | (RU) | 2011127055 |
| Jul. 1, 2011 | (RU) | 2011127058 |
| Jul. 1, 2011 | (RU) | 2011127059 |

(51) Int. Cl.
| A61K 47/48 | (2006.01) |
| A61K 41/00 | (2006.01) |
| C07K 16/18 | (2006.01) |
| C07K 16/28 | (2006.01) |
| C07K 16/40 | (2006.01) |
| A61K 39/395 | (2006.01) |
| A61K 39/00 | (2006.01) |

(52) U.S. Cl.
CPC ....... A61K 47/48276 (2013.01); A61K 39/3955 (2013.01); A61K 41/0004 (2013.01); C07K 16/18 (2013.01); C07K 16/2869 (2013.01); C07K 16/40 (2013.01); A61K 2039/507 (2013.01)

(58) Field of Classification Search
CPC ................................................. A61K 41/0004
See application file for complete search history.

(56) References Cited

U.S. PATENT DOCUMENTS

| 3,032,584 A | 5/1962 | Bergel et al. |
| 3,134,718 A | 5/1964 | Nobile |
| 3,901,967 A | 8/1975 | Cohen et al. |
| 4,292,324 A | 9/1981 | Jonsson et al. |
| 4,311,897 A | 1/1982 | Yerushalmy |
| 4,839,341 A | 6/1989 | Massey et al. |
| 4,963,367 A | 10/1990 | Ecanow |
| 4,987,127 A | 1/1991 | Sirany |
| 5,629,286 A | 5/1997 | Brewitt |
| 5,683,712 A | 11/1997 | Cavazza |
| 5,698,195 A | 12/1997 | Le et al. |
| 5,733,572 A | 3/1998 | Unger et al. |
| 5,741,488 A | 4/1998 | Feldman et al. |
| 5,846,514 A | 12/1998 | Foster et al. |
| 5,849,528 A | 12/1998 | Hillman et al. |
| 5,879,677 A | 3/1999 | del Zoppo |
| 5,895,783 A | 4/1999 | Garfield et al. |
| 6,136,309 A | 10/2000 | Novick et al. |
| 6,143,722 A | 11/2000 | Melin et al. |
| 6,150,500 A | 11/2000 | Salerno |
| 6,326,360 B1 | 12/2001 | Kanazawa et al. |
| 6,750,197 B1 | 6/2004 | Salerno |
| 6,933,272 B1 | 8/2005 | Helmerhorst et al. |
| 7,229,648 B2 | 6/2007 | Dreyer |
| 7,396,659 B2 | 7/2008 | Singh |
| 7,572,441 B2 | 8/2009 | Epshtein et al. |
| 7,582,294 B2 | 9/2009 | Epshtein et al. |
| 7,700,096 B2 | 4/2010 | Epshtein et al. |
| 7,815,904 B2 | 10/2010 | Epshtein et al. |

(Continued)

FOREIGN PATENT DOCUMENTS

| CN | 101495143 A | 7/2009 |
| DE | WO/99/21582 A2 | 10/1998 |

(Continued)

OTHER PUBLICATIONS

Declaration filed on Sep. 29, 2008 in U.S. Appl. No. 10/522,653, 2 pages.*

(Continued)

*Primary Examiner* — Ilia Ouspenski
(74) *Attorney, Agent, or Firm* — Pergament & Cepeda LLP; Milagros A. Cepeda; Edward D. Pergament

(57) ABSTRACT

The preset invention provides a method of increasing the effect of an activated-potentiated form of an antibody to an endogenous biological molecule by combining said endogenous biological molecule with an activated-potentiated form of an antibody to endothelial NO-synthase.

The present invention also provides a pharmaceutical composition comprising a) an activated-potentiated form of an antibody to an endogenous biological molecule, and b) an activated-potentiated form of an antibody to NO synthase.

8 Claims, 4 Drawing Sheets

(56) References Cited

U.S. PATENT DOCUMENTS

| | | | |
|---|---|---|---|
| 7,923,009 B2 | 4/2011 | Epshtein et al. | |
| 8,066,992 B2 | 11/2011 | Epshtein | |
| 8,168,182 B2 | 5/2012 | Epshtein | |
| 8,178,498 B1 | 5/2012 | Ephstein | |
| 8,241,625 B2 | 8/2012 | Epshtein et al. | |
| 8,524,229 B2 | 9/2013 | Epshtein et al. | |
| 8,535,664 B2 | 9/2013 | Epshtein et al. | |
| 8,617,555 B2* | 12/2013 | Epshtein | 424/158.1 |
| 8,637,030 B2 | 1/2014 | Epshtein | |
| 8,637,034 B2 | 1/2014 | Epshtein | |
| 2002/0001588 A1 | 1/2002 | Sinha | |
| 2003/0099636 A1 | 5/2003 | Epshtein et al. | |
| 2005/0266007 A1 | 12/2005 | Epshtein et al. | |
| 2006/0024307 A1 | 2/2006 | Epshteni et al. | |
| 2006/0153845 A1 | 7/2006 | Epshtein et al. | |
| 2006/0165697 A1 | 7/2006 | Epshtein et al. | |
| 2007/0123518 A1 | 5/2007 | Epshtein et al. | |
| 2007/0141058 A1 | 6/2007 | Iliich et al. | |
| 2007/0224187 A1 | 9/2007 | Epshtein et al. | |
| 2008/0019982 A1 | 1/2008 | Iliich et al. | |
| 2008/0025985 A1 | 1/2008 | Iliich et al. | |
| 2008/0050360 A1 | 2/2008 | Iliich et al. | |
| 2008/0050392 A1 | 2/2008 | Iliich et al. | |
| 2008/0131440 A1 | 6/2008 | Epshtein et al. | |
| 2009/0148521 A1 | 6/2009 | Epstehin | |
| 2009/0285781 A1 | 11/2009 | Epshtein | |
| 2009/0285829 A1 | 11/2009 | Epshtein | |
| 2010/0166762 A1 | 7/2010 | Epshtein | |
| 2010/0203059 A1 | 8/2010 | Epshtein | |
| 2010/0221258 A1 | 9/2010 | Epshtein | |
| 2010/0239569 A1 | 9/2010 | Epshtein | |
| 2011/0008452 A1 | 1/2011 | Epshtein et al. | |
| 2011/0086037 A1 | 4/2011 | Iliich et al. | |
| 2011/0230401 A1 | 9/2011 | Artymiuk et al. | |
| 2012/0045445 A1 | 2/2012 | Epshtein | |
| 2012/0225074 A1 | 9/2012 | Epshtein et al. | |
| 2012/0251584 A1 | 10/2012 | Epshtein et al. | |
| 2012/0258146 A1* | 10/2012 | Epshtein | 424/400 |
| 2012/0263725 A1 | 10/2012 | Epshtein et al. | |
| 2012/0263726 A1 | 10/2012 | Epshtein et al. | |
| 2012/0294899 A1 | 11/2012 | Epshtein et al. | |
| 2012/0321672 A1* | 12/2012 | Epshtein | 424/400 |
| 2013/0017202 A1 | 1/2013 | Epshtein et al. | |
| 2013/0045237 A1 | 2/2013 | Epshtein et al. | |
| 2013/0058981 A1* | 3/2013 | Epshtein | 424/400 |
| 2013/0058982 A1* | 3/2013 | Epshtein | 424/400 |
| 2013/0064860 A1* | 3/2013 | Epshtein | 424/400 |
| 2013/0171161 A1 | 7/2013 | Epshtein et al. | |
| 2013/0189707 A1 | 7/2013 | Sergeeva et al. | |
| 2013/0224219 A1 | 8/2013 | Epshtein et al. | |
| 2013/0302312 A1 | 11/2013 | Epshtein et al. | |
| 2013/0303735 A1 | 11/2013 | Epshtein et al. | |
| 2013/0315964 A1 | 11/2013 | Epshtein et al. | |
| 2013/0336985 A1 | 12/2013 | Epshtein et al. | |
| 2014/0010819 A1 | 1/2014 | Epshtein et al. | |
| 2014/0056923 A9 | 2/2014 | Epshtein et al. | |
| 2014/0112934 A1 | 4/2014 | Epshtein | |

FOREIGN PATENT DOCUMENTS

| | | |
|---|---|---|
| EP | 0652014 A1 | 5/1995 |
| EP | 0687466 A1 | 12/1995 |
| EP | 0884042 A1 | 12/1998 |
| EP | 1295606 A1 | 3/2003 |
| EP | 1466622 A1 | 10/2004 |
| EP | 1547611 A1 | 6/2005 |
| EP | 1547612 A1 | 6/2005 |
| EP | 2036574 A1 | 3/2009 |
| JP | 2007-518692 A | 7/2007 |
| JP | 2008-511593 A | 4/2008 |
| JP | 2009-532463 A | 9/2009 |
| JP | 2009-539827 A | 11/2009 |
| JP | 2009-542800 A | 12/2009 |
| JP | 2013-538791 A | 4/2014 |
| RU | 1836083 A3 | 8/1993 |
| RU | 2007989 C1 | 2/1994 |
| RU | 2033784 C1 | 4/1995 |
| RU | 0884042 A1 | 8/1997 |
| RU | 2104032 C1 | 2/1998 |
| RU | WO/98/14161 A1 | 4/1998 |
| RU | WO/98/14162 A1 | 4/1998 |
| RU | WO/98/14166 A1 | 4/1998 |
| RU | WO/98/33493 A1 | 8/1998 |
| RU | WO/98/35680 A1 | 8/1998 |
| RU | 2122858 C1 | 12/1998 |
| RU | 2137483 C1 | 9/1999 |
| RU | 2144370 C1 | 1/2000 |
| RU | 2156621 C1 | 9/2000 |
| RU | WO/01/05371 A1 | 1/2001 |
| RU | 2169000 C2 | 6/2001 |
| RU | 2177795 C1 | 1/2002 |
| RU | 2187334 C2 | 8/2002 |
| RU | 2192882 C1 | 11/2002 |
| RU | 2199345 C1 | 2/2003 |
| RU | WO/03/037372 A1 | 5/2003 |
| RU | WO/03/055518 A1 | 7/2003 |
| RU | WO/03/055519 A1 | 7/2003 |
| RU | WO/03/077946 A1 | 9/2003 |
| RU | WO/2004/012765 A1 | 2/2004 |
| SU | 1331508 A1 | 8/1987 |
| SU | 1730144 A1 | 4/1992 |
| WO | 9412213 A1 | 6/1994 |
| WO | 9422846 A1 | 10/1994 |
| WO | 9520978 A1 | 8/1995 |
| WO | 9728776 A1 | 8/1997 |

OTHER PUBLICATIONS

Shang A et al: "Are the clinical effects of homoeopathy placebo effects? Comparative study of placebo-controlled trials of homoeopathy and allopathy", The Lancet, Lancet Limited. London, GB, vol. 366, No. 9487, Aug. 27, 2005, pp. 726-732.

E. S. Zhavbert et al: "Evaluation of the Efficiency and Safety of Combined Treatment with Impaza and Nitrates in CHD Patients with Erectile Dysfunction", Bulletin of Experimental Biology and Medicine, vol. 148, No. 2, Aug. 1, 2009, pp. 325-327.

Jonas Wayne B et al: "A critical overview of homeopathy", Annals of Internal Medicine, New York, NY; US, US,vol. 138, No. 5, Mar. 4, 2003 pp. 393-399.

Vickers A J: "Clinical Trials of Homeopathy and Placebo: Analysis of a Scientific Debate", Journal of Alternative and Complementary Medicine, Mary Ann Liebert, New York, NY, US,vol. 6, No. 1, Feb. 1, 2000, pp. 49-56.

Written Opinion of the International Searching Authority for corresponding International Patent Application No. PCT/182011/002350.

Notification of Transmittal of International Search Report and Written Opinion dated Feb. 9, 2012 for corresponding International Patent Application No. PCT/182011/002350.

International Search Report dated Feb. 9, 2012 for corresponding International Patent Application No. PCT/182011/002350.

Markel, et al., "Hypotensive Activity of Ultralow Doses of Antibodies to Factors Involved in the Regulation of Vascular Tone", Bulletin of Experimental Biology and Medicine, 2003, Supplement 1, p. 57-59.

Pavlov, "Effect of Antibodies Against S-100B Antigen in Ultralow Doses on Sucrose Consumption During Learning", Bulletin of Experimental Biology and Medicine, 2007, vol. 143, No. 6, p. 686-688.

Borovskaya, et al., "Effects of Ultralow Doses of Antibodies to Prostate-Specific Antigen on Morphological and Functional State of Rat Prostate", Bulletin of Experimental Biology and Medicine, 2003, vol. 135, supplement 7, p. 91-93.

Spasov, et al., "Study of Antidiabetic Activity of a New Ultralow-Dose Antibody Preparation on the Model of Streptozotocin Diabetes in Rats", Bulletin of Experimental Biology and Medicine, Jul. 2007, vol. 144, p. 46-48.

Office Action dated Nov. 5, 2013, issued by the Swedish Patent Office for corresponding Swedish Patent Application No. 1350184-6 based on International Patent Application No. PCT/IB2011/002350.

(56) References Cited

OTHER PUBLICATIONS

Borovskaya, et al., Impact of Antibodies to Endothelial No-Synthase on Sexual Behavior of Male Rats in Conditions of Seasonal Suppression of Reproductive Function, Scientific—Research Institute of pharmacology (2001) (Translation).
International Search Report from International Application No. PCT/RU01/00239, filed Jun. 19, 2001, mailed on Sep. 20, 2001.
International Search Report from International Application No. PCT/RU02/00367, filed Aug. 2, 2002, mailed on Dec. 19, 2002.
International Search Report from International Application No. PCT/RU02/00369, filed Aug. 2, 2002, mailed on Dec. 26, 2002.
International Search Report from International Application No. PCT/RU02/00365, filed Aug. 2, 2002, mailed on Dec. 5, 2002.
International Search Report from International Application No. PCT/RU2006/000237,filed May 16, 2006, mailed on Nov. 23, 2006.
Beregovoy et al., On Influence of Various Dilutions of Monoclonal Antibodies 5F5-B6 on the Formation of Long-Term Post-Tetanic Potentiation in Survived Hippocampal Slices, Bull of Siberian Branch of RAMS No. 1 (91), 1999.
Pavlov et al., "Behavioral Effects of Potentiated Morphine Forms," Bull of Siberian Branch of RAMS No. 1 (91), 1999.
Zapara et al., "Potentiated Morphine Effect on the Electric Properties of Isolated Neurons." Bull of Siberian Branch of RAMS, No. 1 (91), (1999).
Frimel, G., ed., "immunological methods," Medicina publishing House, 1987, pp. 9-33.
Skurkovich, et al. Multiple Sclerosis Randomized study of antibodies to IFN-γ and TNF-α in secondary progressive multiple sclerosis, 7:277-284, (2001).
Alexandrova et al., "An Experience of Application of Potentiated Compounds for Jugulation of Alcohol Abstinent Syndrome and Opiate Abstinent Syndrome," Bull of Siberian Branch of RAMS, No. 1 (91), 1999.
Maini, R. N. et al., "Anti-Cytokine Therapy for Rheumatoid Arthritis," Annu. Rev. Med. 51:207-229 (2000).
White et al., "Radioimmunotherapy of relapsed B-cell lymphoma with yttrium 90 anti-idiotype monoclonal antibodies," Blood, vol. 87: 3640-3649 (1996).
Linde et al., "Are the clinical effects of homoeopathy placebo effects? A meta-analysis of placebo-controlled trials," Lancet, vol. 350: 836-43 (1997).
International Search Report from International Application No. PCT/RU02/00368, filed Aug. 2, 2002, mailed on Dec. 5, 2002.
Marsden, P.A., et al., "Molecular cloning and characterization of human endothelial nitric oxide synthase," FEBS Lett., vol. 307, No. 3, pp. 287-293, 1992.
Register of Pharmaceuticals in Russia, Encyclopedia of Pharmaceuticals (in Russian), Moscow, 2001, pp. 788-789.
Schwabe, W., "German Homeopathic Pharmacopia (Homoepathisches Arznibuch)," Stuttgart, Translatiaon of the 5th Supplement (1991) to the 1978 edition.
Vyazov, O.L., Laboratory Methods of Studies in Non-Infection Immunology (in Russian), Moscow, Meditsina, 1968.
Janeway, et al., Immunology, 1997, 3rd edition, Garland Publishing Inc., pp. 3:1-3:11.
Davenas, et al., Nature, 1998, 333: 816-818.
Epshtein, et al., May 1999, Bulletin of Experimental Biology and Medicine, vol. 5: 493-495.
Goldacre (2007) Lancet 370: 1672-1673.
Grigorieve M. Yu. et al., "K probleme ispolzovaniya potentsirovannykh ogrannykh preparatov," Lechebno-Profilaticheskaja Rabota Dlya Meditsinskikh Organizatsu Ugolnoj Promyshlennosti, vyp. 8, 1989, ids. Tshiehi ugol (Moscow), pp. 163-165.
International Search Report from International Application No. PCT/RU04/000374, filed Sep. 27, 2004, mailed on Feb. 10, 2005.
International Search Report from International Application No. PCT/RU97/00026, filed Feb. 10, 1997, mailed on Apr. 8, 1997.
Ivanushkin, a. Ja., "Gomeopatiya i sovremennaya meditsina," Vestnik Akademi Meditsinkskikh Nauk SSSR, 4, 1988, izd. "Meditsina" (Moscow), pp. 76-82.
Vasiliev, Yu. V. et al., "Gomepatiya: vozrozhdenie tradisionnjoy meditsinskoj shkoly," Vestnik Rossijkoj Akademi Nauk, 10, 1992, izd. "Nauka" (Moscow), pp. 145-148.
Jeger, J., Ed., "Clinical Immunology and Allergology" (Russian Translation), Meditsina, Moscow, 2000, pp. 358-359.
Kuznik, R.I. et al., "Cytomedines and their Role in Regulation of Physiological Functions," Uspekhi Sovremennoi Biologil, 1995, vol. 115, No. 3, pp. 353-367.
Nickeleit, et al., 2007, Kid, Int. vol. 71: 7-11.
Register of Pharmaceuticals of Russia, Encyclopedia of Pharmaceuticals (in Russian), Moscow, 2000, pp. 358-359.
Schwab, V., Homepathic Pharmaceuticals Agents. A manual on description and preparation, Moscow, 1967, pp. 12-38.
Shang, et al., 2005, Lancet vol. 366: 726-32.
Stefani, D. V. et al., "Immunopatologiya detskogo vozrasta," Moscow, Meditsina, 1996, pp. 28, 29, 358-359.
Thomson Innovation English Abstract for Foreign Patent No. RU 2199345C1.
Bohan N. A., et al., "Comparative Effectiveness of "Proprotien-100" Alcoholism in Treatment of Patients in Phase Formation Therapeutic Remission", Bulletin Experimental Biology and Medicine, 2003, pp. 91-96.
Machine Translation of Bohan N. A., et al., "Comparative Effectiveness of "Proprotien-100" Alcoholism in Treatment of Patients in Phase Formation Therapeutic Remission", Bulletin Experimental Biology and Medicine, 2003, pp. 91-96.
Castagne, et al., "Antibodies to S100 Proteins Have Anxiolytic-Like Activity at Ultra-Low Doses in the Adult Rat", Journal of Pharmacy and Pharmacology, 2008, pp. 309-316.
Epshtein, et al., "Effects of Potentiated Antibodies to Brain Specific Protein S100 on the Dynamics of Long-Term Potentiation in Hippocampal Slices", Bulletin of Experimental Biology and Medicine, 1999, p. 286-289.
Epshtein, et al., "Effects of Homeopathic Doses of Antibodies to S100 Antigen on Electric Characteristics of Neuronal Membranes", Bulletin of Experimental Biology and Medicine, 1999, p. 423-424.
Epshtein, "Regulatory Activity of Ultralow Doses", Bulletin of Experimental Biology and Medicine, 2003, Supplement 1, p. 8-13.
Epshtein, et al., "Improvement of Memory by Means of Ultra-Low Doses of Antibodies to S-100B Antigen", eCAM, 2006, vol. 3, Issue 4, p. 541-545.
Faraci, "Proctecting the Brain With eNOS; Run for Your Life", Circulation Research, 2006, vol. 99, pp. 1029-1030.
Habib, et al., "Nitric Oxide Measurement From Blood to Lungs, Is There a Link?", Pak J Physiol, 2007, vol. 3, Issue 1, p. 45-49.
Laffly, et al., "Monoclonal and Recombinant Antibodies, 30 Years After . . . ", Human Antibodies, 2005, vol. 14, pp. 33-55.
Rohde, et al., "S100A1: A Multifaceted Therapeutic Target in Cardiovascular Disease", J. of Cardiovasc. Trans. Res., 2010, vol. 3, p. 525-537.
Voronina T. A., et al., "Study of the Effects of Preparation Containing Ultralow Doses of Antibodies to S-100 Protein in Experimental Hemorrhagic Stroke", Bulletin of Experimental Biology and Medicine, 2009, vol. 148, Suppl. 1, pp. 530-532.
Voronina T. A., et al., "Effect of Ultralow Doses of Antibodies to S-100 Protein in Animals with Impaired Cognitive Function and Disturbed Emotional and Neurological Status under Conditions of Experimental Alzheimer Disease", Bulletin of Experimental Biology and Medicine, 2009, vol. 148, Suppl. 1, pp. 533-535.
Yardan, et al., "Usefulness of S100B Protein in Neurological Disorders", J Pak Med Assoc., Mar. 2011, vol. 61, No. 3, pp. 276-281.
Notice of Reasons for Rejection issued on Apr. 7, 2015 by the Japanese Patent Office for corresponding Japanese Patent Application No. JP 2013-519175.
Eastern Medicine, 2007, vol. 23, No. 2, pp. 21-33, Medical Online.
Gudkov A.V., "Experience of Long-Term Afala Treatment in Benign Prostatic Hyperplasia", Bulletin of Experimental Biology and Medicine, 2009, pp. 308-311, vol. 148, No. 2, Springer Science and Media, Inc.
Markel A. L., et al., "Effect of Impaza on Cardiovascular System", Bulletin of Experimental Biology and Medicine, 2009, pp. 518-519, vol. 148, Springer Science & Business Media, Inc.

(56) References Cited

OTHER PUBLICATIONS

Petrov, V.I., et al., "Pharmacodynamics of Kardos Administered as Monotherapy and in Combination with Hypothiazide and Enalapril in Grade I-II Arterial Hypertension", Bulletin of Experimental Biology and Medicine, 2009, pp. 335-336, vol. 148, Springer Science & Business Media, Inc.

Chitaley, K., et al., "Diabetes, Obesity and Erectile Dysfunction: Field Overview and Research Priorities" The Journal of Urology, 2009, pp. 45-50, vol. 182, www.jurology.com.

View of NCT00678704 on Jun. 20, 2009, ClinicalTrials.gov archive [online], Jun. 20, 2009, [searched on Mar. 23, 2015] URL<https://clinicaltrials.gov/archive/NCT00678704/2009_06_20>.

Result of Consultation issued by the European Patent Office on Apr. 29, 2015 for corresponding European Patent Application No. 11 775 838.3.

Summons to attend oral proceedings pursuant to Rule 115(1) EPC issued by the European Patent Office on May 7, 2015 for corresponding European Patent Application No. 11 775 838.3.

Beregovoi N A et al: "Effect of antibodies to morphine in ultralow doses on induction of long-term potentiation in hippocampal slices from rats with chronic morphine dependence.", Bulletin of Experimental Biology and Medicine Jan. 2003, vol. 135 Suppl 7, Jan. 2003, pp. 26-28.

Bokhan N A et al: "Comparative efficiency of Proproten-100 during the therapy of patients with alcoholism in the stage of therapeutic remission.", Bulletin of Experimental Biology and Medicine Jan. 2003, vol. 135 Suppl 7, Jan. 2003, pp. 171-175, ISSN: 1573-8221.

Dugina J L et al: "A randomized, open-label, comparative, 6-month trial of oral ultra-low doses of antibodies to tumor necrosis factor-alpha and diclofenac in rheumatoid arthritis.", International Journal of Tissue Reactions 2005, vol. 27, No. 1, 2005, pp. 15-21, ISSN: 0250-0868.

Epstein O I et al: "Dose-dependent effects and specificity of action of antibodies to endogenous regulators in ultralow doses.", Bulletin of Experimental Biology and Medicine May 2004, vol. 137, No. 5, May 2004, pp. 460-462, ISSN: 0007-4888.

Krylova S G et al: "Antiulcer activity of ultralow doses of antibodies to histamine under experimental conditions.", Bulletin of Experimental Biology and Medicine Jan. 2003, vol. 135 Suppl 7, Jan. 2003, pp. 80-82, ISSN: 1573-8221.

Voronova O L et al: "Cytogenetic effects of antibodies to gamma-interferon in ultralow doses.", Bulletin of Experimental Biology and Medicine Jan. 2003, vol. 135 Suppl 7, Jan. 2003, pp. 65-66, ISSN: 1573-8221.

Romanova G A et al: "Neuroprotective activity of proproten in rats with experimental local photothrombosis of the prefrontal cortex.", Bulletin of Experimental Biology and Medicine Apr. 2005, vol. 139, No. 4, Apr. 2005, pp. 404-407, ISSN: 0007-4888.

Third Office Action issued by the State Intellectual Property Office (SIPO) of P.R. China on Jun. 16, 2015 for corresponding Chinese Patent Application No. 201180044332.4.

Haidong, L., et al. "Mandatory standards for production safety in construction projects and practices for preventing accidents in construction sites", 2002, p. 1110, Jilin Science and Technology Press Co., Ltd.

Hanzhang D., et al., "College students self health care", 2001, p. 77, Zhejiang University Press Co., Ltd.

\* cited by examiner

* differences rare statistically significant in reference to control (distilled water), p<0.05

SEQUENCE LISTING

<160> NUMBER OF SEQ ID NOS: 8

<210> SEQ ID NO 1
<211> LENGTH: 1205
<212> TYPE: PRT
<213> ORGANISM: Bos taurus
<220> FEATURE:
<221> NAME/KEY: SOURCE
<222> LOCATION: 1..1205
<223> OTHER INFORMATION: /mol_type="protein"
      /organism="Bos taurus"

<400> SEQUENCE: 1

Met Gly Asn Leu Lys Ser Val Gly Gln Glu Pro Gly Pro Pro Cys Gly
1               5                   10                  15

Leu Gly Leu Gly Leu Gly Leu Gly Leu Cys Gly Lys Gln Gly Pro Ala
            20                  25                  30

Ser Pro Ala Pro Glu Pro Ser Arg Ala Pro Ala Pro Ala Thr Pro His
        35                  40                  45

Ala Pro Asp His Ser Pro Ala Pro Asn Ser Pro Thr Leu Thr Arg Pro
    50                  55                  60

Pro Glu Gly Pro Lys Phe Pro Arg Val Lys Asn Trp Glu Leu Gly Ser
65                  70                  75                  80

Ile Thr Tyr Asp Thr Leu Cys Ala Gln Ser Gln Gln Asp Gly Pro Cys
                85                  90                  95

Thr Pro Arg Cys Cys Leu Gly Ser Leu Val Leu Pro Arg Lys Leu Gln
            100                 105                 110

Thr Arg Pro Ser Pro Gly Pro Pro Ala Glu Gln Leu Leu Ser Gln
            115                 120                 125

Ala Arg Asp Phe Ile Asn Gln Tyr Tyr Ser Ser Ile Lys Arg Ser Gly
        130                 135                 140

Ser Gln Ala His Glu Glu Arg Leu Gln Glu Val Glu Ala Glu Val Ala
145                 150                 155                 160

Ser Thr Gly Thr Tyr His Leu Arg Glu Ser Glu Leu Val Phe Gly Ala
                165                 170                 175

Lys Gln Ala Trp Arg Asn Ala Pro Arg Cys Val Gly Arg Ile Gln Trp
            180                 185                 190

Gly Lys Leu Gln Val Phe Asp Ala Arg Asp Cys Ser Ser Ala Gln Glu
        195                 200                 205

Met Phe Thr Tyr Ile Cys Asn His Ile Lys Tyr Ala Thr Asn Arg Gly
    210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                245                 250                 255

Arg Gln Gln Asp Gly Ser Val Arg Gly Asp Pro Ala Asn Val Glu Ile
            260                 265                 270

Thr Glu Leu Cys Ile Gln His Gly Trp Thr Pro Gly Asn Gly Arg Phe
        275                 280                 285

Asp Val Leu Pro Leu Leu Leu Gln Ala Pro Asp Glu Ala Pro Glu Leu
    290                 295                 300

Phe Val Leu Pro Pro Glu Leu Val Leu Glu Val Pro Leu Glu His Pro
305                 310                 315                 320

Thr Leu Glu Trp Phe Ala Ala Leu Gly Leu Arg Trp Tyr Ala Leu Pro
                325                 330                 335

Ala Val Ser Asn Met Leu Leu Glu Ile Gly Gly Leu Glu Phe Ser Ala

```
            340             345             350
Ala Pro Phe Ser Gly Trp Tyr Met Ser Thr Glu Ile Gly Thr Arg Asn
            355             360             365

Leu Cys Asp Pro His Arg Tyr Asn Ile Leu Glu Asp Val Ala Val Cys
370             375             380

Met Asp Leu Asp Thr Arg Thr Thr Ser Ser Leu Trp Lys Asp Lys Ala
385             390             395             400

Ala Val Glu Ile Asn Leu Ala Val Leu His Ser Phe Gln Leu Ala Lys
            405             410             415

Val Thr Ile Val Asp His His Ala Ala Thr Val Ser Phe Met Lys His
            420             425             430

Leu Asp Asn Glu Gln Lys Ala Arg Gly Gly Cys Pro Ala Asp Trp Ala
            435             440             445

Trp Ile Val Pro Pro Ile Ser Gly Ser Leu Thr Pro Val Phe His Gln
            450             455             460

Glu Met Val Asn Tyr Ile Leu Ser Pro Ala Phe Arg Tyr Gln Pro Asp
465             470             475             480

Pro Trp Lys Gly Ser Ala Thr Lys Gly Ala Gly Ile Thr Arg Lys Lys
            485             490             495

Thr Phe Lys Glu Val Ala Asn Ala Val Lys Ile Ser Ala Ser Leu Met
            500             505             510

Gly Thr Leu Met Ala Lys Arg Val Lys Ala Thr Ile Leu Tyr Ala Ser
            515             520             525

Glu Thr Gly Arg Ala Gln Ser Tyr Ala Gln Gln Leu Gly Arg Leu Phe
            530             535             540

Arg Lys Ala Phe Asp Pro Arg Val Leu Cys Met Asp Glu Tyr Asp Val
545             550             555             560

Val Ser Leu Glu His Glu Ala Leu Val Leu Val Val Thr Ser Thr Phe
            565             570             575

Gly Asn Gly Asp Pro Pro Glu Asn Gly Glu Ser Phe Ala Ala Ala Leu
            580             585             590

Met Glu Met Ser Gly Pro Tyr Asn Ser Ser Pro Arg Pro Glu Gln His
            595             600             605

Lys Ser Tyr Lys Ile Arg Phe Asn Ser Val Ser Cys Ser Asp Pro Leu
610             615             620

Val Ser Ser Trp Arg Arg Lys Arg Lys Glu Ser Ser Asn Thr Asp Ser
625             630             635             640

Ala Gly Ala Leu Gly Thr Leu Arg Phe Cys Val Phe Gly Leu Gly Ser
            645             650             655

Arg Ala Tyr Pro His Phe Cys Ala Phe Ala Arg Ala Val Asp Thr Arg
            660             665             670

Leu Glu Glu Leu Gly Gly Glu Arg Leu Leu Gln Leu Gly Gln Gly Asp
            675             680             685

Glu Leu Cys Gly Gln Glu Glu Ala Phe Arg Gly Trp Ala Lys Ala Ala
            690             695             700

Phe Gln Ala Ser Cys Glu Thr Phe Cys Val Gly Glu Glu Ala Lys Ala
705             710             715             720

Ala Ala Gln Asp Ile Phe Ser Pro Lys Arg Ser Trp Lys Arg Gln Arg
            725             730             735

Tyr Arg Leu Ser Thr Gln Ala Glu Gly Leu Gln Leu Leu Pro Gly Leu
            740             745             750

Ile His Val His Arg Arg Lys Met Phe Gln Ala Thr Val Leu Ser Val
            755             760             765
```

```
Glu Asn Leu Gln Ser Ser Lys Ser Thr Arg Ala Thr Ile Leu Val Arg
    770                 775                 780

Leu Asp Thr Ala Gly Gln Glu Gly Leu Gln Tyr Gln Pro Gly Asp His
785                 790                 795                 800

Ile Gly Ile Cys Pro Pro Asn Arg Pro Gly Leu Val Glu Ala Leu Leu
                805                 810                 815

Ser Arg Val Glu Asp Pro Pro Pro Thr Glu Ser Val Ala Val Glu
                820                 825                 830

Gln Leu Glu Lys Gly Ser Pro Gly Gly Pro Pro Ser Trp Val Arg
            835                 840                 845

Asp Pro Arg Leu Pro Pro Cys Thr Leu Arg Gln Ala Leu Thr Phe Phe
850                 855                 860

Leu Asp Ile Thr Ser Pro Pro Ser Pro Arg Leu Leu Arg Leu Leu Ser
865                 870                 875                 880

Thr Leu Ala Glu Glu Pro Ser Glu Gln Gln Glu Leu Glu Thr Leu Ser
                885                 890                 895

Gln Asp Pro Arg Arg Tyr Glu Glu Trp Lys Trp Phe Arg Cys Pro Thr
                900                 905                 910

Leu Leu Glu Val Leu Gln Phe Pro Ser Val Ala Leu Pro Ala Pro
            915                 920                 925

Leu Leu Leu Thr Gln Leu Pro Leu Leu Gln Pro Arg Tyr Tyr Ser Val
            930                 935                 940

Ser Ser Ala Pro Asn Ala His Pro Gly Glu Val His Leu Thr Val Ala
945                 950                 955                 960

Val Leu Ala Tyr Arg Thr Gln Asp Gly Leu Gly Pro Leu His Tyr Gly
                965                 970                 975

Val Cys Ser Thr Trp Leu Ser Gln Leu Lys Thr Gly Asp Pro Val Pro
                980                 985                 990

Cys Phe Ile Arg Gly Ala Pro Ser Phe Arg Leu Pro Pro Asp Pro Tyr
            995                 1000                1005

Val Pro Cys Ile Leu Val Gly Pro Gly Thr Gly Ile Ala Pro Phe Arg
    1010                1015                1020

Gly Phe Trp Gln Glu Arg Leu His Asp Ile Glu Ser Lys Gly Leu Gln
1025                1030                1035                1040

Pro Ala Pro Met Thr Leu Val Phe Gly Cys Arg Cys Ser Gln Leu Asp
                1045                1050                1055

His Leu Tyr Arg Asp Glu Val Gln Asp Ala Gln Glu Arg Gly Val Phe
                1060                1065                1070

Gly Arg Val Leu Thr Ala Phe Ser Arg Glu Pro Asp Ser Pro Lys Thr
            1075                1080                1085

Tyr Val Gln Asp Ile Leu Arg Thr Glu Leu Ala Ala Glu Val His Arg
    1090                1095                1100

Val Leu Cys Leu Glu Arg Gly His Met Phe Val Cys Gly Asp Val Thr
1105                1110                1115                1120

Met Ala Thr Ser Val Leu Gln Thr Val Gln Arg Ile Leu Ala Thr Glu
                1125                1130                1135

Gly Asp Met Glu Leu Asp Glu Ala Gly Asp Val Ile Gly Val Leu Arg
                1140                1145                1150

Asp Gln Gln Arg Tyr His Glu Asp Ile Phe Gly Leu Thr Leu Arg Thr
                1155                1160                1165

Gln Glu Val Thr Ser Arg Ile Arg Thr Gln Ser Phe Ser Leu Gln Glu
    1170                1175                1180
```

-continued

```
Arg His Leu Arg Gly Ala Val Pro Trp Ala Phe Asp Pro Pro Gly Pro
1185                1190                1195                1200

Asp Thr Pro Gly Pro
            1205

<210> SEQ ID NO 2
<211> LENGTH: 1203
<212> TYPE: PRT
<213> ORGANISM: Homo sapiens
<220> FEATURE:
<221> NAME/KEY: SOURCE
<222> LOCATION: 1..1203
<223> OTHER INFORMATION: /mol_type="protein"
      /organism="Homo sapiens"

<400> SEQUENCE: 2

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
                20                  25                  30

Thr Pro Ala Pro Glu Pro Ser Arg Ala Pro Ala Ser Leu Leu Pro Pro
            35                  40                  45

Ala Pro Glu His Ser Pro Ser Ser Pro Leu Thr Gln Pro Pro Glu
50                  55                  60

Gly Pro Lys Phe Pro Arg Val Lys Asn Trp Glu Val Gly Ser Ile Thr
65                  70                  75                  80

Tyr Asp Thr Leu Ser Ala Gln Ala Gln Asp Gly Pro Cys Thr Pro
                85                  90                  95

Arg Arg Cys Leu Gly Ser Leu Val Phe Pro Arg Lys Leu Gln Gly Arg
            100                 105                 110

Pro Ser Pro Gly Pro Pro Ala Pro Glu Gln Leu Leu Ser Gln Ala Arg
            115                 120                 125

Asp Phe Ile Asn Gln Tyr Tyr Ser Ser Ile Lys Arg Ser Gly Ser Gln
130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
            180                 185                 190

Leu Gln Val Phe Asp Ala Arg Asp Cys Arg Ser Ala Gln Glu Met Phe
            195                 200                 205

Thr Tyr Ile Cys Asn His Ile Lys Tyr Ala Thr Asn Arg Gly Asn Leu
210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
            260                 265                 270

Leu Cys Ile Gln His Gly Trp Thr Pro Gly Asn Gly Arg Phe Asp Val
            275                 280                 285

Leu Pro Leu Leu Leu Gln Ala Pro Asp Glu Pro Pro Glu Leu Phe Leu
290                 295                 300

Leu Pro Pro Glu Leu Val Leu Glu Val Pro Leu Glu His Pro Thr Leu
305                 310                 315                 320
```

-continued

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
            340                 345                 350

Phe Ser Gly Trp Tyr Met Ser Thr Glu Ile Gly Thr Arg Asn Leu Cys
        355                 360                 365

Asp Pro His Arg Tyr Asn Ile Leu Glu Asp Val Ala Val Cys Met Asp
    370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
        435                 440                 445

Val Pro Pro Ile Ser Gly Ser Leu Thr Pro Val Phe His Gln Glu Met
    450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
                485                 490                 495

Lys Glu Val Ala Asn Ala Val Lys Ile Ser Ala Ser Leu Met Gly Thr
            500                 505                 510

Val Met Ala Lys Arg Val Lys Ala Thr Ile Leu Tyr Gly Ser Glu Thr
        515                 520                 525

Gly Arg Ala Gln Ser Tyr Ala Gln Gln Leu Gly Arg Leu Phe Arg Lys
    530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
        595                 600                 605

Tyr Lys Ile Arg Phe Asn Ser Ile Ser Cys Ser Asp Pro Leu Val Ser
    610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
        675                 680                 685

Cys Gly Gln Glu Glu Ala Phe Arg Gly Trp Ala Gln Ala Ala Phe Gln
    690                 695                 700

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
                725                 730                 735

Leu Ser Ala Gln Ala Glu Gly Leu Gln Leu Leu Pro Gly Leu Ile His

-continued

```
                740                 745                 750
Val His Arg Arg Lys Met Phe Gln Ala Thr Ile Arg Ser Val Glu Asn
            755                 760                 765

Leu Gln Ser Ser Lys Ser Thr Arg Ala Thr Ile Leu Val Arg Leu Asp
            770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
            805                 810                 815

Val Glu Asp Pro Pro Ala Pro Thr Glu Pro Val Ala Val Glu Gln Leu
            820                 825                 830

Glu Lys Gly Ser Pro Gly Gly Pro Pro Gly Trp Val Arg Asp Pro
            835                 840                 845

Arg Leu Pro Pro Cys Thr Leu Arg Gln Ala Leu Thr Phe Phe Leu Asp
            850                 855                 860

Ile Thr Ser Pro Pro Ser Pro Gln Leu Leu Arg Leu Leu Ser Thr Leu
865                 870                 875                 880

Ala Glu Glu Pro Arg Glu Gln Gln Leu Glu Ala Leu Ser Gln Asp
            885                 890                 895

Pro Arg Arg Tyr Glu Glu Trp Lys Trp Phe Arg Cys Pro Thr Leu Leu
            900                 905                 910

Glu Val Leu Glu Gln Phe Pro Ser Val Ala Leu Pro Ala Pro Leu Leu
            915                 920                 925

Leu Thr Gln Leu Pro Leu Leu Gln Pro Arg Tyr Tyr Ser Val Ser Ser
            930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
            965                 970                 975

Ser Thr Trp Leu Ser Gln Leu Lys Pro Gly Asp Pro Val Pro Cys Phe
            980                 985                 990

Ile Arg Gly Ala Pro Ser Phe Arg Leu Pro Pro Asp Pro Ser Leu Pro
            995                 1000                1005

Cys Ile Leu Val Gly Pro Gly Thr Gly Ile Ala Pro Phe Arg Gly Phe
            1010                1015                1020

Trp Gln Glu Arg Leu His Asp Ile Glu Ser Lys Gly Leu Gln Pro Thr
1025                1030                1035                1040

Pro Met Thr Leu Val Phe Gly Cys Arg Cys Ser Gln Leu Asp His Leu
                    1045                1050                1055

Tyr Arg Asp Glu Val Gln Asn Ala Gln Gln Arg Gly Val Phe Gly Arg
            1060                1065                1070

Val Leu Thr Ala Phe Ser Arg Glu Pro Asp Asn Pro Lys Thr Tyr Val
            1075                1080                1085

Gln Asp Ile Leu Arg Thr Glu Leu Ala Ala Glu Val His Arg Val Leu
            1090                1095                1100

Cys Leu Glu Arg Gly His Met Phe Val Cys Gly Asp Val Thr Met Ala
1105                1110                1115                1120

Thr Asn Val Leu Gln Thr Val Gln Arg Ile Leu Ala Thr Glu Gly Asp
                    1125                1130                1135

Met Glu Leu Asp Glu Ala Gly Asp Val Ile Gly Val Leu Arg Asp Gln
            1140                1145                1150

Gln Arg Tyr His Glu Asp Ile Phe Gly Leu Thr Leu Arg Thr Gln Glu
            1155                1160                1165
```

Val Thr Ser Arg Ile Arg Thr Gln Ser Phe Ser Leu Gln Glu Arg Gln
    1170                1175                1180

Leu Arg Gly Ala Val Pro Trp Ala Phe Asp Pro Pro Gly Ser Asp Thr
1185                1190                1195                1200

Asn Ser Pro

<210> SEQ ID NO 3
<211> LENGTH: 4
<212> TYPE: PRT
<213> ORGANISM: Bos taurus
<220> FEATURE:
<221> NAME/KEY: SOURCE
<222> LOCATION: 1..4
<223> OTHER INFORMATION: /mol_type="protein"
      /organism="Bos taurus"

<400> SEQUENCE: 3

Pro Trp Ala Phe
1

<210> SEQ ID NO 4
<211> LENGTH: 4
<212> TYPE: PRT
<213> ORGANISM: Bos taurus
<220> FEATURE:
<221> NAME/KEY: SOURCE
<222> LOCATION: 1..4
<223> OTHER INFORMATION: /mol_type="protein"
      /organism="Bos taurus"

<400> SEQUENCE: 4

Gly Ala Val Pro
1

<210> SEQ ID NO 5
<211> LENGTH: 21
<212> TYPE: PRT
<213> ORGANISM: Bos taurus
<220> FEATURE:
<221> NAME/KEY: SOURCE
<222> LOCATION: 1..21
<223> OTHER INFORMATION: /mol_type="protein"
      /organism="Bos taurus"

<400> SEQUENCE: 5

Arg His Leu Arg Gly Ala Val Pro Trp Ala Phe Asp Pro Pro Gly Pro
1               5                   10                  15

Asp Thr Pro Gly Pro
            20

<210> SEQ ID NO 6
<211> LENGTH: 12
<212> TYPE: PRT
<213> ORGANISM: Bos taurus
<220> FEATURE:
<221> NAME/KEY: SOURCE
<222> LOCATION: 1..12
<223> OTHER INFORMATION: /mol_type="protein"
      /organism="Bos taurus"

<400> SEQUENCE: 6

Ala Phe Asp Pro Pro Gly Pro Asp Thr Pro Gly Pro
1               5                   10

<210> SEQ ID NO 7
<211> LENGTH: 11

```
<212> TYPE: PRT
<213> ORGANISM: Bos taurus
<220> FEATURE:
<221> NAME/KEY: SOURCE
<222> LOCATION: 1..11
<223> OTHER INFORMATION: /mol_type="protein"
      /organism="Bos taurus"

<400> SEQUENCE: 7

His Leu Arg Gly Ala Val Pro Trp Ala Phe Asp
1               5                   10

<210> SEQ ID NO 8
<211> LENGTH: 20
<212> TYPE: PRT
<213> ORGANISM: Bos taurus
<220> FEATURE:
<221> NAME/KEY: SOURCE
<222> LOCATION: 1..20
<223> OTHER INFORMATION: /mol_type="protein"
      /organism="Bos taurus"

<400> SEQUENCE: 8

His Leu Arg Gly Ala Val Pro Trp Ala Phe Asp Pro Pro Gly Pro Asp
1               5                   10                  15

Thr Pro Gly Pro
            20
```

METHOD OF INCREASING THE EFFECT OF AN ACTIVATED-POTENTIATED FORM OF AN ANTIBODY

FIELD

The present invention relates to a method of increasing the effect of an activated-potentiated form of an antibody and a pharmaceutical formulation comprising an activated-potentiated form of an antibody to an endogenous biological molecule and an activated-potentiated form of an antibody to endothelial NO-synthase.

BACKGROUND

Nitric oxide (NO) is a gaseous molecule that has been shown to acts in the signaling of different biological processes. Endothelium-derived NO is a key molecule in regulation of vascular tone and its association with vascular disease has long been recognized. NO inhibits many processes known to be involved in the formation of atherosclerotic plaque, including monocyte adhesion, platelet aggregation and vascular smooth muscle cell proliferation. Another important role of endothelial NO is the protection of the vascular wall from the oxidative stress induced by its own metabolic products and by the oxidation products of lipids and lipoproteins. Endothelial dysfunction occurs at very early stages of atherosclerosis. It is therefore possible that deficiency in local NO availability could be a final common pathway that accelerates atherogenesis in humans. In addition to its role in the vascular endothelium, NO availability has been shown to modulate metabolism of lipoproteins. Negative correlation has been reported between plasma concentrations of NO metabolic products and plasma total and Low Density Lipoprotein [LDL] cholesterol levels while High Density Lipoprotein [HDL] improves vascular function in hypercholesterolaemic subjects. The loss of NO has considerable effect on the development of the disease. Diabetes mellitus is associated with increased rates of morbidity and mortality caused primarily by the accelerated development of atherosclerotic disease. Moreover, reports show that diabetics have impaired lung functions. It has been proposed that insulin resistance leads to airway inflammation. Habib et al., *Nitric Oxide Measurement From Blood To Lungs, Is There A Link?* Pak J Physiol 2007; 3(1).

Nitric oxide is synthesized by the endothelium from L-arginine by nitric oxide synthase (NO synthase). NO synthase occurs in different isoforms, including a constitutive form (cNOS) and an inducible form (iNOS). The constitutive form is present in normal endothelial cells, neurons and some other tissues.

The therapeutic effect of an extremely diluted form (or ultra-low form) of antibodies potentized by homeopathic technology (activated potentiated form) has been discovered by Dr. Oleg I. Epshtein. U.S. Pat. No. 7,700,096 discloses a homeopathically potentized form of antibodies to endothelial NO-synthase. The homeopathically potentized form of antibodies to endothelial NO-synthase is marketed in the Russian Federation and other countries under the name Impaza®.

There is a continuing need for a method of increasing the effect of an activated-potentiated form of an antibody.

SUMMARY

In accordance with one aspect, the present invention provides a method of increasing the effect of an activated-potentiated form of an antibody to an endogenous biological molecule, said method comprising combining said endogenous biological molecule with an activated-potentiated form of an antibody to endothelial NO-synthase. Preferably, the method aspect of the invention includes administering said combination to a patient in need of treatment with said activated-potentiated form of an antibody.

In one variant, said activated-potentiated form of an antibody to an endogenous biological molecule is an antibody to S-100 protein. In another variant, said activated-potentiated form of an antibody to an endogenous biological molecule is an antibody to prostate specific antigen. In another variant, said activated-potentiated form an antibody to an endogenous biological molecule is an antibody to insulin receptor. In another variant, said activated-potentiated form an antibody to an endogenous biological molecule is an antibody to antigiotensin receptor II.

In accordance with another aspect, the invention provides a pharmaceutical composition comprising a) an activated-potentiated form of an antibody to an endogenous biological molecule, and b) an activated-potentiated form of an antibody to NO synthase. Preferably, the pharmaceutical composition pharmaceutically acceptable solid carrier. Preferably, the activated-potentiated form of an antibody to endothelial NO synthase contains a mixture of C12, C30, and C200 homeopathic dilutions impregnated onto the solid carrier. The activated-potentiated form of an antibody to an endogenous biological molecule could be a monoclonal, monoclonal, or natural antibody. Preferably, the antibody to human insulin receptor is a polyclonal antibody.

It is contemplated that the pharmaceutical composition comprises an activated-potentiated form of an antibody to an endogenous biological molecule prepared by successive centesimal dilutions coupled with shaking of every dilution. It is also contemplated that the antibody to endothelial NO-synthase is monoclonal, polyclonal or natural antibody. It is particularly preferred that the antibody to endothelial NO-synthase is a polyclonal antibody. It is contemplated that the activated-potentiated form of an antibody to endothelial NO-synthase is prepared by successive centesimal dilutions coupled with shaking of every dilution.

DETAILED DESCRIPTION

Figure 1:
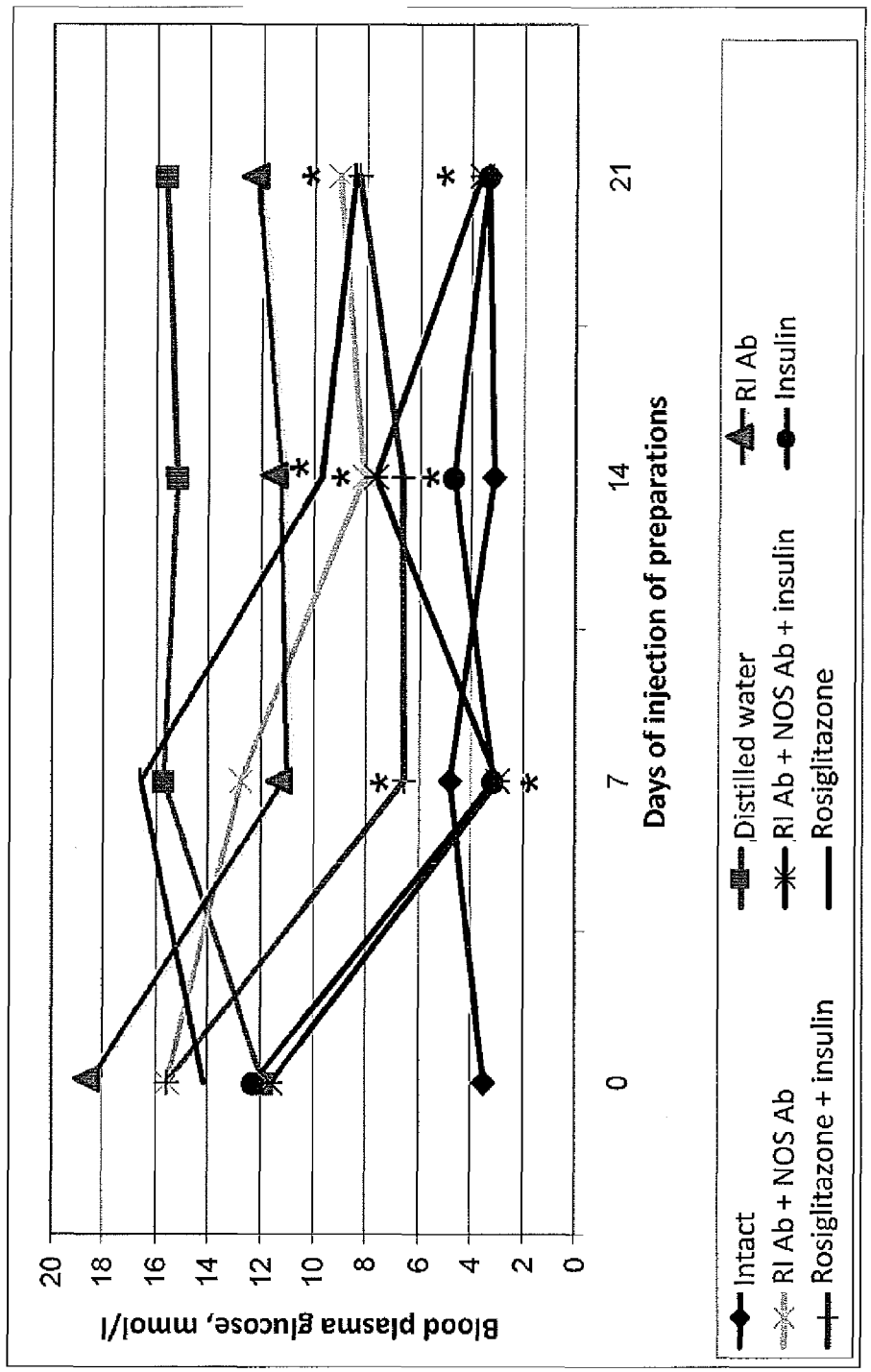
FIG. 1—Illustrates the effect of tested preparations on blood plasma glucose level of rats with streptozotocin-induced diabetes mellitus FIG. 2—Illustrates the effect of tested preparations on day 14 of injection on indicators of area under concentration-time curve (AUC) in the glucose tolerance test in rats with streptozotocin-induced diabetes mellitus.

The invention is defined with reference to the appended claims. With respect to the claims, the glossary that follows provides the relevant definitions.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')$_2$, Fab', and the like. The singular "antibody" includes plural "antibodies."

The term "activated-potentiated form" or "potentiated form" respectively, with respect to antibodies recited herein is used to denote a product of homeopathic potentization of any initial solution of antibodies. "Homeopathic potentization" denotes the use of methods of homeopathy to impart homeopathic potency to an initial solution of relevant substance. Although not so limited, 'homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions (C12, C30, and C200) or the use of the mixture of three aqueous or aqueous-alcohol dilutions of the primary matrix solution of antibodies diluted $100^{12}$, $100^{30}$ and $100^{50}$ times, respectively, which is equivalent to centesimal homeopathic dilutions (C12, C30 and C50). Examples of homeopathic potentization are described in U.S. Pat. Nos. 7,572,441 and 7,582,294, which are incorporated herein by reference in their entirety and for the purpose stated. While the term "activated-potentiated form" is used in the claims, the term "ultra-low doses" is used in the examples. The term "ultra-low doses" became a term of art in the field of art created by study and use of homeopathically diluted and potentized form of substance. The term "ultra-low dose" or "ultra-low doses" is meant as fully supportive and primarily synonymous with the term 'activated-potentiated" form used in the claims.

In other words, an antibody is in the "activated-potentiated" or "potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. And third, the biological activity exhibited by the "activated potentiated" form of the antibody cannot be explained by the presence of the molecular form of the antibody in the final product of the homeopathic process.

For example, the activated potentiated form of antibodies may be prepared by subjecting an initial, isolated antibody in a molecular form to consecutive multiple dilutions coupled with an external impact, such as mechanical shaking. The external treatment in the course of concentration reduction may also be accomplished, for example, by exposure to ultrasonic, electromagnetic, or other physical factors. V. Schwabe "Homeopathic medicines", M., 1967, U.S. Pat. Nos. 7,229,648 and 4,311,897, which are incorporated by reference in their entirety and for the purpose stated, describe such processes that are well-accepted methods of homeopathic potentiation in the homeopathic art. This procedure gives rise to a uniform decrease in molecular concentration of the initial molecular form of the antibody. This procedure is repeated until the desired homeopathic potency is obtained. For the individual antibody, the required homeopathic potency can be determined by subjecting the intermediate dilutions to biological testing in the desired pharmacological model. Although not so limited, 'homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably, water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200 or the mixture of three aqueous or aqueous-alcohol dilutions of the primary matrix solution (mother tincture) of antibodies diluted $100^{12}$, $100^{30}$ and $100^{50}$ times, respectively, which is equivalent to centesimal homeopathic dilutions C12, C30 and C50. Examples of how to obtain the desired potency are also provided, for example, in U.S. Pat. Nos. 7,229,648 and 4,311,897, which are incorporated by reference for the purpose stated. The procedure applicable to the "activated-potentiated" form of the antibodies described herein is described in more detail below.

There has been a considerable amount of controversy regarding homeopathic treatment of human subjects. While the present invention relies on accepted homeopathic processes to obtain the "activated-potentiated" form of antibodies, it does not rely solely on homeopathy in human subjects for evidence of activity. It has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. The "activated-potentiated" form of the antibody provided herein are tested for biological activity in well accepted pharmacological models of activity, either in appropriate in vitro experiments, or in vivo in suitable animal models. The experiments provided further below provide evidence of biological activity in such models. Human clinical studies also provide evidence that the activity observed in the animal model is well translated to human therapy. Human studies have also provided evidence of availability of the "activated potentiated" forms described herein to treat specified human diseases or disorders well accepted as pathological conditions in the medical science.

Also, the claimed "activated-potentiated" form of antibody encompasses only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated' form of the antibodies of the present invention is not attributable to the initial molecular form of the antibody. Preferred is the "activated-potentiated" form of antibody in liquid or solid form in which the concentration of the molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the molecular form of the antibody is below the Avogadro number. In the pharmacology of molecular forms of therapeutic substances, it is common practice to create a dose-response curve in which the level of pharmacological response is plotted against the concentration of the active drug administered to the subject or tested in vitro. The minimal level of the drug which produces any detectable response is known as a threshold dose. It is specifically contemplated and preferred that the "activated-potentiated" form of the antibodies contains molecular antibody, if any, at a concentration below the threshold dose for the molecular form of the antibody in the given biological model.

The combination pharmaceutical composition in accordance with this aspect of the invention may be in the liquid form or in solid form. Each of the activated potentiated forms of the antibodies included in the pharmaceutical composition is prepared from an initial molecular form of the antibody via a process accepted in homeopathic art. The starting antibodies may be monoclonal, or polyclonal antibodies prepared in accordance with known processes, for example, as described in Immunotechniques, G. Frimel, M., "Meditsyna", 1987, p. 9-33; "Hum. Antibodies. Monoclonal and recombinant antibodies, 30 years after" by Laffly E., Sodoyer R.—2005—Vol. 14.—N 1-2. P. 33-55, both incorporated herein by reference.

Monoclonal antibodies may be obtained, e.g., by means of hybridoma technology. The initial stage of the process includes immunization based on the principles already developed in the course of polyclonal antisera preparation. Further stages of work involve the production of hybrid cells generating clones of antibodies with identical specificity. Their separate isolation is performed using the same methods as in the case of polyclonal antisera preparation.

Polyclonal antibodies may be obtained via active immunization of animals. For this purpose, for example, suitable animals (e.g. rabbits) receive a series of injections of the appropriate antigen, for example, NO synthase. The animals' immune system generates corresponding antibodies, which are collected from the animals in a known manner. This procedure enables preparation of a monospecific antibody-rich serum.

If desired, the serum containing antibodies may be purified, for example by using affine chromatography, fractionation by salt precipitation, or ion-exchange chromatography. The resulting purified, antibody-enriched serum may be used as a starting material for the preparation of the activated-potentiated form of the antibodies. The preferred concentration of the resulting initial solution of antibody in the solvent, preferably water or a water-ethyl alcohol mixture, ranges from about 0.5 to about 5.0 mg/ml.

The preferred procedure for preparing each component of the combination drug according to the present invention is the use of the mixture of three aqueous-alcohol dilutions of the primary matrix solution of antibodies diluted $100^{12}$, $100^{30}$ and $100^{50}$ times, respectively, which is equivalent to centesimal homeopathic dilutions C12, C30, and C50 or diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In a preferred embodiment, the starting material for the preparation of the activated potentiated form that comprise the combination of the invention is polyclonal, animal-raised antibody to the corresponding antigen, namely, NO synthase and endogenous biological molecule. To obtain the activated-potentiated form of polyclonal antibodies to NO synthase, the desired antigen may be injected as immunogen into a laboratory animal, preferably, rabbits. Polyclonal antibodies to NO synthase may be obtained using the whole molecule of bovine NO synthase of the following sequence:

SEQ ID NO: 1

| Met | Gly | Asn | Leu | Lys | Ser | Val | Gly | Gln | Glu | Pro | Gly | Pro | Pro | Cys |
|---|---|---|---|---|---|---|---|---|---|---|---|---|---|---|
| 1 | | | | 5 | | | | | 10 | | | | | 15 |

| Gly | Leu | Gly | Leu | Gly | Leu | Gly | Leu | Gly | Leu | Cys | Gly | Lys | Gln | Gly |
|---|---|---|---|---|---|---|---|---|---|---|---|---|---|---|
| 16 | | | | 20 | | | | | 25 | | | | | 30 |

| Pro | Ala | Ser | Pro | Ala | Pro | Glu | Pro | Ser | Arg | Ala | Pro | Ala | Pro | Ala |
|---|---|---|---|---|---|---|---|---|---|---|---|---|---|---|
| 31 | | | | 35 | | | | | 40 | | | | | 45 |

| Thr | Pro | His | Ala | Pro | Asp | His | Ser | Pro | Ala | Pro | Asn | Ser | Pro | Thr |
|---|---|---|---|---|---|---|---|---|---|---|---|---|---|---|
| 46 | | | | 50 | | | | | 55 | | | | | 60 |

| Leu | Thr | Arg | Pro | Pro | Glu | Gly | Pro | Lys | Phe | Pro | Arg | Val | Lys | Asn |
|---|---|---|---|---|---|---|---|---|---|---|---|---|---|---|
| 61 | | | | 65 | | | | | 70 | | | | | 75 |

| Trp | Glu | Leu | GLys | er | Ile | Thr | Tyr | Asp | Thr | Leu | Cys | Ala | Gln | Ser |
|---|---|---|---|---|---|---|---|---|---|---|---|---|---|---|
| 76 | | | | 80 | | | | | 85 | | | | | 90 |

| Gln | Gln | Asp | Gly | Pro | Cys | Thr | Pro | Arg | Cys | Cys | Leu | GLys | er | Leu |
|---|---|---|---|---|---|---|---|---|---|---|---|---|---|---|
| 91 | | | | 95 | | | | | 100 | | | | | 105 |

| Val | Leu | Pro | Arg | Lys | Leu | Gln | Thr | Arg | Pro | Ser | Pro | Gly | Pro | Pro |
|---|---|---|---|---|---|---|---|---|---|---|---|---|---|---|
| 106 | | | | 110 | | | | | 115 | | | | | 120 |

| Pro | Ala | Glu | Gln | Leu | Leu | Ser | Gln | Ala | Arg | Asp | Phe | Ile | Asn | Gln |
|---|---|---|---|---|---|---|---|---|---|---|---|---|---|---|
| 121 | | | | 125 | | | | | 130 | | | | | 135 |

-continued

```
Tyr Tyr Ser Ser Ile Lys Arg Ser GLys er Gln Ala His Glu Glu
136                 140                 145                 150

Arg Leu Gln Glu Val Glu Ala Glu Val Ala Ser Thr Gly Thr Tyr
151                 155                 160                 165

His Leu Arg Glu Ser Glu Leu Val Phe Gly Ala Lys Gln Ala Trp
166                 170                 175                 180

Arg Asn Ala Pro Arg Cys Val Gly Arg Ile Gln Trp Gly Lys Leu
181                 185                 190                 195

Gln Val Phe Asp Ala Arg Asp Cys Ser Ser Ala Gln Glu Met Phe
196                 200                 205                 210

Thr Tyr Ile Cys Asn His Ile Lys Tyr Ala Thr Asn Arg Gly Asn
211                 215                 220                 225

Leu Arg Ser Ala Ile Thr Val Phe Pro Gln Arg Ala Pro Gly Arg
226                 230                 235                 240

Gly Asp Phe Arg Ile Trp Asn Ser Gln Leu Val Arg Tyr Ala Gly
241                 245                 250                 255

Tyr Arg Gln Gln Asp GLys er Val Arg Gly Asp Pro Ala Asn Val
256                 260                 265                 270

Glu Ile Thr Glu Leu Cys Ile Gln His Gly Trp Thr Pro Gly Asn
271                 275                 280                 285

Gly Arg Phe Asp Val Leu Pro Leu Leu Gln Ala Pro Asp Glu
286                 290                 295                 300

Ala Pro Glu Leu Phe Val Leu Pro Pro Glu Leu Val Leu Glu Val
301                 305                 310                 315

Pro Leu Glu His Pro Thr Leu Glu Trp Phe Ala Ala Leu Gly Leu
316                 320                 325                 330

Arg Trp Tyr Ala Leu Pro Ala Val Ser Asn Met Leu Leu Glu Ile
331                 335                 340                 345

Gly Gly Leu Glu Phe Ser Ala Ala Pro Phe Ser Gly Trp Tyr Met
346                 350                 355                 360

Ser Thr Glu Ile Gly Thr Arg Asn Leu Cys Asp Pro His Arg Tyr
361                 365                 370                 375

Asn Ile Leu Glu Asp Val Ala Val Cys Met Asp Leu Asp Thr Arg
376                 380                 385                 390

Thr Thr Ser Ser Leu Trp Lys Asp Lys Ala Ala Val Glu Ile Asn
391                 395                 400                 405

Leu Ala Val Leu His Ser Phe Gln Leu Ala Lys Val Thr Ile Val
406                 410                 415                 420

Asp His His Ala Ala Thr Val Ser Phe Met Lys His Leu Asp Asn
421                 425                 430                 435

Glu Gln Lys Ala Arg Gly Gly Cys Pro Ala Asp Trp Ala Trp Ile
436                 440                 445                 450

Val Pro Pro Ile Ser GLys er Leu Thr Pro Val Phe His Gln Glu
451                 455                 460                 465

Met Val Asn Tyr Ile Leu Ser Pro Ala Phe Arg Tyr Gln Pro Asp
466                 470                 475                 480

Pro Trp Lys GLy Ser Ala Thr Lys Gly Ala Gly Ile Thr Arg Lys
481                 485                 490                 495

Lys Thr Phe Lys Glu Val Ala Asn Ala Val Lys Ile Ser Ala Ser
496                 500                 505                 510

Leu Met Gly Thr Leu Met Ala Lys Arg Val Lys Ala Thr Ile Leu
511                 515                 510                 525

Tyr Ala Ser Glu Thr Gly Arg Ala Gln Ser Tyr Ala Gln Gln Leu
526                 530                 535                 540
```

```
Gly Arg Leu Phe Arg Lys Ala Phe Asp Pro Arg Val Leu Cys Met
541             545                 550                 555

Asp Glu Tyr Asp Val Val Ser Leu Glu His Glu Ala Leu Val Leu
556             560                 565                 570

Val Val Thr Ser Thr Phe Gly Asn Gly Asp Pro Pro Glu Asn Gly
571             575                 580                 585

Glu Ser Phe Ala Ala Ala Leu Met Glu Met Ser Gly Pro Tyr Asn
586             590                 595                 600

Ser Ser Pro Arg Pro Glu Gln His Lys Ser Tyr Lys Ile Arg Phe
601             605                 610                 615

Asn Ser Val Ser Cys Ser Asp Pro Leu Val Ser Ser Trp Arg Arg
616             620                 625                 630

Lys Arg Lys Glu Ser Ser Asn Thr Asp Ser Ala Gly Ala Leu Gly
631             635                 640                 645

Thr Leu Arg Phe Cys Val Phe Gly Leu GLy Ser Arg Ala Tyr Pro
646             650                 655                 660

His Phe Cys Ala Phe Ala Arg Ala Val Asp Thr Arg Leu Glu Glu
661             665                 670                 675

Leu Gly Gly Glu Arg Leu Leu Gln Leu Gly Gln Gly Asp Glu Leu
676             680                 685                 690

Cys Gly Gln Glu Glu Ala Phe Arg Gly Trp Ala Lys Ala Ala Phe
691             695                 700                 705

Gln Ala Ser Cys Glu Thr Phe Cys Val Gly Glu Ala Lys Ala
706             710                 715                 720

Ala Ala Gln Asp Ile Phe Ser Pro Lys Arg Ser Trp Lys Arg Gln
721             725                 730                 735

Arg Tyr Arg Leu Ser Thr Gln Ala Glu Gly Leu Gln Leu Leu Pro
736             740                 745                 750

Gly Leu Ile His Val His Arg Arg Lys Met Phe Gln Ala Thr Val
751             755                 760                 765

Leu Ser Val Glu Asn Leu Gln Ser Ser Lys Ser Thr Arg Ala Thr
766             770                 775                 780

Ile Leu Val Arg Leu Asp Thr Ala Gly Gln Glu Gly Leu Gln Tyr
781             785                 790                 795

Gln Pro Gly Asp His Ile Gly Ile Cys Pro Pro Asn Arg Pro Gly
796             800                 805                 810

Leu Val Glu Ala Leu Leu Ser Arg Val Glu Asp Pro Pro Pro
811             815                 820                 825

Thr Glu Ser Val Ala Val Glu Gln Leu Glu Lys GLys er Pro Gly
826             830                 835                 840

Gly Pro Pro Pro Ser Trp Val Arg Asp Pro Arg Leu Pro Pro Cys
841             845                 850                 855

Thr Leu Arg Gln Ala Leu Thr Phe Phe Leu Asp Ile Thr Ser Pro
856             860                 865                 870

Pro Ser Pro Arg Leu Leu Arg Leu Leu Ser Thr Leu Ala Glu Glu
871             875                 880                 885

Pro Ser Glu Gln Gln Glu Leu Glu Thr Leu Ser Gln Asp Pro Arg
886             890                 895                 900

Arg Tyr Glu Glu Trp Lys Trp Phe Arg Cys Pro Thr Leu Leu Glu
901             905                 910                 915

Val Leu Glu Gln Phe Pro Ser Val Ala Leu Pro Ala Pro Leu Leu
916             920                 925                 930

Leu Thr Gln Leu Pro Leu Leu Gln Pro Arg Tyr Tyr Ser Val Ser
931             935                 940                 945
```

-continued

```
Ser Ala Pro Asn Ala His Pro Gly Glu Val His Leu Thr Val Ala
946             950             955             960

Val Leu Ala Tyr Arg Thr Gln Asp Gly Leu Gly Pro Leu His Tyr
961             965             970             975

Gly Val Cys Ser Thr Trp Leu Ser Gln Leu Lys Thr Gly Asp Pro
976             980             985             990

Val Pro Cys Phe Ile Arg Gly Ala Pro Ser Phe Arg Leu Pro Pro
991             995             1000            1005

Asp Pro Tyr Val Pro Cys Ile Leu Val Gly Pro Gly Thr Gly Ile
1006            1010            1015            1020

Ala Pro Phe Arg Gly Phe Trp Gln Glu Arg Leu His Asp Ile Glu
1021            1025            1030            1035

Ser Lys Gly Leu Gln Pro Ala Pro Met Thr Leu Val Phe Gly Cys
1036            1040            1045            1050

Arg Cys Ser Gln Leu Asp His Leu Tyr Arg Asp Glu Val Gln Asp
1051            1055            1060            1065

Ala Gln Glu Arg Gly Val Phe Gly Arg Val Leu Thr Ala Phe Ser
1066            1070            1075            1080

Arg Glu Pro Asp Ser Pro Lys Thr Tyr Val Gln Asp Ile Leu Arg
1081            1085            1090            1095

Thr Glu Leu Ala Ala Glu Val His Arg Val Leu Cys Leu Glu Arg
1096            1100            1105            1110

Gly His Met Phe Val Cys Gly Asp Val Thr Met Ala Thr Ser Val
1111            1115            1120            1125

Leu Gln Thr Val Gln Arg Ile Leu Ala Thr Glu Gly Asp Met Glu
1126            1130            1135            1140

Leu Asp Glu Ala Gly Asp Val Ile Gly Val Leu Arg Asp Gln Gln
1141            1145            1150            1155

Arg Tyr His Glu Asp Ile Phe Gly Leu Thr Leu Arg Thr Gln Glu
1156            1160            1165            1170

Val Thr Ser Arg Ile Arg Thr Gln Ser Phe Ser Leu Gln Glu Arg
1171            1175            1180            1185

His Leu Arg Gly Ala Val Pro Trp Ala Phe Asp Pro Pro Gly Pro
1186            1190            1195            1200

Asp Thr Pro Gly Pro
1201            1205
```

Polyclonal antibodies to NO synthase may be obtained using the whole molecule of human NO synthase of the following sequence:

```
                                                SEQ ID NO: 2
Met Gly Asn Leu Lys Ser Val Ala Gln Glu Pro Gly Pro Pro Cys
1               5               10              15

Gly Leu Gly Leu Gly Leu Gly Leu Cys Gly Lys Gln Gly
16              20              25              30

Pro Ala Thr Pro Ala Pro Glu Pro Ser Arg Ala Pro Ala Ser Leu
31              35              40              45

Leu Pro Pro Ala Pro Glu His Ser Pro Ser Ser Pro Leu Thr
46              50              55              60

Gln Pro Pro Glu Gly Pro Lys Phe Pro Arg Val Lys Asn Trp Glu
61              65              70              75

Val GLys er Ile Thr Tyr Asp Thr Leu Ser Ala Gln Ala Gln Gln
76              80              85              90
```

-continued

```
Asp Gly Pro Cys Thr Pro Arg Arg Cys Leu GLys er Leu Val Phe
 91              95                 100                 105

Pro Arg Lys Leu Gln Gly Arg Pro Ser Pro Gly Pro Pro Ala Pro
106             110                 115                 120

Glu Gln Leu Leu Ser Gln Ala Arg Asp Phe Ile Asn Gln Tyr Tyr
121             125                 130                 135

Ser Ser Ile Lys Arg Ser GLys er Gln Ala His Glu Gln Arg Leu
136             140                 145                 150

Gln Glu Val Glu Ala Glu Val Ala Ala Thr Gly Thr Tyr Gln Leu
151             155                 160                 165

Arg Glu Ser Glu Leu Val Phe Gly Ala Lys Gln Ala Trp Arg Asn
166             170                 175                 180

Ala Pro Arg Cys Val Gly Arg Ile Gln Trp Gly Lys Leu Gln Val
181             185                 190                 195

Phe Asp Ala Arg Asp Cys Arg Ser Ala Gln Glu Met Phe Thr Tyr
196             200                 205                 210

Ile Cys Asn His Ile Lys Tyr Ala Thr Asn Arg Gly Asn Leu Arg
211             215                 220                 225

Ser Ala Ile Thr Val Phe Pro Gln Arg Cys Pro Gly Arg Gly Asp
226             230                 235                 240

Phe Arg Ile Trp Asn Ser Gln Leu Val Arg Tyr Ala Gly Tyr Arg
241             245                 250                 255

Gln Gln Asp GLy Ser Val Arg Gly Asp Pro Ala Asn Val Glu Ile
256             260                 265                 270

Thr Glu Leu Cys Ile Gln His Gly Trp Thr Pro Gly Asn Gly Arg
271             275                 280                 285

Phe Asp Val Leu Pro Leu Leu Leu Gln Ala Pro Asp Glu Pro Pro
286             290                 295                 300

Glu Leu Phe Leu Leu Pro Pro Glu Leu Val Leu Glu Val Pro Leu
301             305                 310                 315

Glu His Pro Thr Leu Glu Trp Phe Ala Ala Leu Gly Leu Arg Trp
316             320                 325                 330

Tyr Ala Leu Pro Ala Val Ser Asn Met Leu Leu Glu Ile Gly Gly
331             335                 340                 345

Leu Glu Phe Pro Ala Ala Pro Phe Ser Gly Trp Tyr Met Ser Thr
346             350                 355                 360

Glu Ile Gly Thr Arg Asn Leu Cys Asp Pro His Arg Tyr Asn Ile
361             365                 370                 375

Leu Glu Asp Val Ala Val Cys Met Asp Leu Asp Thr Arg Thr Thr
376             380                 385                 390

Ser Ser Leu Trp Lys Asp Lys Ala Ala Val Glu Ile Asn Val Ala
391             395                 400                 405

Val Leu His Ser Tyr Gln Leu Ala Lys Val Thr Ile Val Asp His
406             410                 415                 420

His Ala Thr Ala Ser Phe Met Lys His Leu Glu Asn Glu Gln
421             425                 430                 435

Lys Ala Arg Gly Gly Cys Pro Ala Asp Trp Ala Trp Ile Val Pro
436             440                 445                 450

Pro Ile Ser GLys er Leu Thr Pro Val Phe His Gln Glu Met Val
451             455                 460                 465

Asn Tyr Phe Leu Ser Pro Ala Phe Arg Tyr Gln Pro Asp Pro Trp
466             470                 475                 480

Lys Gly Ser Ala Ala Lys Gly Thr Gly Ile Thr Arg Lys Lys Thr
481             485                 490                 495
```

```
Phe Lys Glu Val Ala Asn Ala Val Lys Ile Ser Ala Ser Leu Met
496                 500                 505                 510

Gly Thr Val Met Ala Lys Arg Val Lys Ala Thr Ile Leu Tyr Gly
511                 515                 510                 525

Ser Glu Thr Gly Arg Ala Gln Ser Tyr Ala Gln Gln Leu Gly Arg
526                 530                 535                 540

Leu Phe Arg Lys Ala Phe Asp Pro Arg Val Leu Cys Met Asp Glu
541                 545                 550                 555

Tyr Asp Val Val Ser Leu Glu His Glu Thr Leu Val Leu Val Val
556                 560                 565                 570

Thr Ser Thr Phe Gly Asn Gly Asp Pro Glu Asn Gly Glu Ser
571                 575                 580                 585

Phe Ala Ala Ala Leu Met Glu Met Ser Gly Pro Tyr Asn Ser Ser
586                 590                 595                 600

Pro Arg Pro Glu Gln His Lys Ser Tyr Lys Ile Arg Phe Asn Ser
601                 605                 610                 615

Ile Ser Cys Ser Asp Pro Leu Val Ser Ser Trp Arg Arg Lys Arg
616                 620                 625                 630

Lys Glu Ser Ser Asn Thr Asp Ser Ala Gly Ala Leu Gly Thr Leu
631                 635                 640                 645

Arg Phe Cys Val Phe Gly Leu GLys er Arg Ala Tyr Pro His Phe
646                 650                 655                 660

Cys Ala Phe Ala Arg Ala Val Asp Thr Arg Leu Glu Glu Leu Gly
661                 665                 670                 675

Gly Glu Arg Leu Leu Gln Leu Gly Gln Gly Asp Glu Leu Cys Gly
676                 680                 685                 690

Gln Glu Glu Ala Phe Arg Gly Trp Ala Gln Ala Ala Phe Gln Ala
691                 695                 700                 705

Ala Cys Glu Thr Phe Cys Val Gly Glu Asp Ala Lys Ala Ala Ala
706                 710                 715                 720

Arg Asp Ile Phe Ser Pro Lys Arg Ser Trp Lys Arg Gln Arg Tyr
721                 725                 730                 735

Arg Leu Ser Ala Gln Ala Glu Gly Leu Gln Leu Leu Pro Gly Leu
736                 740                 745                 750

Ile His Val His Arg Arg Lys Met Phe Gln Ala Thr Ile Arg Ser
751                 755                 760                 765

Val Glu Asn Leu Gln Ser Ser Lys Ser Thr Arg Ala Thr Ile Leu
766                 770                 775                 780

Val Arg Leu Asp Thr Gly Gly Gln Glu Gly Leu Gln Tyr Gln Pro
781                 785                 790                 795

Gly Asp His Ile Gly Val Cys Pro Pro Asn Arg Pro Gly Leu Val
796                 800                 805                 810

Glu Ala Leu Leu Ser Arg Val Glu Asp Pro Pro Ala Pro Thr Glu
811                 815                 820                 825

Pro Val Ala Val Glu Gln Leu Glu Lys Gly Ser Pro Gly Gly Pro
826                 830                 835                 840

Pro Pro Gly Trp Val Arg Asp Pro Arg Leu Pro Pro Cys Thr Leu
841                 845                 850                 855

Arg Gln Ala Leu Thr Phe Phe Leu Asp Ile Thr Ser Pro Pro Ser
856                 860                 865                 870

Pro Gln Leu Leu Arg Leu Leu Ser Thr Leu Ala Glu Glu Pro Arg
871                 875                 880                 885

Glu Gln Gln Glu Leu Glu Ala Leu Ser Gln Asp Pro Arg Arg Tyr
886                 890                 895                 900
```

-continued

```
Glu Glu Trp Lys Trp Phe Arg Cys Pro Thr Leu Leu Glu Val Leu
901             905             910             915

Glu Gln Phe Pro Ser Val Ala Leu Pro Ala Pro Leu Leu Leu Thr
916             920             925             930

Gln Leu Pro Leu Leu Gln Pro Arg Tyr Tyr Ser Val Ser Ser Ala
931             935             940             945

Pro Ser Thr His Pro Gly Glu Ile His Leu Thr Val Ala Val Leu
946             950             955             960

Ala Tyr Arg Thr Gln Asp Gly Leu Gly Pro Leu His Tyr Gly Val
961             965             970             975

Cys Ser Thr Trp Leu Ser Gln Leu Lys Pro Gly Asp Pro Val Pro
976             980             985             990

Cys Phe Ile Arg Gly Ala Pro Ser Phe Arg Leu Pro Pro Asp Pro
991             995             1000            1005

Ser Leu Pro Cys Ile Leu Val Gly Pro Gly Thr Gly Ile Ala Pro
1006            1010            1015            1020

Phe Arg Gly Phe Trp Gln Glu Arg Leu His Asp Ile Glu Ser Lys
1021            1025            1030            1035

Gly Leu Gln Pro Thr Pro Met Thr Leu Val Phe Gly Cys Arg Cys
1036            1040            1045            1050

Ser Gln Leu Asp His Leu Tyr Arg Asp Glu Val Gln Asn Ala Gln
1051            1055            1060            1065

Gln Arg Gly Val Phe Gly Arg Val Leu Thr Ala Phe Ser Arg Glu
1066            1070            1075            1080

Pro Asp Asn Pro Lys Thr Tyr Val Gln Asp Ile Leu Arg Thr Glu
1081            1085            1090            1095

Leu Ala Ala Glu Val His Arg Val Leu Cys Leu Glu Arg Gly His
1096            1100            1105            1110

Met Phe Val Cys Gly Asp Val Thr Met Ala Thr Asn Val Leu Gln
1111            1115            1120            1125

Thr Val Gln Arg Ile Leu Ala Thr Glu Gly Asp Met Glu Leu Asp
1126            1130            1135            1140

Glu Ala Gly Asp Val Ile Gly Val Leu Arg Asp Gln Gln Arg Tyr
1141            1145            1150            1155

His Glu Asp Ile Phe Gly Leu Thr Leu Arg Thr Gln Glu Val Thr
1156            1160            1165            1170

Ser Arg Ile Arg Thr Gln Ser Phe Ser Leu Gln Glu Arg Gln Leu
1171            1175            1180            1185

Arg Gly Ala Val Pro Trp Ala Phe Asp Pro Pro Gly Ser Asp Thr
1186            1190            1195            1200

Asn Ser Pro
1201    1203
```

To obtain polyclonal antibodies to NO synthase, it is also possible to use a fragment of NO synthase, selected, for example, from the following sequences:

```
                                                SEQ ID NO: 3
Pro Trp Ala Phe
1192        1195

SEQ ID NO: 4
Gly Ala Val Pro
1189        1192
```

-continued

```
                                                     SEQ ID NO: 5
                                                  Arg
                                                  1185
His Leu Arg Gly Ala Val Pro Trp Ala Phe Asp Pro Pro Gly Pro
1186            1190            1195            1200
Asp Thr Pro Gly Pro
1201        1205

SEQ ID NO: 6
                                 Ala Phe Asp Pro Pro Gly Pro
                                 11941195            1200
Asp Thr Pro Gly Pro
1201        1205

SEQ ID NO: 7
His Leu Arg Gly Ala Val Pro Trp Ala Phe Asp
1186            1190            1195 1196

SEQ ID NO: 8
His Leu Arg Gly Ala Val Pro Trp Ala Phe Asp Pro Pro Gly Pro
1186            1190            1195            1200
Asp Thr Pro Gly Pro
1201        1205
```

The exemplary procedure for preparation of the starting polyclonal antibodies to NO synthase may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections.

To obtain antiserum containing the desired antibodies, the immunized rabbits' blood is collected from rabbits and placed in a 50 ml centrifuge tube. Product clots formed on the tube sides are removed with a wooden spatula, and a rod is placed into the clot in the tube center. The blood is then placed in a refrigerator for one night at the temperature of about 40° C. On the following day, the clot on the spatula is removed, and the remaining liquid is centrifuged for 10 min at 13,000 rotations per minute. Supernatant fluid is the target antiserum. The obtained antiserum is typically yellow. 20% of $NaN_3$ (weight concentration) is added in the antiserum to a final concentration of 0.02% and stored before use in frozen state at the temperature of −20° C. or without $NaN_3$ at the temperature of −70° C. To separate the target antibodies to gamma interferon from the antiserum, the following solid phase absorption sequence is suitable:

10 ml of the antiserum of rabbits is diluted twofold with 0.15 M NaCl, after which 6.26 g $Na_2SO_4$ is added, mixed and incubated for 12-16 hours at 4° C. The sediment is removed by centrifugation, diluted in 10 ml of phosphate buffer and dialyzed against the same buffer during one night at ambient temperature. After the sediment is removed, the solution is applied to a DEAE-cellulose column balanced by phosphate buffer. The antibody fraction is determined by measuring the optical density of the eluate at 280 nm.

The isolated crude antibodies are purified using affine chromatography method by attaching the obtained antibodies to NO synthase located on the insoluble matrix of the chromatography media, with subsequent elution by concentrated aqueous salt solutions.

The resulting buffer solution is used as the initial solution for the homeopathic dilution process used to prepare the activated-potentiated form of the antibodies. The preferred concentration of the initial matrix solution of the antigen-purified polyclonal rabbit antibodies to NO synthase is 0.5 to 5.0 mg/ml, preferably, 2.0 to 3.0 mg/ml.

The polyclonal antibodies to endogenous biological molecule may also be obtained by a similar methodology to the methodology described for endothelial NO synthase antibodies using an adjuvant.

The resulting buffer solution is used as the initial solution for the homeopathic dilution process used to prepare the activated potentiated form of the antibodies.

The activated potentiated form of each component of the combination may be prepared from an initial solution by homeopathic potentization, preferably using the method of proportional concentration decrease by serial dilution of 1 part of each preceding solution (beginning with the initial solution) in 9 parts (for decimal dilution), or in 99 parts (for centesimal dilution), or in 999 parts (for millesimal dilution) of a neutral solvent, starting with a concentration of the initial solution of antibody in the solvent, preferably, water or a water-ethyl alcohol mixture, in the range from about 0.5 to about 5.0 mg/ml, coupled with external impact. Preferably, the external impact involves multiple vertical shaking (dynamization) of each dilution. Preferably, separate containers are used for each subsequent dilution up to the required potency level, or the dilution factor. This method is well-accepted in the homeopathic art. See, e.g. V. Schwabe "*Homeopathic medicines*", M., 1967, p. 14-29, incorporated herein by reference for the purpose stated.

For example, to prepare a 12-centesimal dilution (denoted C12), one part of the initial matrix solution of antibodies to NO synthase with the concentration of 3.0 mg/ml is diluted in 99 parts of neutral aqueous or aqueous-alcohol solvent (preferably, 15%-ethyl alcohol) and then vertically shaked many times (10 and more) to create the 1st centesimal dilution (denoted as C1). The 2nd centesimal dilution (C2) is prepared from the 1st centesimal dilution C1. This procedure is repeated 11 times to prepare the 12th centesimal dilution C12. Thus, the 12th centesimal dilution C12 represents a solution obtained by 12 serial dilutions of one part of the initial matrix solution of antibodies with the concentration of 3.0 mg/ml in 99 parts of a neutral solvent in different containers, which is equivalent to the centesimal homeopathic dilution C12. Similar procedures with the relevant dilution factor are performed to obtain the desired dilutions. The intermediate dilutions may be tested in a desired biological model to check activity.

The preferred activated potentiated forms for antibodies comprising the combination of the invention is a C12, C30 and C200 dilutions for each activated-potentiated form. When using the mixture of various homeopathic dilutions (primarily centesimal) of the active substance as biologically active liquid component, each component of the composition (e.g., C12, C30, C50, C200) is prepared separately according to the above-described procedure until the next-to-last dilution is obtained (e.g., until C11, C29, and C199 respectively), and then one part of each component is added in one container according to the mixture composition and mixed with the required quantity of the solvent (e.g. with 97 parts for centesimal dilution).

It is possible to use the active substance as mixture of various homeopathic dilutions, e.g. decimal and/or centesimal (D20, C30, C100 or C12, C30, C50 or C12, C30, C200, etc.), the efficiency of which is determined experimentally by testing the dilution in a suitable biological model, for example, in models described in the examples herein.

In the course of potentiation and concentration decrease, the vertical shaking may be substituted for external exposure to ultrasound, electromagnetic field or any similar external impact procedure accepted in the homeopathic art.

The solid unit dosage form of the pharmaceutical composition of the invention may be prepared by using impregnating a solid, pharmaceutically acceptable carrier with the mixture of the activated potentiated form aqueous or aqueous-alcohol solutions of active components that are mixed, primarily in 1:1 ratio and used in liquid dosage form. Alternatively, the carrier may be impregnated consecutively with each requisite dilution.

Preferably, the pharmaceutical composition in the solid unit dosage form is prepared from granules of the pharmaceutically acceptable carrier which was previously saturated with the aqueous or aqueous-alcoholic dilutions of the activated potentiated form of antibodies. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono-oligo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc), including lubricants, disintegrants, binders and coloring agents. The preferred carriers are lactose and isomalt. The pharmaceutical dosage form may further include standard pharmaceutical excipients, for example, microcrystalline cellulose, magnesium stearate and citric acid.

The example of preparation of the solid unit dosage form is set forth below. To prepare the solid oral form, 100-300 μm granules of lactose are impregnated with aqueous or aqueous-alcoholic solutions of the activated potentiated form of antibodies to histamine, activated-potentiated form of antibodies to NO synthase and the activated potentiated form of antibodies to an endogenous biological molecule in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Hüttlin Pilotlab" by Hüttlin GmbH) with subsequent drying via heated air flow at a temperature below 40° C. The estimated quantity of the dried granules (10 to 34 weight parts) saturated with the activated potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch-XL 400 tablet press) to form 150 to 500 mg round pills, preferably, 300 mg. After tableting, 300 mg pills are obtained that are saturated with aqueous-alcohol solution (3.0-6.0 mg/pill) of the combination of the activated-potentiated form of antibodies. Each component of the combination used to impregnate the carrier is in the form of a mixture of centesimal homeopathic dilutions, preferably, C12, C30 and C200.

While the invention is not limited to any specific theory, it is believed that the activated-potentiated form of the antibodies described herein do not contain the molecular form of the antibody in an amount sufficient to have biological activity attributed to such molecular form. The biological activity of the combination drug (combination pharmaceutical composition) of the invention is amply demonstrated in the appended examples.

Preferably, for the purpose of treatment, the combination of the invention is administered from once daily to four times daily, preferably twice daily, each administration including one or two combination unit dosage forms.

The invention is further illustrated with reference to the appended non-limiting examples.

EXAMPLES

Example 1

Study of effect of a complex preparation containing ultralow doses (ULD) of activated-potentiated forms of polyclonal affinity purified rabbit antibodies to brain-specific protein S-100 (anti-S100) and endothelial NO-synthase (anti-eNOS), obtained by super-dilution of initial matrix solution (concentration: 2.5 mg/ml) ($100^{12}$, $100^{30}$, $100^{200}$ times), equivalent to a blend of centesimal homeopathic dilutions C12, C30, C200 (ratio: 1:1) (ULD of anti-S100+anti-eNOS), as well as its components—activated-potentiated form of polyclonal affinity purified rabbit antibodies to ultralow doses (ULD) of brain-specific protein S-100 (anti-S100), purified on antigen, obtained by super-dilution of initial matrix solution ($100^{12}$, $100^{30}$, $100^{200}$ times, equivalent to a blend of centesimal homeopathic dilution C12, C30, C200, and activated-potentiated form of polyclonal rabbit antibodies to ultralow dose of endothelial NO-synthase (ULD of anti-eNOS), obtained by super-dilution of initial matrix solution ($100^{12}$, $100^{30}$, $100^{200}$ times), equivalent to a blend of centesimal homeopathic dilution C12, C30, C200 in vitro on binding of standard ligand [$^3$H]pentazocine to human recombinant σ1 receptor was evaluated using radioligand method. Potentiated distilled water (blend of homeopathic dilutions C12+C30+C200) was used as test preparations control.

Sigma-1 (σ1) receptor—an intracellular one which is localized in the cells of central nervous system, the cells of the most of peripheral tissues and immune component cells. Receptors exhibit a unique ability to be translocated which is caused by many psychotropic medications. The dynamics of sigma-1 receptors is directly linked to various influences which are performed by preparations acting to the sigma-1 receptors. These effects include the regulation of activity channels, ecocytosis, signal transferring, remodeling of the plasma membrane (formation of rafts) and lipid transportation/metabolism. All this can contribute to the plasticity of neurons in a brain. There is evidence that the sigma-1 receptors have a modulating effect on all the major neuromediator systems: noradrenergic, serotonergic, dopaminergic, cholinergic systems and NMDA- adjustable glutamate effects. Sigma-1 receptor plays an important role in the pathophysiology of neurodegenerative diseases (e.g., Alzheimer's disease, Parkinson), psychiatric and affective disorders and stroke; and it also takes part in the processes of learning and memory. In this regard, the ability of drugs to influence the efficiency of interaction of ligands with sigma-1 receptor indicates on the presence of neuroprotective, anti-ischemic, anxiolytic, antidepressant and anti astenic components in the spectrum of its pharmacological activity that allows the consideration of these drugs as effective preparations particularly for the treatment of cerebrovascular diseases.

During the test (to measure total binding) 20 µl of complex preparation of ULD of anti-S100+anti-eNOS or 10 µl of ULD of AB to S100 or 10 µl of ULD of AB to NOS were transferred in the incubation medium. Thus, the quantity of ULD of anti-S100+anti-eNOS, transferred into the test basin when testing the complex preparation was identical to that of ULD of AB to S100 and ULD of AB to NOS tested as monopreparations, which allow comparing the efficiency of the preparation to its separate components. 20 µl and 10 µl of potentiated water were transferred in the incubation medium.

Further, 160 µl (about 200 µg of protein) of Jurkat cell line membranes homogenate (human leukemic T-lymphocyte line), and finally, 20 µl of tritium-labeled radioligand [$^3$H] pentazocine (15 nm) were transferred.

In order to measure non-specific binding, 20 µl of non-labeled ligand-haloperidol (10 µM) were transferred in the incubation medium instead of the preparations or potentiated water.

Radioactivity was measured using a scintillometer (Topcount, Packard) and scintillation blend (Microscint 0, Packard) following the incubation within 120 minutes at 22° C. in 50 mM Tris-HCl buffer (pH=7.4) and filtration using fiberglass filters (GF/B, Packard). Specific binding (during the test or control) was calculated as a difference between total (during the test or control) and non-specific binding.

Results are represented as percentage of specific binding inhibition in control (distilled water was used as control) (Table 1).

TABLE 1

| Test group | Quantity per test basin | % of radioligand specific binding in control | | | % of radioligand binding inhibition in control |
|---|---|---|---|---|---|
| | | 1$^{st}$ test | 2$^{nd}$ test | Average | |
| ULD of anti-S100 + anti-eNOS | 20 µl | 48.4 | 35.5 | 42.0 | 58.0 |
| ULD of anti-S100 | 10 µl | 67.3 | 63.1 | 65.2 | 34.8 |
| ULD of anti-eNOS | 10 µl | 147.5 | 161.1 | 154.3 | −54.3 |
| Potentiated water | 20 µl | 98.1 | 75.8 | 86.9 | 13.1 |
| Potentiated water | 10 µl | 140.1 | 106.2 | 123.2 | −23.2 |

Effect of the Preparations and Potentiated Water on Binding of Standard Ligand [$^3$H]Pentazocine to Human Recombinant σ1 Receptor Note: % of specific binding in control=(specific binding during the test/specific binding in control)*100%;
% of specific binding inhibition in control=100%−(specific binding during the test/specific binding in control)*100%).
The outcomes reflecting inhibition above 50% represent significant effects of the tested compounds; inhibition from 25% to 50% confirm mild to moderate effects; inhibition less than 25% is considered to be insignificant effect of the tested compound and is within background level.

Therefore, the conditions of this test model showed that the complex preparation of ULD of anti-S100+anti-eNOS is more efficient than its separate components (ULD of anti-S100 and ULD of anti-eNOS) in inhibiting the binding of standard radioligand [$^3$H]pentazocine to human recombinant σ1 receptor; ULD of anti-S100, transferred into the test basin, namely 10 µl, inhibit the binding of standard radioligand [3H]pentazocine to human recombinant σ1 receptor, but the effect intensity is inferior to that of the complex preparation of ULD of anti-S100+anti-eNOS; ULD of anti-eNOS, transferred into the test basin, namely 10 µl, had no effect on the binding of standard radioligand [3H]pentazocine to human recombinant σ1 receptor; potentiated water, transferred into the test basin, namely 10 µl or 20 µl, had no effect on the binding of standard radioligand [3H]pentazocine to human recombinant σ1 receptor.

Example 2

Alzheimer's disease (AD) is a neurodegenerative disease that is characterized by lowering of cognitive functions, memory deterioration, confused consciousness, and emotional changes. Although the main cause of this pathology is nowadays considered the accumulation of beta amyloid which leads to the formation of beta-amyloid plaques and neurofibrillary tangles in brain tissues; AD is also accompanied by a deficiency of cholinergic system. This is the basis of a most common way of modeling of AD in animals with the help of antagonist of cholinergic system of scopolamine. Injection of scopolamine into experimental animals (usually rats or mice) interrupts the ability to learn and leads to deterioration of memory.

Various methods were used to assess cognitive functions of rats and mice, including Morris water maze. The essence of this test is that the animals are released into a container with cloudy water from different points are forced to look for a hidden fixed platform. The advantage of this method is that it allows the researcher to monitor the process of animal training (the formation of ideas about the spatial alignment of the platform no matter where the animal was placed in the water) so as to assess the memory strength (for this the test is conducted when the platform is removed).

The effectiveness in rats with Scopolamine amnesia of the combination pharmaceutical composition of the present invention containing activated-potentiated forms of polyclonal affinity purified on antigen of rabbit brain-specific proteins S-100 (anti-S100) and to endothelial NO-syntheses (anti-eNOS) in ultra low doses (ULD) obtained by super dilution of storage stock solution (with concentration of 2.5 mg/ml) in $100^{12}$, $100^{30}$, $100^{200}$ times, equivalent to centesimal homeopathic dilutions C12, C30, C200 (ULD anti-S100+anti-eNOS) is studied.

In a study of the effectiveness of the drug ULD anti-S100+anti-eNOS in rats with scopolamine amnesia (a model of Alzheimer's disease) 48 male rats of the Rj: Wistar (Han) line (weight 180-280 g) were used. During 4 days the rats were subdermally injecting with normal saline (n=12, intact) or scopolamine in doze of 0.5 mg/kg (n=36) (scopolamine-induced amnesia). Rats with scopolamine-induced amnesia were divided into three groups and administered with distilled water (7.5 ml/kg, n=12, control group 1), or ULD anti-S100 (7.5 ml/kg, n=12, group 2) or ULD anti-S100+anti-eNOS (7.5 ml/kg, n=12, group 3) intragastrically for 9 days (4 days prior to the injection of scopolamine, 4 days against the background of scopolamine and 1 day after the last scopolamine injection).

The training session in the Morris water maze was conducted within 4 days of the scopolamine injection through 60 minutes after administration of tested drugs and 30 minutes after administration of scopolamine (4 sequential tests at interval of 60 seconds). Morris' maze is a round reservoir (diameter—150 cm, height—45 cm) at 30 cm filled with water (26-28° C.). At 18 cm from the edge of the container there is hidden platform (diameter—15 cm) buried on 1.5 cm below the water level. Cloudy water made by adding a non-toxic dye (e.g., milk powder) makes the platform invisible. For each test the animal was placed in a maze in one of the initial points that are equidistant from the hidden platform and the animal was allowed to find the platform. If the animal could not find the platform within 120 seconds, the animal was put on the platform and left for 60 seconds and the test was restarted. During the four tests in random order the animals began to walk through the maze twice from each starting point. The tests were recorded on videotape and then analyzed for distance overcomes searching the platform in each trial and the latent period of searching for the platform. On day 5 the test was performed: the platform was removed from the maze and rats were given free float for 60 seconds. The time spent in the place where the platform used to be was recorded.

The administration of scopolamine significantly worsened the ability of animals to learn. In the control group the time spent by animals searching for platforms and the distance that animals swam searching for the platform, significantly increased (Table 2, 3). The test shows that the memory of animals in the control group worsened: the animals in this group spent less time in the place where the platform used to be located than intact animals (Table 4). The administration of ULD anti-S100 didn't lead to improvement of the studied parameters (Tables 2, 3, 4). The administration of ULD anti-S100+anti-eNOS led to some improvement in learning which resulted in a shortening of the latent time of the platform search time (Table 2) and covered distance (Table 3) within 4 days of training and an improvement of memory as reflected in increase of the time spent in a place where the platform used to be located (Table 4).

TABLE 2

Latent period of the platform search, sec

| Group | Training | | | |
| --- | --- | --- | --- | --- |
| | $1^{st}$ day | $2^{nd}$ day | $3^{rd}$ day | $4^{th}$ day |
| Intact, n = 12 | 54.7 ± 6.2 | 30.8 ± 2.8 | 26.9 ± 5.1 | 20.5 ± 3.6 |
| Control, n = 12 | 100.1 ± 6.8*** | 92.4 ± 9.3*** | 81.4 ± 10.7*** | 77.7 ± 9.4*** |
| ULD anti-S100, n = 12 | 106.8 ± 7.0 | 99.3 ± 7.8 | 95.6 ± 9.0 | 80.4 ± 11.1 |
| ULD anti-S100 + anti-eNOS, n = 12 | 94.4 ± 7.2 | 90.7 ± 8.2 | 78.3 ± 8.6 | 60.1 ± 10.2 |

***difference from intact is significant, $p < 0.05$

TABLE 3

Distance overcome to search the platform, cm

| Group | Training | | | |
| --- | --- | --- | --- | --- |
| | $1^{st}$ day | $2^{nd}$ day | $3^{rd}$ day | $4^{th}$ day |
| Intact, n = 12 | 1055.7 ± 94.6 | 659.5 ± 62.2 | 564.8 ± 119.3 | 406.1 ± 61.2 |
| Control, n = 12 | 2587.1 ± 217.2*** | 2559.6 ± 250.5*** | 2397.9 ± 312.6 | 2366.1 ± 293.8*** |
| ULD anti-S100, n = 12 | 2797.2 ± 208.9 | 2865.2 ± 255.1 | 2857.0 ± 300.8 | 2457.4 ± 344.4 |
| ULD anti-S100 + anti-eNOS, n = 12 | 2434.3 ± 222.8 | 2529.9 ± 282.7 | 2344.2 ± 283.0 | 1905.1 ± 343.7 |

***difference from intact is significant, $p < 0.05$

TABLE 4

Time spent in a place where the platform used to be located, sec.

| Group | Test | | |
| --- | --- | --- | --- |
| | 0-30 sec. | 30-60 sec. | 0-60 sec. |
| Intact, n = 12 | 40.8 ± 4.1 | 36.8 ± 3.6 | 38.5 ± 2.6 |
| Control, n = 12 | 18.4 ± 2.8*** | 18.8 ± 1.9*** | 18.8 ± 1.7*** |
| ULD anti-S100, n = 12 | 13.3 ± 2.1 | 21.5 ± 2.6 | 17.6 ± 1.3 |
| ULD anti-S100 + anti-eNOS, n = 12 | 19.1 ± 4.8 | 23.8 ± 2.2 | 21.2 ± 2.5 |

***difference from intact is significant, $p < 0.05$

Thus, in model of Alzheimer's disease, the administratoin of the complex ULD anti-S100+anti-eNOS was more effective in comparison with administration of ULD anti-S100 and vehicle.

Example 3

The preclinical research studied the ultra low doses (ULD) of activated-potentiated forms of polyclonal affinity purified rabbit antibodies to brain-specific protein S-100 (anti-S100)

purified on antigen, and endothelial NO-synthase (anti-eNOS), obtained by super-dilution of initial matrix solution (concentration: 2.5 mg/ml) ($100^{12}$, $100^{30}$, $100^{200}$ times), equivalent to a mixture of centesimal homeopathic dilutions C12, C30, C200 (ratio: 1:1) (ULD anti-S100+anti-eNOS) in treating ischemic stroke caused by prefrontal cerebrocortical photothrombosis in rats.

Acute cerebrovascular disease (brain stroke) ranks third among lethality causes in developed countries and one of the main causes of disability in humans (Gusev E. I., 2003; Janardhan V., Qureshi A. I., 2004).

The photo-induced thrombosis model meets almost all requirements to the experimental model of focal cerebral ischemia. The method developed by Watson (Watson B. et al., 1985) is based on the effect of light with wavelength 560 nm on photosensitive pigment Bengal rose introduced into the blood flow. Active oxygen forms are created and caused increase in adhesiveness of endothelium cells and platelets, and formation of clots closing vascular lumens. The method of ischemic brain lesion induction by using photo-induced thrombosis is technically simple and to close to clinical forms of ischemic brain stroke. A great advantage of this model is that it is non-invasive, i.e. does not require craniotomy and, therefore, more accurately reproduces clinical picture of cerebral thrombosis.

Thirty seven male Wistar rats (weight: 150-180 g; age: 2-3 months) were included in the study of the activity of ULD anti-S100+anti-eNOS in rats with ischemic stroke caused by prefrontal cerebrocortical photothrombosis. Bilateral focal ischemic injury in prefrontal cerebral cortex in rats was induced using the photochemical thrombosis method by Watson (Watson B. D. et al., 1985) as modified by I. V. Viktorov (Romanova G. A. et al, 1998). Bengal rose (3% solution) was injected in the jugular vein of anesthetized rats (n=37) (anesthesia: chloral hydrate 300 mg/kg, intraperitoneally). Using a fiber optic bundle (3 cm in diameter) the light beam from halogen lamp (24 V, 250 W) was delivered to the skull surface above the frontal cortex of the left and right cerebral hemispheres to induce photothrombosis. Sham-operated rats (n=6) were subject to the same procedure except administration of bengal rose and exposure to halogen lamp light. The intact group included 6 rats.

Five days before and 9 days after stoke induction the following preparations were administered to rats with photothrombosis: distilled water (control-photothrombosis, 5 ml/kg daily, n=12), ULD anti-S100 (5 ml/kg daily, n=7) or ULD anti-S100+anti-eNOS (5 ml/kg daily, n=6). On Day 8 after the operation (or sham operation) conditioned passive avoidance reflex (CPAR) test was performed to assess learning capability and memory in rats. Rats were placed in a unit consisting of illuminated site and connected dark chamber, where animals were exposed to electric foot-shock of 0.45 mA due to which usually preferred dark chamber became dangerous. Development of conditioned passive avoidance reflex was tested on the next day. At that, rats were placed in the illuminated chamber. Latent period of the first entry in the dark chamber was recorded. If a rat avoided the dark chamber for a long time, a conclusion was made that it remembered the danger (electric shock). The longer the latent period of entry in the dark chamber, the better the memory.

Volume of the stroke lesion was morphologically assessed in a proportion of rats of experimental groups on Day 9.

In control rats photothrombosis caused formation of a large stroke area and, therefore, leaded to memory impairment: CPAR reproduction worsened by 9.6% compared to intact rats and by 22.9% compared to sham-operated (Table 5). Administration of ULD anti-S100 reduced the stroke volume by 42.2% and improved memory by 14.0% compared to control-photothrombosis group. Administration of ULD anti-S100+anti-eNOS was more effective: the stroke volume reduced by 44.0%, and conditioned reflex reproduction—by 33.4% compared to control-photothrombosis group.

Therefore, administration of the complex preparation of ULD anti-S100+anti-eNOS was more efficient than mono-component preparation of ULD anti-S100.

TABLE 5

| | Volume of focal stroke (mm3); the number of animals | Latent period of CPAR (seconds), the number of animals |
|---|---|---|
| Intact | — | 135.8 ± 28.8; n = 6 |
| Sham-operated | — | 159.3 ± 18.7; n = 6 |
| Control-photothrombosis | 3.41 ± 0.5; n = 9 | 122.8 ± 20.9; n = 12 |
| Photothrombosis + ULD anti-S100 | 1.97 ± 0.6; n = 4 | 140.0 ± 26.5; n = 7 |
| Photothrombosis + ULD anti-S100 + anti-eNOS | 1.91 ± 0.5; n = 4 | 163.8 ± 16.2; n = 6 |

Example 4

Study of the combination of "activated" potentiated forms of antibodies to a C-terminal fragment of the angiotensin II AT1-receptor, in a mixture of homeopathic dilutions of C12, C30, C200, with the activated potentiated form of antibodies to endothelial NO-synthase, in a mixture of homeopathic dilutions of C12, C30, C200, in SHR rats in a model of hypertension.

The combination of the "activated" potentiated form of antibodies to a C-terminal fragment of the angiotensin II AT1-receptor, in a mixture of homeopathic dilutions of C12, C30, C200, and the activated potentiated form of antibodies to endothelial NO-synthase in a mixture of homeopathic dilutions of C12, C30, C200, was studied, in solution form, in the SHR rat hypertension model. Investigations were conducted on 40 SHR line male rats from (weight 350±50 g, age 4.5-5 months) with hypertension, which were divided into 4 groups of 10 animals each.

For 28 days, the animals were treated as follows. Group 1 —2.5 ml/kg of the potentiated activated form of antibodies to a C-terminal fragment AT1 of human angiotensin II receptor (a mixture of aqueous dilutions C12, C30, C200) in combination with 2.5 ml/kg of distilled water, Group 2 —2.5 ml/kg of the potentiated activated form of antibodies to endothelial NO-synthase (a mixture of aqueous dilutions C12, C30, C200) in combination with 2.5 ml/kg of distilled water, Group 3 —5 ml/kg of the combination pharmaceutical composition (a mixture of aqueous dilutions C12, C30, C200 for each component), and Group 4 —5 ml/kg of distilled water.

Systolic blood pressure (SBP) of awake rats was measured with the aid of an indirect method in a tail artery (using a cuff) once a week and 9 hours after the last administration of medicines.

All tested compositions demonstrated hypotensive effect ($p<0.05$): by $28^{th}$ day, systolic blood pressure (SBD) decreased in comparison with the initial level in Group 1 by –20.6%; in Group 2 by 14.4%; in Group 3 by 27.6%. In the control Group 4, SBD changes were 1.6% in comparison with the initial values. The results demonstrate a clear synergistic hypotensive effect of the combination pharmaceutical composition.

Example 5

Study of the combination of the activated potentiated forms of antibodies to a C-terminal fragment of angiotensin II AT1- receptor, in a mixture of homeopathic dilutions of C12, C30, C200, with the activated potentiated form of antibodies to endothelial NO-synthase, in a mixture of homeopathic dilutions of C12, C30, C200, in NISAG rats in a model of hypertension.

The combination of the activated potentiated form of antibodies to a C-terminal fragment of angiotensin II AT1-receptor, in a mixture of homeopathic dilutions of C12, C30, C200, and the activated potentiated form of antibodies to endothelial NO-synthase in a mixture of homeopathic dilutions of C12, C30, C200, was studied, in solution form, in the NISAG rat hypertension model. Investigations were conducted on 50 NISAG line male rats (weight 300 g, age 4 months) with hereditary stipulated stress-sensitive arterial hypertension, which were divided into 5 groups by 10 animals each.

The animals were given per orally, once a day and for 28 days, the following medications: Group 1 —2.5 ml/kg of the activated potentiated form of antibodies to a C-terminal fragment AT1 of human angiotensin II receptor (a mixture of dilutions C12, C30, C200) in combination with 2.5 ml/kg of distilled water; Group 2 —2.5 ml/kg of the activated potentiated form of antibodies to endothelial NO-synthase (a mixture of dilutions C12, C30, C200) in combination with 2.5 ml/kg of distilled water; Group 3—5 ml/kg of the combination pharmaceutical composition (a mixture of homeopathic aqueous dilutions C12, C30, C200 of each component); Group 4—5 ml/kg (10 ml/kg dose) of the comparison drug (losartan); and Group 5—5 ml/kg of distilled water.

Two times a week, 2 to 6 hours after administration of VSD antibodies and losartan, systolic blood pressure (SBP) was measured by an indirect method in a tail artery (using a cuff). The Table 6 shows the dynamics of changes in systolic blood pressure in NISAG line rats, measured by indirect method.

intact. The rest were intravenously injected with streptozotocin at the dose of 50 mg/kg (experimental model of diabetes mellitus). 72 hours after injection of streptozotocin, rats with blood plasma glucose level not less than 12 mmol/1 were selected, divided into 7 groups (20 rats in each), which over 21 days were given distilled water (5 ml/kg/day, once daily intragastrically), Insulin® (8 units/kg/day, subcutaneously), Rosiglitazone® (8 mg/kg/day, twice daily intragastrically), ULD anti-IR (2.5 ml/kg/day in a volume of 5 ml/kg/day, once daily intragastrically), ULD anti-IR+ULD anti-eNOS (5 ml/kg/day, once daily intragastrically), and also Rosiglitazone® and Insulin® together or ULD anti-IR+ULD anti-eNOS and Insulin®, according to regimes corresponding to each preparation (as described above). Intact rats received distilled water in the same volume. On days 7, 14 and 21 of injection of preparations in rats, fasting blood plasma glucose level measured with enzymatic method (glucose oxidase method) with utilization of "glucose FKD" kits (Russia).

Oral glucose tolerance test (OGTT) was performed on day 14 of the study (day 14 of administration of preparation) according to standard method (Du Vigneaud and Karr, 1925). The rats were starving at water for 18 hours. 60 min before the test they were last given test substances. Intact rats received distilled water in the same volume. Glucose was administered per os 50% w/w water glucose solution (1 g/kg of rat weight). Serum glucose of blood sample from tail vein was measured by using "Glucose FKD" kit (OOO "Pharamaceutical and clinical diagnostics, Russia, www.fkd.ru) at 0, 30, 60, 90, 120 min. Mean area under the curve (AUC) concentration of blood glucose over time was calculated.

Injection of streptozotocin led to a substantial increase in blood plasma glucose of rats in comparison with intact animals (18 mmol/l versus 3.5 mmol/l, $p<0.05$). In the ULD

TABLE 6

| Indicator | Initial SBP in mmHg | SBP after 28 days of medicine administration in mmHg | Δ in comparison with the initial level, in mmHg | % of the initial level |
|---|---|---|---|---|
| VSD antibodies to C-terminal fragment AT1 of human angiotensin II receptor | 176 | 150 | −26 | −14.7% |
| VSD antibodies to endothelial NO-synthase | 175 | 164.5 | −10.5 | −6% |
| Combination medicine on the basis of VSD antibodies to C-tailed fragment AT1 of angiotensin II receptor and to endothelial NO-synthase | 179.5 | 140 | −39.5 | −22% |
| Losartan | 173.5 | 140.5 | −33 | −19% |
| Control (distilled water) | 181 | 178 | −3 | −1.6% |

Example 6

The experimental studiy investigated the effects of antibodies to the C-terminal fragment to the insulin receptor β-subunit affinity purified on antigen, in ultra-low dose, obtained by super dilution of the initial matrix solution $100^{12}$, $100^{30}$, $100^{200}$ times (ULD anti-IR), antibodies to endothelial NO-synthase affinity purified on antigen, in ultra-low dose, obtained by hyper-dilution of the initial matrix solution $100^{12}$, $100^{30}$, $100^{200}$ (ULD anti-ULD anti-eNOS), as well as the combination of ultra-low doses of antibodies to the C-terminal fragment to the insulin receptor β-subunit and ultra-low dose of antibodies to endothelial NO-synthase (ULD anti-IR+ULD anti-eNOS).

In the study, 150 male Wistar were used (weight at beginning of study 250-300 g, age 3.5-4 months). 10 rats were anti-IR group, on day 7, 14 and 21 of injection of preparation, glucose level was lower than in the control group by 22-28% on average; however, differences did not reach a statistically significant level. The combination of ULD anti-IR and anti-eNOS was more efficacious; the decrease in glucose level on days 14 and 21 of the experiment were 47% and 42%, respectively ($p<0.05$ versus control). The reference preparation, Rosiglitazone, also lowered glucose level by day 14 and 21 of the experiment; at that, the effect reached statistical significance on day 14 of the experiment only (36%, $p<0.05$ versus control).

Insulin, injected at ½ of the effective dose (selected in the preliminary study) most effectively lowered glucose level in all observation periods (down to the level of the intact control). (FIG. 1). It should be taken into account that short-acting insulin was used in the study and blood plasma glucose was measured 1 hour after its injection, which also influenced the effect of the ½ insulin dose on blood glucose level. Against this background it was not possible to fully determine what the effect of the combined use of insulin and rosiglitazone or insulin and complex ULD anti-IR+anti-eNOS is.

Figure 2:
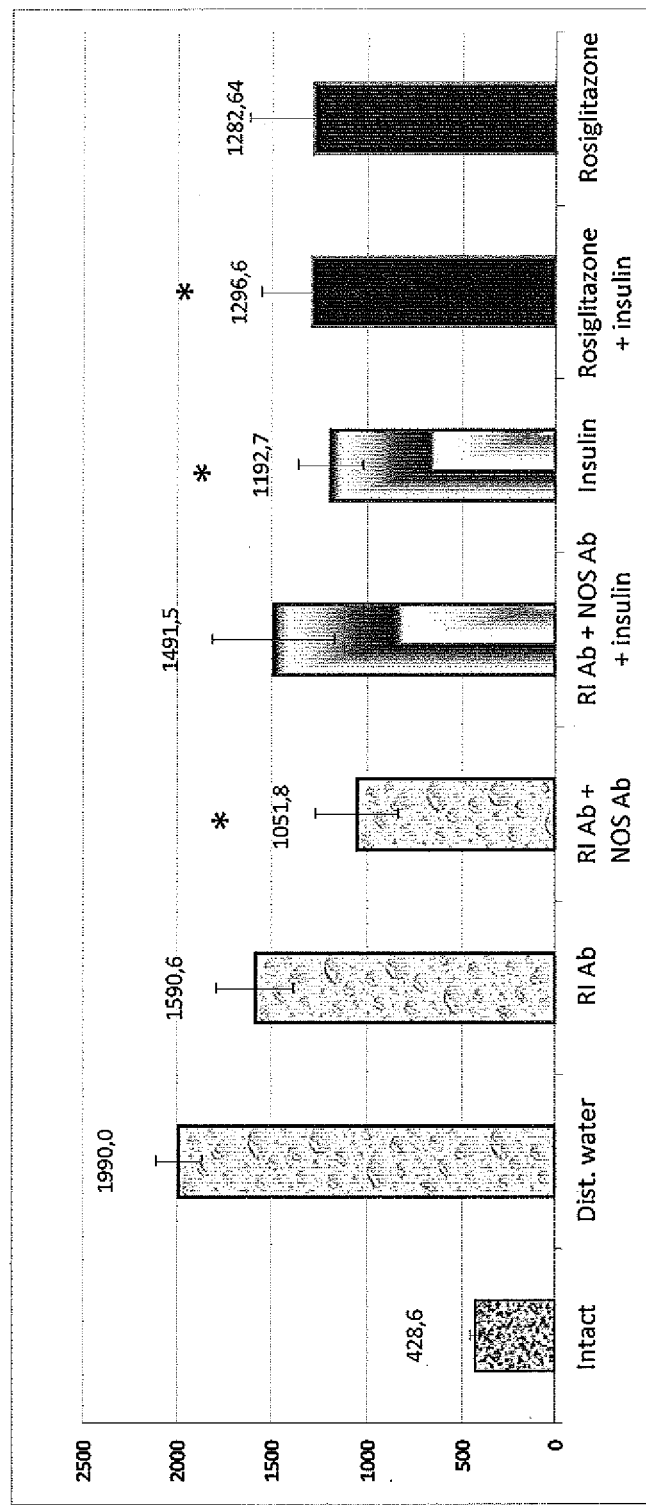

Glucose tolerance disturbance (reduction in glucose utilization by the body) is one of the most important indicators in diagnostic and treatment of diabetes mellitus. In intact animals, in the oral glucose tolerance test (day 14 of injection of preparations), complex preparation ULD anti-IR+ULD anti-eNOS and insulin most effectively increased glucose tolerance when administered alone. Rosiglitazone also reduced the area under concentration over time curve (increased glucose tolerance); however, its efficacy was not statistically significant versus the control group (FIG. 2).

Example 7

The experimental studiy investigated the effects of antibodies to the C-terminal fragment to the insulin receptor β-subunit affinity purified on antigen, in ultra-low dose, obtained by super dilution of the initial matrix solution $100^{12}$, $100^{30}$, $100^{200}$ times (ULD anti-IR), antibodies to endothelial NO-synthase affinity purified on antigen, in ultra-low dose, obtained by hyper-dilution of the initial matrix solution $100^{12}$, $100^{30}$, $100^{200}$ (ULD anti-ULD anti-eNOS), as well as the combination of ultra-low doses of antibodies to the C-terminal fragment to the insulin receptor β-subunit and ultra-low dose of antibodies to endothelial NO-synthase (ULD anti-IR+ULD anti-eNOS).

In the study, 36 male Goto-Kakizaki rats were used (weight at beginning of study 250-280 g, age 10-12 weeks). Rats of this line are characterized by spontaneous development of non-insulin-dependent diabetes. The animals were divided into 3 groups (12 rats in each) and received either distilled water (5 ml/kg, once daily intragastrically), or ULD anti-IR (2.5 ml/kg once daily intragastrically), or ULD anti-IR+ULD anti-eNOS (5 ml/kg, once daily intragastrically) for 28 days. Blood plasma glucose level was measured with the help of a glucose analyzer (Beckman, Fullerton, Calif., USA) before beginning injection of preparations and on day 4, 8, 12, 16, 20, 24, 28 of injection of preparations. On day 28, a glucose tolerance test was carried out (glucose p.o., 1 g/kg).

Figure 3:
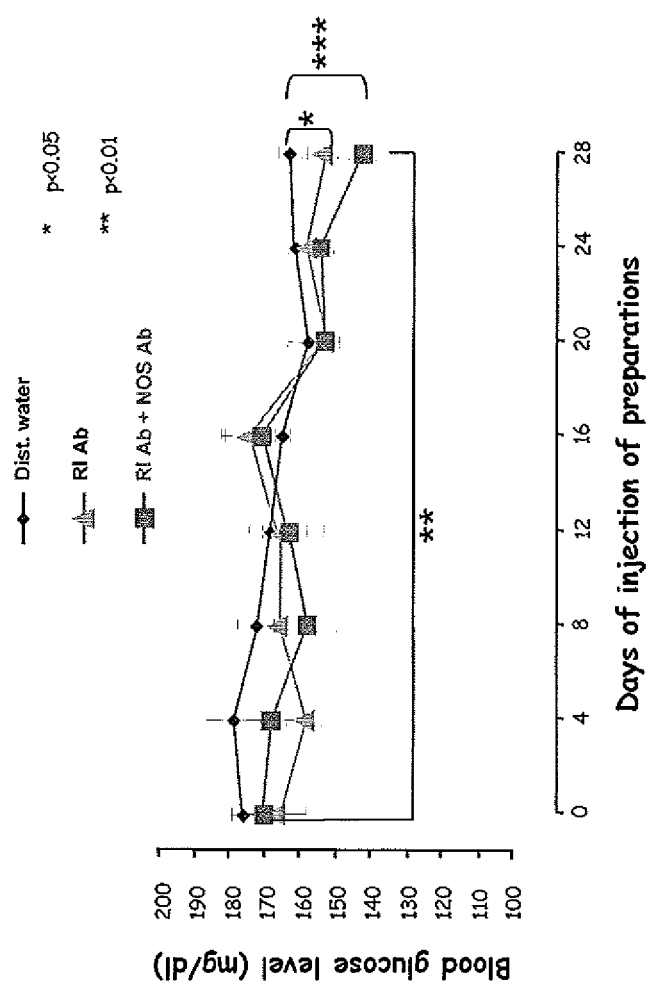
FIG. 3—Illustrates the effect of tested preparations on blood plasma glucose level of rats with spontaneous non-insulin-dependent diabetes mellitus.

Injection of ULD anti-IR led to a significant (p<0.05) drop in blood plasma glucose level of rats; however, the use of complex ULD anti-IR+ULD anti-eNOS was more efficacious (p<0.001 versus control) (FIG. 3).

Figure 4:
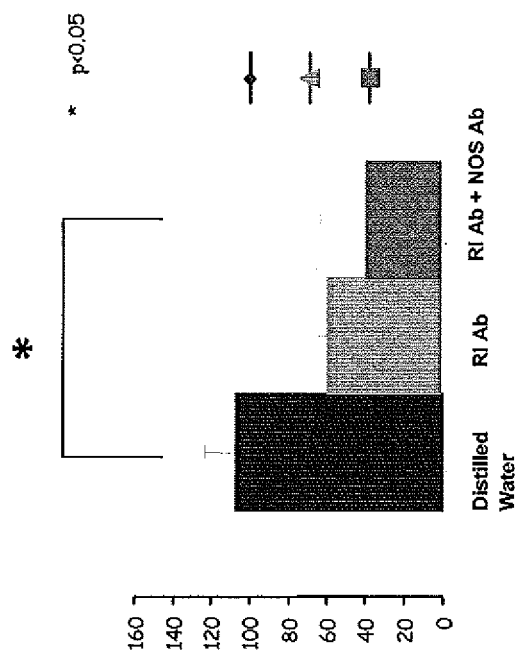
FIG. 4—Illustrates the effect of tested preparations on day 28 of injection on indicators of area under concentration-time curve (AUC) in glucose tolerance test in rats with spontaneous non-insulin-dependent diabetes mellitus.

The results were confirmed by glucose tolerance test data carried out on day 28 of injection of preparations (FIG. 4). Injection of ULD anti-IR led to an increase in glucose tolerance (statistically insignificant drop by 44% AUC versus control). At the same time, the reduction in this parameter (AUC) caused by injection of complex ULD anti-IR+ULD anti-eNOS was 62% and it was statistically significant versus control (p<0.05).

Example 8

The following preparation were used: 300 mg tablets impregnated with aqueous alcoholic solution (3 mg/tab.) activated-potentiated form of polyclonal rabbit brain-specific proteins antibodies S-100, purified on an antigen, in ultra low dose (ULD anti-S100) received by super dilution of initial solution (with concentration of 2.5 mg/ml) in $100^{12}$, $100^{30}$, $100^{200}$ times, of equivalent mixture of centesimal homeopathic dilutions C12, C30, C200; 300 mg tablets impregnated with pharmaceutical composition contained aqueous-alcohol solutions of (6 mg/tab) activated-potentiated forms of polyclonal affinity purified rabbit antibodies to brain-specific protein S-100 (anti S-100) and to eNOS (anti-eNOS) in ultra low dose (ULD), received by super dilution of initial solution (with concentration of 2.5 mg/ml) in $100^{12}$, $100^{30}$, $100^{200}$ times, of equivalent mixture of centesimal homeopathic dilutions C12, C30, C200; (ULD anti-S100+anti-eNOS); 300 mg tablets impregnated with aqueous-alcohol solution (3 mg/tab.) of activated-potentiated form of polyclonal rabbit eNOS antibodies purified on antigen in ultra low dose (ULD anti-eNOS), received by super dilution of initial solution (with concentration of 2.5 mg/ml) in $100^{12}$, $100^{30}$, $100^{200}$ times, of equivalent mixture of centesimal homeopathic dilutions C12, C30, C200; and as placebo 300 mg tablets containing excipients: lactose (lactose monohydrate)—267 mg, microcrystal cellulose—30 mg, magnesium stearate—3 mg.

The effectiveness of the studied drugs in the treatment of dizziness (vertigo) and other symptoms of motion sickness was evaluated on kinetosis model or motion diseases/motion sicknesses which occurs by various vestibular vegetative disorders. Dizziness is the typical sign of lesion of the vestibular analyzer of various genesis including dysfunction of the vestibular nerve and cochlear system, circulatory embarrassment in vertebral basilar system, pathology of the central nervous system (CNS), etc. Dizziness as a manifestation of kinetosis accompanied with other vestibular-vegetative disorders which include three types of reactions: the vestibular-motor (nystagmus and the reaction of deviation), vestibular-sensory (in addition to dizziness, nystagmus is (or reaction of post rotation), defensive movements) and vegetative (nausea, vomiting, sweating, palpitation, heat feeling, pulse and blood pressure fluctuations).

Double blind placebo controlled comparative study were conducted in parallel groups consisting of 15 somatically healthy subjects—males and females aged from 15 to 60 years (mean age 33.3±0.75 years) with low (n=5; 33%) or mean (n=10; 67%) degree of motion sickness resistance in order to test anti motion sickness properties of various compositions. Group I was given ULD anti-S100+anti-eNOS, Group 2 was given ULD anti-S100 and Group 3 was given anti-eNOS.

To simulate the condition of motion sickness and evaluate the effectiveness of studied drugs the most appropriate and recognized kinetosis models—test with a continuous cumulative effect of accelerations by Coriolis (CCEAC) was used. Initial tolerance of CCEAC test in all study subjects was not more than 5 minutes. Vestibular-vegetative disorders provoked by kinetic effect (CCEAC) were registered with usage of complex of diagnostic methods including subject's examination, quantitative evaluation of disorders of vestibular-vegetative sensitivity (Halle scale), analysis of heart rate variability (HRV), and self-esteem of functional condition (WBAM—well-being, activity, and mood). As the criteria of efficiency of conducted therapy the dynamics of tolerance and extent of recovery period at kinetic influence were assessed as well as alteration of indexes' evidence of sensory-motor reactions (nystagmus), HRV indexes (with usage of Biocom Wellness Scan system, developed by AWS, LLC in accordance with International Standard of European Cardiologists Association and North American Electrophysiology Association) and WBAM data. The safety criteria were character, evidence and terms of emergence of probable adverse events (AE) in the treatment period connected with medication intake; influence of studied drugs for indexes which characterize the function of central nervous system (CNS) (reaction on moving object (RMO)), the time of simple motor reaction (TSMR); the dynamics of physical and functional factors (heart rate (HR), systolic and diastolic blood pressure (SBP, DBP), Stange's test; exercise tolerance (index of Harvard step-test). Safety was assessed after single dose administration and after 7-day course administration of the combination ULD anti-S-100 and ULD anti-eNOS.

All the subjects during 1 month before being involved into the study had not taken any drugs. After screening the subjects were randomized into 4 groups (Group1—ULD anti-S100+anti-eNOS, Group 2—ULD anti-S100, Group 3—ULD anti-eNOS, and Group 4—placebo).

On the first day of the study (Visit 1) the initial functional and psycho-physiological state of the subjects was registered, the subjects were then given 5 tablets of the respective ULD antibodies, followed by administration of the CCEAC test. The duration of the test was registered; vegetative-vestibular disorders and AEs related to motion sickness were detected with the help of a complex diagnostic examination. In the next 2-6 days the subject were given 1 tablet three times a day of the prescribed drug. At the 7$^{th}$ day (Visit 2) the subjects were given the same dosage as on the first day (Visit 1). The complex of diagnostic studies was conducted before and after the CCEAC test. The study was organized in such way as study crew would work only with one subject. The study was parallel and conducted in the first half of a day with participation of, as a rule, 4 persons in a day, one person for drug or placebo. The next three weeks were washout period, at the end of which the new drug or placebo was prescribed to subjects of each group; the cycle of study was being repeated (Visit 1, the course intake of a drug; Visit 2). Thus, during the study each subject took part in four cycles of study. That is, each subject participated in each group with a three-week washout period between each cycle. This allowed the researcher to level the influence of individual peculiarities of a test person on the treatment effect. The analysis of drug efficiency was conducted on the data of all the test subjects who has completed the full course of studied drug intake according to study protocol (n=15).

The evidence factors of symptoms of motion sickness (vertigo, nausea, inactivity, skin pallor, sweatiness, etc.) after kinetic influence (CCEAC) against the background of single-day intake of studied drugs evidenced that all the study subjects have gained roughly the same state of motion sickness as far as the evidence of assessed symptoms of vegetative dysfunction on Halle's scale by physician-researcher was not differed significantly in all groups (Table 7, Visit 1). However, while the kinetic affect which cause similar symptoms of motion sickness was different in four groups and was dependent on the drug which was taken by the subjects of the study (Table 8, Visit 1). One-day intake of ULD anti-S100+anti-eNOS preparation led to most clearly anti motion sickness effect which manifested itself not only in significantly more time of tolerance of CCEAC test (104.10±13.14 sec. vs. 68.50±6.57 sec.—in the group of ULD anti-S100; 75.00±6.79 sec.—in the group of ULD anti-eNOS and 61.30±3.15 sec.—in the placebo group) but also in the least time of nystagmus (9.90±1.20 sec. vs. 13.50±1.51; 16.10±1.68 and 13.30±1.12 sec., respectively) and in maximal rapid recovery (96.90±13.54 sec. vs. 194.20±18.45; 202.50±21.72 and 241.70±38.41 sec., respectively).

Roughly similar indexes were registered at Visit 2 after receiving a course of drugs. To achieve the similar symptoms of motion sickness (Table 7, Visit 2) the longest time of kinetic impact was applied to the subjects who has been receiving the composition of ULD anti-S100+anti-eNOS (Table 8, Visit 2) for 7 days. The most pronounced anti motion sickness effect of the composition of ULD anti-S100+anti-eNOS was expressed in significantly less time of nystagmus (9.50±1.38 sec, p<0.01) and duration of the recovery period (117.90±15.65 sec; p<0.01). The monocomponent preparation ULD anti-S100 had anti motion sickness action as better indexes of tolerance of CCEAC test, recovery time of nystagmus and recovery than in the placebo group evidenced (Table 8, Visits 1 and 2), but the efficacy of ULD anti-S100 was inferior to composition of ULD anti-S100+anti-eNOS. The monocomponent preparation ULD anti-eNOS did not show anti motion sickness effect since the results of CCEAC tests and subsequent recovery period had no significant difference from the placebo group (Table 8, Visits 1 and 2). Comparative analysis of indexes of CCEAC test in the groups of ULD anti-S100+anti-eNOS and ULD anti-S100 in one-day intake of the drugs has shown that the addition of ULD anti-eNOS increased the tolerance of the kinetic effect on the 52%, reduced the nystagmus time on 27% and contributed to the reduction the recovery period after the end of the kinetic effect on 50% including the duration of dizziness—on 49%. However, the greatest contribution of the component of ULD anti-eNOS introduced the effectiveness of combined preparation (compositions of ULD anti-S100+anti-eNOS) in course intake of a drug which was expressed in excess of 30% of the result achieved in the group of ULD anti-S100 by factors of tolerance of kinetic effect and nystagmus duration (in each of the parameters). In addition, the growth of the effect on Visit 2 by indexes of tolerance of CCEAC test and duration of the nystagmus in relation to data of Visit 1 when taking the composition ULD anti-S100+anti-eNOS in comparison to monocomponent preparation ULD anti-S100 was expressed in a greater degree as confirmed by alteration of these indexes on 30% and 4% (versus 21% and 0% in the ULD anti-S100 group). In assessing the effectiveness of anti motion sickness properties of drugs the special attention was paid to the possible impact of drugs on the stability of autonomic nervous system (ANS) in particular, shifting of the balance between its sympathetic and parasympathetic divisions. For this purpose, at each visit HRV parameters were analyzed at the rest condition and when performing the functional tests (breathing and orthostatic tests).

TABLE 7

Indexes of Halle's scale depending on applied preparation after the performance of CCEAC test

| | Halle's scale (points) | |
| --- | --- | --- |
| Preparation | Visit 1 (one-day intake) (n = 15; M ± SE) | Visit 2 (course intake) (n = 15; M ± SE) |
| ULD anti-S100 + anti-eNOS | 12.00 ± 0.63 | 12.30 ± 0.59 |
| ULD anti-S100 | 13.30 ± 0.65 | 12.30 ± 0.46 |
| ULD anti-eNOS | 13.10 ± 0.78 | 12.00 ± 0.55 |
| Placebo | 13.40 ± 0.77 | 13.30 ± 0.45 |

TABLE 8

The dynamics of indexes of CCEAC test depending on applied preparation

| Preparation | Tolerance of CCEAC test, sec. (n = 15; M ± SD) | Nystagmus time, sec. (n = 15; M ± SD) | Recovery time, sec. (n = 15; M ± SD) |
| --- | --- | --- | --- |
| | Visit 1 (one-day intake) | | |
| ULD anti-S100 + anti-eNOS | 104.10 ± 13.14 ** | 9.90 ± 1.20 * | 96.90 ± 13.54 *** |

TABLE 8-continued

The dynamics of indexes of CCEAC test depending on applied preparation

| Preparation | Tolerance of CCEAC test, sec. (n = 15; M ± SD) | Nystagmus time, sec. (n = 15; M ± SD) | Recovery time, sec. (n = 15; M ± SD) |
|---|---|---|---|
| ULD anti-S100 | 68.50 ± 6.57 $^x$ | 13.50 ± 1.51 | 194.20 ± 18.45 $^{xxx}$ |
| ULD anti-eNOS | 75.00 ± 6.79 | 16.10 ± 1.68 | 202.50 ± 21.72 $^{xxx}$ |
| Placebo | 61.30 ± 3.15 | 13.30 ± 1.12 | 241.70 ± 38.41 |
| P value on Kruskal-Wallis test $^1$ | 0.0182 | 0.0658 | 0.0001 |
| Visit 2 (course intake) | | | |
| ULD anti-S100 + anti-eNOS | 134.70 ± 20.24 ** | 9.50 ± 1.38 ** | 117.90 ± 15.65 ** |
| ULD anti-S100 | 82.70 ± 10.33 | 13.50 ± 1.69 | 167.50 ± 14.72 $^x$ |
| ULD anti-eNOS | 74.30 ± 9.49 $^x$ | 17.30 ± 2.40 $^{xxx}$ | 209.20 ± 21.62 $^{xx}$ |
| Placebo | 63.70 ± 3.91 | 15.00 ± 1.47 | 199.60 ± 31.19 |
| P value on Kruskal-Wallis test $^1$ | 0.0341 | 0.0244 | 0.0061 |

Notes:
$^1$ for determination of significant difference between groups the Kruskal-Wallis test was used. If the test showed a significant difference of p < 0.05 for comparison between groups against each other the Mann-Whitney test was used.
* the significant difference in comparison with placebo, p < 0.05;
** the significant difference in comparison with placebo, p < 0.01;
*** the significant difference in comparison with placebo, p < 0.001.
$^x$ the significant difference in comparison with ULD anti-S100 + anti-eNOS, p < 0.05;
$^{xx}$ the significant difference in comparison with ULD anti-S100 + anti-eNOS, p < 0.01;
$^{xxx}$ the significant difference in comparison with ULD anti-S100 + anti-eNOS, p < 0.001.

The analysis of HRV at the rest condition (in sitting position) before and after the CCEAC test (Table 9) detected that in subjects receiving study drugs had a tendency to an increased rate of SDNN indicating an increase in heart rate variability due to parasympathetic influence on heart rhythm. In response to a kinetic effect in all treatment groups the value of RMS-SD increased which characterizes the activity of the parasympathetic component of autonomic regulation. In the groups receiving the composition ULD anti-S100+anti-eNOS and ULD anti-S100 showed an increase in HF which also indicated a shift in autonomic balance toward parasympathetic link. Thus, after conducting CCEAC tests in all groups there was an increase of parasympathetic effects on heart rate.

TABLE 9

The HRV parameters of the study participants at rest before and after the kinetic action

| | Visit 1 (one-day intake) | | Visit 2 (course intake) | |
|---|---|---|---|---|
| Parameter | After the drug intake | After the CCEAC test | After the drug intake | After the CCEAC test |
| ULD anti-S100 + anti-eNOS group (M ± SD) | | | | |
| SDNN, msec. | 57.7 ± 5.51 | 68.2 ± 7.42 | 59.4 ± 5.03 | 65.6 ± 4.66 |
| RMSSD, msec. | 43.1 ± 6.77 | 51.4 ± 9.22 | 47.0 ± 6.21 | 47.6 ± 5.33 |
| TP, msec. $^2$ | 979.0 ± 186.06 | 1678.3 ± 397.11# | 1067.2 ± 167.24 | 1381.0 ± 166.30 |
| LF, msec. $^2$ | 437.5 ± 709.6 | 709.6 ± 178.72 | 391.9 ± 75.61 | 588.5 ± 87.48 |
| HF, msec. $^2$ | 171.5 ± 51.08 | 228.4 ± 76.79 | 206.5 ± 58.32 | 218.5 ± 43.96 |
| LF/HF, c.u. | 4.2 ± 0.82 | 4.9 ± 0.83 | 3.3 ± 0.83 | 4.2 ± 0.91 |
| ULD anti-S100 group (M ± SD) | | | | |
| SDNN, msec. | 60.9 ± 4.62 | 70.9 ± 5.90 | 59.1 ± 4.80 | 68.8 ± 4.87 |
| RMSSD, msec. | 44.3 ± 5.39 | 50.6 ± 6.56 | 42.4 ± 4.63 | 47.8 ± 5.57 |
| TP, msec. $^2$ | 832.2 ± 124.93* | 1342.8 ± 217.09 | 841.4 ± 149.93 | 1288.0 ± 163.52# |
| LF, msec. $^2$ | 315.2 ± 52.38* | 550.9 ± 72.44# | 313.6 ± 66.71 | 540.7 ± 87.57# |
| HF, msec. $^2$ | 151.4 ± 41.19 | 247.0 ± 69.53# | 138.3 ± 38.42 | 187.1 ± 39.80 |
| LF/HF, c.u. | 3.0 ± 0.54 | 4.0 ± 0.72 | 2.8 ± 0.53 | 4.0 ± 0.52 |
| ULD anti-eNOS group (M ± SD) | | | | |
| SDNN, msec. | 67.4 ± 7.73 | 78.6 ± 6.14 | 65.8 ± 8.68 | 69.0 ± 5.23 |
| RMSSD, msec. | 53.0 ± 8.86 | 58.4 ± 7.68 | 59.6 ± 12.45 | 52.2 ± 5.30 |
| TP, msec. $^2$ | 1307.8 ± 324.24 | 1841.1 ± 359.79# | 1232.3 ± 292.51 | 1275.4 ± 172.47 |
| LF, msec. $^2$ | 576.5 ± 167.07 | 849.9 ± 194.2# | 527.2 ± 167.07 | 562.1 ± 89.38 |
| HF, msec. $^2$ | 313.3 ± 139.90 | 285.3 ± 65.92 | 218.9 ± 74.78 | 216.3 ± 63.72 |
| LF/HF, c.u. | 3.6 ± 0.87 | 3.9 ± 0.82 | 3.7 ± 1.14 | 3.8 ± 0.58 |
| Placebo group (M ± SD) | | | | |
| SDNN, msec. | 64.6 ± 6.10 | 75.7 ± 6.42 | 61.1 ± 6.72 | 70.8 ± 6.79 |
| RMSSD, msec. | 50.9 ± 7.74 | 53.1 ± 6.62 | 44.6 ± 6.63 | 44.3 ± 5.31 |
| TP, msec. $^2$ | 1062.2 ± 150.02 | 1917.8 ± 318.96# | 898.8 ± 169.62 | 1418.5 ± 227.59# |

TABLE 9-continued

The HRV parameters of the study participants at rest before and after the kinetic action

| Parameter | Visit 1 (one-day intake) | | Visit 2 (course intake) | |
|---|---|---|---|---|
| | After the drug intake | After the CCEAC test | After the drug intake | After the CCEAC test |
| LF, msec.$^2$ | 440.6 ± 77.30 | 832.4 ± 181.15 | 334.8 ± 75.94 | 611.4 ± 113.64# |
| HF, msec.$^2$ | 253.9 ± 59.95 | 266.7 ± 61.94 | 166.0 ± 48.14 | 174.1 ± 44.96 |
| LF/HF, c.u. | 3.4 ± 0.72 | 5.0 ± 1.33 | 3.4 ± 0.93 | 4.8 ± 0.83 |

Note:
*the significant difference in comparison with the placebo, $p \leq 0.05$);
the significant difference in comparison with baseline parameters, $p \leq 0.05$.

The analysis of HRV in transition states showed that one-day intake of composition ULD anti-S100+anti-eNOS increased the reaction time (13.9±1.14; p≤0.05) and the stabilization time (24.2±1.28; p≤0.05) in comparison with the ULD anti-S100 and placebo. The same factors exceeded the value of the placebo group and after the kinetic effect which demonstrated the positive effect of the combined drug on the reactivity of the ANS (increase of tolerance to changes in body position). The smallest difference between the maximum and minimum heart rate in the breath test confirmed a better balance of the two divisions of ANS after receiving a one-day composition ULD anti-S100+anti-eNOS (25.1±2.66 beats/min, p≤0.05). By the end of week course of therapy the stabilizing effect on the balance of ANS after the CCEAC test (with orthostatic and breath test) is also noticed in the group receiving the composition ULD anti-S100+anti-eNOS (Tables 10 and 11).

TABLE 10

The HRV parameters of participants of the study at orthostatic test before and after kinetic action

| Parameter | Visit 1 (one-day intake) | | Visit 2 (course intake) | |
|---|---|---|---|---|
| | After drug intake | After CCEAC test | After drug intake | After CCEAC test |
| ULD anti-S100 + anti-eNOS (M ± SD) Group | | | | |
| Exercise reaction, c.u. | 1.30 ± 0.06 | 1.40 ± 0.04 | 1.30 ± 0.06 | 1.40 ± 0.06 |
| Reaction time, sec. | 13.9 ± 1.14*ˣ | 12.7 ± 1.24* | 11.8 ± 0.57 | 11.7 ± 1.09 |
| Stabilization time, sec. | 24.2 ± 1.28*ˣ | 21.9 ± 1.44* | 20.6 ± 0.74 | 22.4 ± 1.44*ˣ |
| ULD anti-S100 (M ± SD) Group | | | | |
| Exercise reaction, c.u. | 1.40 ± 0.04 | 1.30 ± 0.04 | 1.30 ± 0.04 | 1.30 ± 0.05 |
| Reaction time, sec. | 7.60 ± 1.05 | 10.6 ± 1.55 | 9.7 ± 1.21 | 10.0 ± 1.73 |
| Stabilization time, sec. | 15.1 ± 1.16* | 18.3 ± 1.43 | 18.0 ± 1.18 | 18.0 ± 1.80 |
| ULD anti-eNOS (M ± SD) Group | | | | |
| Exercise reaction, c.u. | 1.30 ± 0.04 | 1.30 ± 0.04 | 1.50 ± 0.12 | 1.30 ± 0.04 |
| Reaction time, sec. | 8.20 ± 0.94 | 9.10 ± 1.12 | 9.2 ± 0.77 | 8.3 ± 0.70 |
| Stabilization time, sec. | 16.5 ± 1.02 | 17.1 ± 1.33 | 19.0 ± 2.04 | 16.7 ± 0.98 |
| Placebo group (M ± SD) | | | | |
| Exercise reaction, c.u. | 1.30 ± 0.04 | 1.30 ± 0.04 | 1.40 ± 0.06 | 1.30 ± 0.06 |
| Reaction time, sec. | 9.5 ± 1.28 | 8.1 ± 0.90 | 10.4 ± 1.58 | 8.8 ± 1.09 |
| Stabilization time, sec. | 18.3 ± 0.94 | 16.8 ± 1.09 | 18.0 ± 1.37 | 16.5 ± 1.11 |

Note:
*the significant difference in comparison with placebo, $p \leq 0.05$);
ˣthe significant difference in comparison with ULD anti-S100, $p \leq 0.05$.

TABLE 11

The HRV parameters of participants of the study at breath test before and after kinetic action

| Parameter | Visit 1 (one-day intake) | | Visit 2 (course intake) | |
|---|---|---|---|---|
| | After drug intake | After CCEAC test | After drug intake | After CCEAC test |
| ULD anti-S100 + anti-eNOS (M ± SD) Group | | | | |
| Corellation max HR/min HR, c.u. | 1.5 ± 0.05* | 1.5 ± 0.06 | 1.5 ± 0.05 | 1.5 ± 0.05 |
| Difference max HR − min HR, beats/min. | 25.1 ± 2.66* | 26.5 ± 2.77 | 26.5 ± 2.37 | 24.9 ± 2.24* |

TABLE 11-continued

The HRV parameters of participants of the study at breath test before and after kinetic action

| Parameter | Visit 1 (one-day intake) | | Visit 2 (course intake) | |
|---|---|---|---|---|
| | After drug intake | After CCEAC test | After drug intake | After CCEAC test |
| ULD anti-S100 (M ± SD) Group | | | | |
| Corellation max HR/min HR, c.u. | 1.5 ± 0.06 | 1.6 ± 0.05 | 1.5 ± 0.04 | 1.6 ± 0.06 |
| Difference max HR − min HR, beats/min. | 27.7 ± 2.68 | 27.2 ± 2.40 | 25.7 ± 2.24 | 26.9 ± 2.67 |
| ULD anti-eNOS (M ± SD) Group | | | | |
| Corellation max HR/min HR, c.u. | 1.5 ± 0.05 | 1.5 ± 0.04 | 1.5 ± 0.06 | 1.6 ± 0.05 |
| Difference max HR − min HR, beats/min. | 26.7 ± 2.44 | 26.2 ± 2.04 | 27.7 ± 2.47 | 27.3 ± 2.12 |
| Placebo group (M ± SD) | | | | |
| Corellation max HR/min HR, c.u. | 1.6 ± 0.07 | 1.6 ± 0.06 | 1.5 ± 0.05 | 1.6 ± 0.05 |
| Difference max HR − min HR, beats/min. | 31.2 ± 3.06 | 28.2 ± 2.50 | 27.7 ± 2.37 | 29.2 ± 2.44 |

Note:
*the significant difference in comparison with placebo, $p \leq 0.05$

The results of self-esteem of functional state (well-being, activity, mood) of the subjects which was conducted by the participants of the study after the simulation of motion sickness (CCEAC tests) at the beginning and at the end of therapy showed that the subjects of all the groups have given 'average' points for each of the parameters (Table 12). Thus, on the background of drugs intake the CCEAC tolerance was satisfactory. The highest growth rates compared with data of the placebo group by the end of the 7$^{th}$ day of intake (more than 10%) was observed in the group of composition of ULD anti-S100+anti-eNOS.

TABLE 12

The dynamics of parameters of self-esteem of functional condition (well-being-activity-mood) of study participants

| Parameter | Visit 1 (one-day intake) | Visit 2 (course intake) |
|---|---|---|
| ULD anti-S100 + anti-eNOS (M ± SE) group | | |
| Well-being | 4.3 ± 0.26 | 4.6 ± 0.27 |
| Activity | 4.2 ± 0.20 | 4.2 ± 0.22 |
| Mood | 5.0 ± 0.16 | 5.2 ± 0.13 |
| ULD anti-S100 (M ± SE) group | | |
| Well-being | 3.7 ± 0.21 | 4.3 ± 0.22 |
| Activity | 3.6 ± 0.17 | 4.0 ± 0.19 |
| Mood | 4.5 ± 0.16 | 4.9 ± 0.19 |
| ULD anti-eNOS (M ± SE) Group | | |
| Well-being | 3.9 ± 0.25 | 4.1 ± 0.26 |
| Activity | 3.8 ± 0.25 | 3.9 ± 0.23 |
| Mood | 4.4 ± 0.19 | 4.6 ± 0.19 |
| Placebo group (M ± SE) | | |
| Well-being | 4.0 ± 0.24 | 4.0 ± 0.24 |
| Activity | 3.8 ± 0.20 | 3.7 ± 0.26 |
| Mood | 4.3 ± 0.20 | 4.7 ± 0.24 |

The safety analysis included data from all the subjects who participated in the study. During the observation period a well tolerance of studied preparations was noticed. No adverse events associated with drug administration identified. All the subjects of studied groups completed treatment in the terms established by the study protocol; there was not persons early dropped out.

According to the results of physical examination including indicators of heart rate, systolic and diastolic blood pressure and according to the Harvard step test data the subjects were not recorded as with any abnormalities during the study (Table 13). All identified changes were not beyond the normal range. In this case, subjectively all subjects reported satisfactory well-being.

TABLE 13

The dynamics of physical parameters and exercise tolerance of study participants before and after kinetic action

| Parameter | Visit 1 (one-day intake) | | Visit 2 (course intake) | |
|---|---|---|---|---|
| | After drug intake | After CCEAC test | After drug intake | After CCEAC test |
| ULD anti-S100 + anti-eNOS (M ± SE) Group | | | | |
| HR (beats/min) | 74.6 ± 3.36 | 68.4 ± 3.67 | 74.1 ± 3.10 | 67.7 ± 2.62 |
| Systolic blood pressure (mmhg.) | 123.4 ± 2.83 | 125.9 ± 4.08 | 121.8 ± 2.65 | 128.3 ± 4.25 |
| Diastolic blood pressure (mmhg.) | 74.0 ± 3.09 | 79.3 ± 2.62 | 76.2 ± 2.43 | 80.3 ± 3.30 |
| Step-test index | — | 53.6 ± 2.60 | — | 52.3 ± 2.09 |
| ULD anti-S100 (M ± SE) Group | | | | |
| HR (beats/min) | 73.5 ± 2.57 | 69.7 ± 2.78 | 72.1 ± 2.84 | 67.7 ± 2.39 |
| Systolic blood pressure (mmhg.) | 127.5 ± 2.55 | 133.5 ± 4.77 | 127.1 ± 2.55 | 129.9 ± 5.06 |
| Diastolic blood pressure (mmhg.) | 75.5 ± 2.65 | 82.6 ± 3.31 | 74.9 ± 2.41 | 82.3 ± 3.19 |
| Step-test index | — | 50.6 ± 1.71 | — | 53.0 ± 1.63 |
| ULD anti-eNOS (M ± SE) Group | | | | |
| HR (beats/min) | 76.5 ± 2.59 | 67.3 ± 1.98 | 77.3 ± 2.02 | 70.1 ± 3.23 |
| Systolic blood pressure (mmhg.) | 127.3 ± 3.14 | 131.5 ± 5.16 | 123.5 ± 3.06 | 129.3 ± 4.13 |

TABLE 13-continued

The dynamics of physical parameters and exercise tolerance
of study participants before and after kinetic action

| Parameter | Visit 1 (one-day intake) | | Visit 2 (course intake) | |
|---|---|---|---|---|
| | After drug intake | After CCEAC test | After drug intake | After CCEAC test |
| Diastolic blood pressure (mmhg.) | 75.2 ± 2.24 | 80.3 ± 2.66 | 73.9 ± 2.83 | 81.0 ± 3.22 |
| Step-test index | — | 51.8 ± 2.12 | — | 51.2 ± 2.21 |
| Placebo group (M ± SE) | | | | |
| HR (beats/min) | 74.5 ± 2.78 | 68.9 ± 3.46 | 73.9 ± 3.23 | 72.3 ± 3.58 |
| Systolic blood pressure (mmhg.) | 125.3 ± 3.30 | 133.3 ± 4.73 | 124.3 ± 2.83 | 126.9 ± 3.95 |
| Diastolic blood pressure (mmhg.) | 76.2 ± 2.15 | 81.7 ± 2.83 | 75.4 ± 1.86 | 79.7 ± 3.03 |
| Step-test index | — | 50.0 ± 2.03 | — | 50.1 ± 1.99 |

In addition to the hemodynamic parameters, for evaluation of the safety of studied drugs and its possible negative impact on the central nervous functions, the following physiological parameters were examined in subjects: (RMO (reaction on moving object), SMRT (simple motor reaction time), RA (range of attention), attention span (AS), and attention stability factor (ASF)). In addition, the Stange's test was conducted to assess tolerance to hypoxia.

According to received results (Table 9) neither one-day or course drug intake had a significant effect on the estimated parameters. Indexes of sensory motor coordination (SMRT, RMO) did not differ from the results of the placebo group before and after the CCEAC test at both visits. Study data of such complicated functions like volume and stability of attention showed that the studied drugs both before and after the CCEAC test did not change the degree of concentration and shift in attention not being different from the placebo group.

The analysis of standard exercise tests with breath holding showed a tendency to increase of the tolerance of hypoxia by the subjects (Table 14). When holding the breath the duration of Stange's test grew after taking all study drugs. However, only intake of the combination composition ULD anti-S100+ anti-eNOS showed significantly longer time in the holding of the breath after the kinetic effect (68.1±18.8 sec. at baseline and 91.7±27.4 sec. after the CCEAC test; p<0.05). The increase of tolerance of hypoxia was also noted when the Gench's test (Stange's test) (breath holding at expiration, P>0.05) was used.

TABLE 14

The dynamics of parameters of psycho-physiological state
of study participants before and after kinetic action

| Parameter | Visit 1 (one-day intake) | | Visit 2 (course intake) | |
|---|---|---|---|---|
| | After drug intake | After CCEAC test | After drug intake | After CCEAC test |
| ULD anti-S100 + anti-eNOS (M ± SE) Group | | | | |
| SMRT | 257.5 ± 8.67 | 268.9 ± 10.18 | 269.6 ± 9.75 | 279.9 ± 12.24 |
| RMO, c.u. | 50.1 ± 3.92 | 49.5 ± 4.50 | 47.3 ± 4.86 | 47.0 ± 3.54 |
| RMO, % of target hit | 3.0 ± 0.95 | 4.5 ± 1.15 | 5.3 ± 1.58 | 4.0 ± 1.11 |
| AS, sec. | 5.2 ± 0.34 | 5.2 ± 0.35 | 5.2 ± 0.41 | 5.1 ± 0.40 |
| Range of attention, sec. | 41.7 ± 2.36 | 39.9 ± 2.38 | 38.1 ± 2.17 | 37.5 ± 2.04 |
| ASF | 17.4 ± 1.66 | 17.2 ± 1.51 | 18.0 ± 1.71 | 18.8 ± 1.72 |
| Stange's test | 68.1 ± 4.85 | 91.7 ± 7.07* | 71.8 ± 6.02 | 85.5 ± 9.36 |
| Gench's test | 47.1 ± 4.03 | 50.1 ± 3.94 | 46.7 ± 3.28 | 48.1 ± 4.52 |

TABLE 14-continued

The dynamics of parameters of psycho-physiological state
of study participants before and after kinetic action

| Parameter | Visit 1 (one-day intake) | | Visit 2 (course intake) | |
|---|---|---|---|---|
| | After drug intake | After CCEAC test | After drug intake | After CCEAC test |
| ULD anti-S100 (M ± SE) Group | | | | |
| SMRT | 258.9 ± 9.95 | 282.4 ± 13.56 | 268.4 ± 1.37 | 279.1 ± 9.20 |
| RMO, c.u. | 58.1 ± 6.40 | 57.5 ± 6.34 | 55.1 ± 5.06 | 53.8 ± 5.02 |
| RMO, % of target hit | 3.7 ± 1.50 | 2.0 ± 0.82 | 2.3 ± 0.83 | 5.0 ± 1.69 |
| AS, sec. | 6.0 ± 0.40 | 6.4 ± 0.52 | 6.2 ± 0.42 | 6.0 ± 0.41 |
| Range of attention, sec. | 42.6 ± 2.68 | 42.1 ± 2.27 | 42.7 ± 2.30 | 41.9 ± 2.52 |
| ASF | 14.5 ± 1.16 | 14.9 ± 1.26 | 15.3 ± 1.13 | 15.4 ± 1.18 |
| Stange's test | 59.0 ± 4.09 | 72.6 ± 6.19 | 64.5 ± 4.93 | 75.9 ± 5.67 |
| Gench's test | 47.1 ± 4.48 | 49.4 ± 4.69 | 48.3 ± 4.30 | 48.8 ± 4.14 |
| ULD anti-eNOS (M ± SE) group | | | | |
| SMRT | 257.7 ± 8.49 | 279.4 ± 14.23 | 266.7 ± 13.19 | 275.5 ± 11.44 |
| RMO, c.u. | 48.3 ± 3.67 | 51.9 ± 4.39 | 52.5 ± 4.79 | 49.6 ± 4.22 |
| RMO, % of target hit | 2.3 ± 0.83 | 2.0 ± 0.82 | 3.3 ± 1.26 | 5.7 ± 1.68 |
| AS, sec. | 5.9 ± 0.25 | 6.0 ± 0.34 | 5.5 ± 0.24 | 5.9 ± 0.33 |
| Range of attention, sec. | 41.9 ± 2.10 | 43.8 ± 2.39 | 41.3 ± 2.00 | 42.5 ± 2.22 |
| ASF | 13.7 ± 1.34 | 14.8 ± 1.31 | 15.6 ± 1.24 | 14.1 ± 1.40 |
| Stange's test | 62.5 ± 5.49 | 69.5 ± 5.09 | 56.7 ± 3.34 | 73.1 ± 7.98 |
| Gench's test | 43.1 ± 3.51 | 45.7 ± 3.15 | 43.4 ± 3.77 | 45.8 ± 4.03 |
| Placebo group (M ± SE) | | | | |
| SMRT | 267.6 ± 7.64 | 290.1 ± 11.33 | 281.1 ± 9.78 | 263.3 ± 6.85 |
| RMO, c.u. | 60.7 ± 8.31 | 54.1 ± 5.57 | 51.1 ± 3.69 | 52.6 ± 5.38 |
| RMO, % of target hit | 3.7 ± 1.03 | 3.7 ± 1.24 | 3.3 ± 0.93 | 4.3 ± 1.61 |
| AS, sec. | 6.1 ± 0.71 | 5.7 ± 0.36 | 5.5 ± 0.32 | 5.9 ± 0.71 |
| Range of attention, sec. | 41.9 ± 2.09 | 42.4 ± 2.81 | 41.3 ± 2.18 | 39.6 ± 2.26 |
| ASF | 14.5 ± 1.64 | 14.5 ± 1.79 | 15.3 ± 1.55 | 15.9 ± 1.58 |
| Stange's test | 63.7 ± 4.71 | 67.9 ± 6.90 | 64.8 ± 5.94 | 83.0 ± 12.24 |
| Gench's test | 44.7 ± 2.52 | 47.1 ± 3.30 | 43.7 ± 2.71 | 47.8 ± 3.78 |

Thus, the study using an experimental motion sickness demonstrated the effectiveness of the combination composition ULD anti-S100+anti-eNOS and monocomponent preparation ULD-S100. The studied drugs increase the stability of the subjects to the kinetic effect after simulation of the clinical and physiological effects of motion sickness contributing to more mild clinical process of motion sickness and earlier recovery of the subjects after cessation of treatment. In addition, it was shown that the anti motion sickness effect of the combination composition (compositions ULD anti-S100+ anti-eNOS) increases the efficiency of individual components. The effectiveness of the combination composition ULD anti-S100+anti-eNOS in the control of the vestibular-autonomic and sensory reactions of a body in experimental motion sickness increases at course intake. It should be noted that ULD anti-eNOS in the form of monopreparation does not have a protective effect against motion sickness but when combined with ULD anti-S100 significantly enhances the anti motion sickness effect of the last one which manifests itself as at one-day so at short course intake of the drug. The best ability to adjust the transient processes that is to influence to the reactivity of the parasympathetic and sympathetic parts of ANS as well as adaptive capabilities of ANS in a state of motion sickness (to increase the tolerance to sudden changes in a body position) was observed in the composition ULD anti-S100+anti-eNOS which is an important component of anti motion sickness properties of the drug. Composition ULD anti-S100+anti-eNOS and monocomponent preparation ULD anti-S100 when using them as anti motion sickness preparation including when performing an operator functions are safe and do not adversely impact on the physical and psycho-physiological parameters.

Combination composition ULD anti-S100+anti-eNOS and ULD anti-S100 can be recommended for the prophylaxis and relief of kinesia in motion disease (including sea, air and car sicknesses) to persons with low and moderate degree of stability. The combination composition has high safety and no adverse effects on the quality of professional activity.

Example 9

To study the properties of the combination pharmaceutical composition of the present application for the treatment of psychoorganic syndrome, tablets with weight of 300 mg were used. The tablets were impregnated with pharmaceutical composition containing water-alcohol solutions (6 mg/tab.) of activated-potentiated forms of polyclonal affinity purified rabbit brain-specific proteins antibodies S-100 (anti-S100) and to endothelial NO-synthase (anti-eNOS) in ultra low doses (ULD) obtained by super dilution of initial solution (with concentration of 2.5 mg/ml) in $100^{12}$, $100^{30}$, $100^{200}$ times, of equivalent mixture of centesimal homeopathic dilutions C12, C30, C200 ("ULD anti-S100+anti-eNOS").

The control group patients received 300 mg tablets impregnated with pharmaceutical composition containing water-alcohol solutions (6 mg/tablet) of activated-potentiated forms of polyclonal affinity purified rabbit brain-specific proteins antibodies S-100 (anti-S100) in ultra low doses (ULD) obtained by super dilution of initial solution (with concentration of 2.5 mg/ml) in $100^{12}$, $100^{30}$, $100^{200}$ times.

The study included patients diagnosed with psychoorganic syndrome of posttraumatic origin. Psychoorganic syndrome is characterized by the following triad of signs: weakness of memory, loop of intelligence, incontinence of affect (Walther Buel triad).

The study was an open-label randomized comparative parallel group clinical trial of efficacy and safety of the therapy in patients with psychoorganic syndrome of posttraumatic origin (the first group of patients took the preparation of ULD anti-S100, the second group of patients—the preparation of ULD anti-S100+anti-eNOS).

The study included 6 patients aged 35 to 90 years old (mean age 70.83±21.95) diagnosed with psychoorganic syndrome. Compliance of Patients to Following Inclusion and Exclusion Criteria was Checked:

Inclusion Criteria:
1. Patients diagnosed with posttraumatic encephalopathy with psychoorganic syndrome or with encephalopathy of complex etiology (vascular, posttraumatic) with psychoorganic syndrome, confirmed by medical history, neurological examinations and medical records.
2. Patient without change in concomitant therapy within at least one month prior to Visit 1.
3. No need for change in concomitant therapy for the whole observation period.
4. No need for immunomodulatory drugs prescription for the next 6 months.
5. Patients with a level of education sufficient to adequately communicate with the researcher and study coordinator.
6. Patients assessed by the researcher as reliable and ready to perform all scheduled clinical visits, tests and procedures stipulated in the protocol.
7. Patients having a valid home address.

Exclusion Criteria:
1. Any brain surgery in medical history.
2. Acute myocardial infarction.
3. Hemorrhagic stroke.
4. The diagnosis of psychosis, bipolar disorder or schizoaffective disorder in medical history.
5. Major depressive disorder according to criteria of depression module of international neuropsychiatric mini-interview (MINI).
6. Factors/conditions of medical or another character which in the opinion of the researcher may affect to the test results for patients in the study.
7. Answers "2A", "2B", "2C" or "3" in the section "I" of Beck Depression questionnaire (active suicidal ideation with some intent to act, without a specific plan, or active suicidal ideation with a specific plan and intent).
8. Autoimmune disease in medical history.
9. Acute damage of liver or severe cirrhosis (class C by Child-Pugh).
10. Non-corrected disorder of thyroid gland function.
11. Decompensated arterial hypertension in medical history.
12. Serious or decompensated cardiovascular disease, liver disease, kidney disease, metabolic, respiratory or hematological disease, symptomatic peripheral vascular disease or another medical or psychiatric condition which in the opinion of the researcher, may affect the patient's participation in the study or could lead to prolonged hospitalization or re-hospitalization during the study.
13. Diseases and conditions which in the opinion of researcher may prevent patient from the participation in the study.
14. The intake of the drug containing ULD anti-eNOS or the drug containig ULD anti-S100 before inclusion in the study.
15. The intake of antidepressants of any group including plant and homeopathic preparations.
16. The intake of anxiolytics of any group including plant and homeopathic preparations.
17. The intake of immunomodulators including plant and homeopathic preparations.
18. The treatment with systemic steroids within 1 month before Visit 0.
19. The participation in the study of the drug containing ULD anti-eNOS or the drug containing ULD anti-S100 if patients took at least one doze of preparation.
20. Participation in other clinical studies within 1 month before within 1 month before being enrolled in this study.

21. Pregnancy, breast feeding, impossibility to use an adequate contraception during the study period and within 1 month after the last intake of the studied drug.
22. The presence of allergy/intolerance of any component of drugs including lactose intolerance.
23. Patients taking narcotic drugs and neuroleptics, alcoholic dependence, psychiatric diseases in patients.
24. Patients are the staff of the center which directly related to the conducted study and/or are family members of the research center staff's which directly associated with the ongoing study. The "family members" are a husband (wife), parents, children, brothers (sisters).
25. Participation in the trial or presumable receiving of compensation or participation in the judicial process in the opinion of a researcher.

After the determination of patient conformity to inclusion and exclusion criteria the patients were randomized into two study groups: a group of patients receiving ULD anti-S100 (3 patients, women—33.33%, men—66.66%, mean age—71.33±16.25 years old), a group of patients receiving ULD anti-S100+anti-eNOS (3 patients, women—66.66% men—33.33%, mean age—70.33±30.66 years old).

During this study the five visits were carried out. Treatment phase lasted from Visit 1 to Visit 4 for 84±5 days on average. Visit 4 (Day 84±5) was the first endpoint of the study followed by a follow-up observation. Follow-up phase continued from Visit 4 to Visit 5 (Day 168±5 on average).

In the safety analysis the data of all patients participating in the study (n=6) was included. During the study good tolerance of the drug was recorded. No adverse events were registered. All patients of studied groups have completed the treatment according to the protocol; no early dropouts.

The effect of ULD anti-S100+anti-eNOS preparation on the main clinical signs and symptoms of psychoorganic syndrome (NPI neuropsychiatric inventory, Intensity section), on the intensity of concomitant distress of the person attending to the patient (NPI Neuropsychiatric Inventory, Distress section) as well as the on patient's cognitive functions (The Mini Mental State Examination, MMSE) were assessed. An improvement was found in the key symptoms of psychoorganic syndrome such as statistically significant reduction of the intensity section of NPI neuropsychiatric inventory (from 91.0±15.13 to 69.0±6.24, p<0.05), decrease of distress section score of NPI neuropsychiatric inventory (from 44.33±17.78 to 36.33±3.21, p<0.05) at Visit 4 (Table 15).

In the group of patients receiving ULD anti-S100 alone no clinical improvement was recorded.

At that, a difference between the groups of patients in the total score of the Intensity section of NPI neuropsychiatric inventory at the end of therapy was statistically significant at $p<0.05$.

Thus, in the conducted clinical study a positive effect of combined pharmaceutical composition ULD anti-S100+anti-eNOS on the main clinical signs and symptoms of psychoorganic syndrome and tendency to effect cognitive functions with psychoorganic syndrome. In addition, good drug tolerability was confirmed. No drug-related adverse events were registered.

Example 10

To study the properties of the combination pharmaceutical composition of the present application for the treatment of Alzheimer's disease, tablets with weight of 300 mg were used. The tablets were impregnated with pharmaceutical composition containing water-alcohol solutions (6 mg/tablet.) of activated-potentiated forms of polyclonal affinity purified rabbit brain-specific proteins antibodies S-100 (anti-S100) and to endothelial NO-synthase (anti-eNOS) in ultra low doses (ULD) obtained by super dilution of initial solution (with concentration of 2.5 mg/ml) in $100^{12}$, $100^{30}$, $100^{200}$ times, of equivalent mixture of centesimal homeopathic dilutions C12, C30, C200 (ratio: 1:1) ("ULD anti-S100+anti-eNOS").

The control group patients received 300 mg tablets impregnated with pharmaceutical composition containing water-alcohol solutions (3 mg/tablet) of activated-potentiated forms of polyclonal affinity purified rabbit brain-specific proteins antibodies S-100 (anti-S100) in ultra low doses (ULD) obtained by super dilution of initial solution (with concentration of 2.5 mg/ml) in $100^{12}$, $100^{30}$, $100^{200}$ times, of equivalent mixture of centesimal homeopathic dilutions C12, C30, C200

The study included patients diagnosed with Alzheimer's disease. Alzheimer's disease is characterized by dementia (acquired dementia, stable impairment of cognitive activity with certain loss of previously acquired knowledge and practical skills, difficulties or impossibility to gain new knowledge).

The study was an open-label randomized comparative clinical trial of efficiency and safety of the therapy in two parallel groups (preparations of ULD anti-S100 and ULD anti-S100+anti-eNOS) in the treatment of patients with mild to moderate Alzheimer's disease.

The study included 6 patients aged 55-64 years old (mean age 59.0±3.58) diagnosed with mild to moderate Alzheimer's disease.

Compliance of Patients to Following Inclusion and Exclusion Criteria was Checked:

Inclusion Criteria are as Follows:
1. Patients with mild to moderate Alzheimer's disease, confirmed by medical history, neurological examinations and medical records.

TABLE 15

|  | NPI (intensity) | NPI (distress) | ADS-ADL | MMSE |
|---|---|---|---|---|
| ULD anti-S100 + anti-eNOS before treatment | 91.0 + 15.13 | 44.33 + 17.78 | 42.66 + 4.93 | 22.33 + 3.21 |
| ULD anti-S100 + anti-eNOS after treatment | 69.0 + 6.244*# | 36.33 + 3.21* | 52.0 + 5.57 | 22.66 + 2.08 |
| ULD anti-S100 before treatment | 114.0 + 25.53 | 45.66 + 14.47 | 33.0 + 13.89 | 22.33 + 4.16 |
| ULD anti-S100 after treatment | 99.66 + 18.0 | 49.0 + 17.05 | 31.66 + 10.69 | 23.0 + 4.36 |

*p from baseline < 0.05;
p from control < 0.05

2. Patient without change in concomitant therapy within at least one month prior to Visit 1.
3. No need for change in concomitant therapy for the whole observation period.
4. No need for immunomodulatory drugs prescription for the next 6 months.
5. Patients with a level of education sufficient to adequately communicate with the researcher and study coordinator.
6. Patients assessed by the researcher as reliable and ready to perform all scheduled clinical visits, tests and procedures stipulated in the protocol.
7. Patients having a valid home address.

Exclusion Criteria are as Follows:
1. Any brain surgery in medical history.
2. Acute myocardial infarction.
3. Hemorrhagic stroke.
4. The diagnosis of psychosis, bipolar disorder or schizoaffective disorder in medical history.
5. Major depressive disorder according to criteria of depression module of international neuropsychiatric mini-interview (MINI).
6. Factors/conditions of medical or another character which in the opinion of the researcher may affect to the test results for patients in the study.
7. Answers "2A", "2B", "2C" or "3" in the section "I" of Beck Depression questionnaire (active suicidal ideation with some intent to act, without a specific plan, or active suicidal ideation with a specific plan and intent).
8. Autoimmune disease in medical history.
9. Acute damage of liver or severe cirrhosis (class C by Child-Pugh).
10. Non-corrected disorder of thyroid gland function.
11. Decompensated arterial hypertension in medical history.
12. Serious or decompensated cardiovascular disease, liver disease, kidney disease, metabolic, respiratory or hematological disease, symptomatic peripheral vascular disease or another medical or psychiatric condition which in the opinion of the researcher, may affect the patient's participation in the study or could lead to prolonged hospitalization or re-hospitalization during the study.
13. Diseases and conditions which in the opinion of researcher may prevent patient from the participation in the study.
14. The intake of the drug containing ULD anti-eNOS or the drug containig ULD anti-S100 before inclusion in the study.
15. The intake of antidepressants of any group including plant and homeopathic preparations.
16. The intake of anxiolytics of any group including plant and homeopathic preparations.
17. The intake of immunomodulators including plant and homeopathic preparations.
18. The treatment with systemic steroids within 1 month before Visit 0.
19. The participation in the study of the drug containing ULD anti-eNOS or the drug containing ULD anti-S100 if patients took at least one doze of preparation.
20. Participation in other clinical studies within 1 month before within 1 month before being enrolled in this study.
21. Pregnancy, breast feeding, impossibility to use an adequate contraception during the study period and within 1 month after the last intake of the studied drug.
22. The presence of allergy/intolerance of any component of drugs including lactose intolerance.
23. Patients taking narcotic drugs and neuroleptics, alcoholic dependence, psychiatric diseases in patients.
24. Patients are the staff of the center which directly related to the conducted study and/or are family members of the research center staffs which directly associated with the ongoing study. The "family members" are a husband (wife), parents, children, brothers (sisters).
25. Participation in the trial or presumable receiving of compensation or participation in the judicial process in the opinion of a researcher.

After the determination of patient conformity to inclusion and exclusion criteria the patients were randomized into two study groups: a group of patients receiving ULD anti-S100 (3 patients, women—100%, men—0%, mean age—59.0±3.6 years old), a group of patients receiving ULD anti-S100+anti-eNOS (3 patients, women—66.66% men—33.33%, mean age—59.0±4.36 years old).

During this study the five visits were carried out. Treatment phase lasted from Visit 1 to Visit 4 for 84±5 days on average. Visit 4 (Day 84±5) was the first endpoint of the study followed by a follow-up observation. Follow-up phase continued from Visit 4 to Visit 5 (Day 168±5 on average).

In the safety analysis the data of all patients participating in the study (n=6) was included. During the study good tolerance of the drug was recorded. No adverse events were registered. All patients of studied groups have completed the treatment according to the protocol; no early dropouts.

The effect of ULD anti-S100+anti-eNOS preparation on the main clinical signs and symptoms of Alzheimer's disease (NPI neuropsychiatric inventory, Intensity section), on the intensity of concomitant distress of the person attending to the patient (NPI Neuropsychiatric Inventory, Distress section) as well as the on patient's cognitive functions (The Mini Mental State Examination, MMSE) were assessed. An improvement was found in the key symptoms of Alzheimer's disease such as statistically significant reduction of the intensity section of NPI neuropsychiatric inventory (from 24.33±4.73 to 12.0±3.46, p<0.05) at Visit 4 (Table 16).

A tendency for reduction of distress of the person attending to the patient was also found as well as for the reduction in activity of the patient's everyday life at the end of therapy (however, without any statistically significant difference, possibly due to the small number of patients included in the study).

Besides, a tendency for improvement of cognitive functions was found, manifested by increase of MMSE score from 23.66±3.21 to 26.66±1.53 points, however, the difference also failed to reach statistically significant values at the end of therapy, which may also be related to the small sample size.

The same endpoints in the group of patients receiving ULD anti-S100, showed no trend for improvement, except a statistically insignificant improvement of MMSE score from 22.66±0.58 to 23.33±0.58 points.

At that, a difference between the groups of patients in the total MMSE score at the end of therapy was statistically significant at p<0.05.

TABLE 16

|  | NPI (intensity) | NPI (distress) | ADCS-ADL | MMSE |
| --- | --- | --- | --- | --- |
| ULD anti-S100 + anti-eNOS before treatment | 24.33 ± 4.73 | 9.66 ± 1.53 | 71.0 ± 6.56 | 23.66 ± 3.21 |

TABLE 16-continued

|  | NPI (intensity) | NPI (distress) | ADCS-ADL | MMSE |
|---|---|---|---|---|
| ULD anti-S100 + anti-eNOS after treatment | 12.0 ± 3.46* | 5.0 ± 3.61 | 74.33 ± 2.51 | 26.66 ± 1.53# |
| ULD anti-S100 before treatment | 35.66 ± 5.50 | 22.33 ± 5.50 | 61.66 ± 5.13 | 22.66 ± 0.58 |
| ULD anti-S100 after treatment | 38.33 ± 8.5 | 23.0 ± 5.0 | 61.33 ± 5.86 | 23.33 ± 0.58 |

*p from baseline < 0.05;
p from control < 0.05

Thus, in the conducted clinical study a positive effect of combined pharmaceutical composition ULD anti-S100+anti-eNOS on the main clinical signs and symptoms of Alzheimer's disease and tendency to effect cognitive functions with Alzheimer's disease. In addition, good drug tolerability was confirmed. No drug-related adverse events were registered.

Example 11

Group 1—the active drug group was given 300 mg tablets impregnated with an aqueous-alcohol solutions (6 mg/tab) of activated-potentiated form of polyclonal rabbit antibodies to brain specific S-100 protein (anti-S-100), and to endothelial NO-synthase (anti-eNOS) in ultra low dose (ULD anti-S-100+ULD anti-eNOS), purified on antigen, obtained by super dilution of initial solution (with concentration of 2.5 mg/ml) in $100^{12}$, $100^{30}$, $100^{200}$ time, equivalent to mixture of centesimal homeopathic dilutions C12, C30, C200;

Group 2—the comparison group was given 300 mg tablets impregnated with an aqueous-alcohol solution (3 mg/tab) of activated-potentiated forms of polyclonal rabbit antibodies to brain-specific S-100 protein purified on antigen in ultra low dose (ULD anti-S100) obtained by super dilution of initial solution in $100^{12}$, $100^{30}$, $100^{50}$ times, of equivalent mixture homeopathic dilutions C12, C30, C50.

Group 3—the control group (placebo) was given of 300 mg tablets having excipients (lactose monohydrate—267 mg, microcrystal cellulose—30 mg, magnesium stearate—3 mg).

The effectiveness of the active drug ULD anti-S100+anti-eNOS in the treatment of patients with syndrome of attention deficit and hyperactivity disorder (ADHD) was conducted in comparative double blind placebo-controlled study in 146 children from 6 to 12 years old (mean age 9.3±0.24 years old) who were randomized into three groups depending on prescribed therapy. Within 12 weeks the patients of group No. 1 (n=46) received the composition ULD anti-S100+anti-eNOS, 2 tablets twice a day; the comparison group 2 members (n=50) received ULD anti-S100, 2 tablets twice a day; the control group 3 members (n=50) received 2 tablets twice a day. All the patients included in the study had clinically marked presentations of ADHD which was confirmed by high points on ADHD symptoms assessing scale (ADHDRS-IV-Home Version): 33.8±0.92 in group 1; 32.5±1.14 in group 2 and 33.6±0.91 in group 3. Most of the children were characterized by a moderate degree of severity of ADHD according to the CGI-ADHD-Severity questionnaire. The total score on this scale was 4.0±0.02 points in the group 1, 4.0±0.03 points in the group 2, and 4.0±0.00 points in the group 3. Thus, initially the patients of the three groups had comparable indicators of the severity of ADHD. According to the results of neurological, clinical-laboratory and instrumental examination at the time of enrollment to the study no abnormalities in any patient was detected. Over the 12 weeks of treatment, patients were seen six times by a doctor. During which the physician-researcher recorded the dynamics of intensity of clinical presentations of ADHD (total score on a scale ADHDRS-IV-Home Version) and disease severity (on the CGI-ADHD-Severity), supervised the prescriptions and administration of treatment and evaluated the safety of the treatment.

The analysis of the effectiveness of 12 weeks of therapy in the three groups showed a decrease of more than 25% from the initial total score on a scale ADHDRS-IV-Home Version in 75% (n=36) of children treated with the composition ULD anti-S100+anti-eNOS; in 66% (n=33) of patients treated with ULD anti-S100 and in 56% (n=28) of children receiving placebo. Differences of efficiency between the groups showing a more detailed assessment, taking into account the three-level grading of improvement of condition (reduction of total score on a scale ADHDRS-IV for <25%, 25-49.9% or ≥50% from the baseline), are presented in Table 17. Significant improvement with a reduction in total score on 50% or more from the baseline was noted in 52% of children in group 9 who were taking ULD anti-S100+anti-eNOS, and in 34% of children in group 2 who were taking ULD anti-S100 (vs. 8% of patients in group 3 with placebo).

Significant reduction (p<0.001) of clinical implications of ADHD in comparison with the initial state is already occurred after 2 weeks of therapy in all three groups of observation. Positive dynamics was more significant in patients of groups 9 and 2 as the significant differences were identified in them between total scores ADHDRS-IV-Home Version, not only in relation to the screening visit but when compared with the indexes of the group 3 with placebo. In subsequent weeks of treatment the efficacy of treatment with composition ULD anti-S100+anti-eNOS and monocomponent preparation ULD-S100 started to grow, the most significantly in the active drug group (p<0.05). The resulting decrease in total score on a scale ADHDRS-IV-Home Version in children of the group 9 with ULD anti-S100+anti-eNOS was 16.5 points, in patients of the group 2 with ULD anti-S100 —12.4 points (compared to 6.3 points in the group 3 with placebo). As a result of 12-week of treatment the intensity of clinical implications of ADHD in children treated with the composition ULD anti-S100+anti-eNOS decreased by almost in half (−48.8%) and in patients treated with ULD anti-S100 more than in one-third (−38.2%) compared with the baseline.

The intake of composition ULD anti-S100+anti-eNOS or ULD anti-S100 influenced on both clusters of symptoms of ADHD which was confirmed by dynamics of assessments by two sections of the scale with ADHDRS-IV-Home Version. Moreover, the treatment with the composition ULD anti-S100+anti-eNOS was significantly higher than the effectiveness of therapy with monopreparation ULD anti-S100 in the degree of influence on the intensity of implications and attention deficit and hyperactivity/impulsivity.

The positive therapeutic effect of the active drug ULD anti-S100+anti-eNOS and drug of comparison ULD-S100 was shown in evaluating of patients' treatment results on a scale of ADHD severity assessment (CGI-ADHR-Severity) (Table 17). Almost the fourth part of the patients in ULD anti-S100+anti-eNOS group the severity of disease was decreased from moderate to mild and even to minimal as confirmed by a decrease in mean value on a scale CGI-ADHR-Severity on 15% after 3 months of therapy (from 4.0±0.02 to 3.4±0.06; p<0.001). The effect of therapy with monopreparation ULD anti-S100 was slightly lower and indicated −10% on a scale CGI-ADHR-Severity over 3 months (vs. 5% in the placebo group). The safety analysis included data of all the patients participating in the study. During the whole period of monitoring there was both, well comparable to placebo, the tolerance of active drug ULD anti-S100+anti-eNOS and preparation of comparison ULD-S100. Adverse events were reported in one patient of the group with ULD anti-S100 (subside during the fourth week of the study headaches) and in one patient of the placebo group (sleepwalking during the second month of observation). These adverse events were not connected with the therapy. In addition, during the treatment the single cases of acute respiratory disease were observed which also are not associated with the therapy. All the patients of studied groups completed the treatment to schedule established by the study protocol; no early dropouts. The absence of pathological changes according to physical examination of the patients and in the course of repeated analysis of laboratory parameters confirmed the safety of studied therapy.

According to the results of physical examination (heart rate, SBP, DBP, body temperature) in patients any pathological alterations during treatment were not registered. Differences in analyzing rates according to visits and in the compared groups did not reach the statistical significance and do not exceed the limits of physiologically-allowable deviations. High rates of adherence to therapy additionally evidenced as about effectiveness so as about the safety of studied preparations. By the end of the third month of treatment the adherence was 99.8±1.15% and 98.8±2.25% in the group 9 with ULD anti-S100+anti-eNOS and in the group 2 with ULD anti-S100 respectively (versus 74.6±2.54% in the group 3 with placebo).

Thus, the study demonstrated the efficacy and safety of the compositions ULD anti-S100+anti-eNOS and of monocomponent preparation ULD-S100 in the treatment of children with ADHD. The most pronounced therapeutic effect in the 12-week course was observed in complex drug (ULD anti-S100+anti-eNOS) which was manifested by positive dynamics of clinical symptoms in the majority (75%) of children. The composition ULD anti-S100+anti-eNOS had correcting influence to both of the clusters of symptoms of ADHD and as a result, the significant reduction of attention disorders and hyperactivity in patients with ADHD was noted.

TABLE 17

The dynamics of total score by the scale ADHDRS-IV-Home Version by the end of 12 weeks of therapy

| Groups of patients | The proportion of patients with decrease of total score by the scale ADHDRS-IV-Home Version | | |
|---|---|---|---|
| | Less than 25.0% from baseline | on 25.0 - 49.9% from baseline | on 50.0% and more from baseline |
| ULD anti-S100 + anti-eNOS, n = 48 | 12 (25%) | 11 (23%) | 25 (52%)## |
| ULD anti - S100, n = 50 | 17 (34%) | 16 (32%) | 17 (34%)## |
| Placebo, n = 50 | 22 (44%) | 24 (48%) | 4 (8%) |

The difference is significant in comparison with the placebo group:
$p < 0.01$.

TABLE 18

The dynamics of evidence of clinical implications of ADHD by the scale ADHDRS-IV-Home Version

| Treatment stage | ULD anti-S100 + anti-eNOS, n = 48 | | ULD anti-S100, n = 50 | | Placebo, n = 50 | |
|---|---|---|---|---|---|---|
| | Value (M ± SE) | Δ from baseline | Value (M ± SE) | Δ from baseline | Value (M ± SE) | Δ from baseline |
| Total score | | | | | | |
| Screening | 33.8 ± 0.96 | | 32.5 ± 1.14 | | 33.6 ± 0.91 | |
| 2 weeks | 24.1 ± 0.97***# | −28.7% | 25.1 ± 1.03***# | −22.8% | 28.8 ± 1.26*** | −14.3% |
| 4 weeks | 22.6 ± 0.98***### | −33.1% | 22.7 ± 1.23***## | −30.2% | 29.9 ± 1.06*** | −11.0% |
| 6 weeks | 19.4 ± 0.95***### | −42.6% | 20.8 ± 1.06***## | −36.0% | 29.0 ± 1.25*** | −13.7% |
| 8 weeks | 18.9 ± 0.94***### | −44.1% | 20.9 ± 1.30***### | −35.7% | 27.6 ± 1.35*** | −17.9% |
| 12 weeks | 17.3 ± 0.96***###& | −48.8% | 20.1 ± 1.21***### | −38.2% | 27.3 ± 1.48*** | −18.8% |
| Attention disorders | | | | | | |
| Screening | 18.4 ± 0.55 | | 17.4 ± 0.57 | | 18.4 ± 0.43 | |
| 2 weeks | 12.8 ± 0.57***# | −30.4% | 13.7 ± 0.68***# | −21.3% | 16.1 ± 0.66*** | −12.5% |
| 4 weeks | 11.6 ± 0.56***### | −37.0% | 12.9 ± 0.79***### | −25.9% | 16.4 ± 0.57*** | −10.9% |
| 6 weeks | 10.7 ± 0.54***### | −41.8% | 11.9 ± 0.64***## | −31.6% | 16.0 ± 0.70*** | −13.0% |
| 8 weeks | 10.3 ± 0.53***### | −44.0% | 11.5 ± 0.70***### | −33.9% | 15.1 ± 0.76*** | −17.9% |
| 12 weeks | 9.7 ± 0.55***###& | −47.3% | 11.4 ± 0.68***## | −34.5% | 14.9 ± 0.78*** | −19.0% |
| Hyperactivity/impulsion | | | | | | |
| Screening | 15.4 ± 0.61 | | 15.1 ± 0.77 | | 15.2 ± 0.62 | |
| 2 weeks | 11.3 ± 0.63*** | −26.6% | 11.4 ± 0.61*** | −24.5% | 12.7 ± 0.74*** | −16.4% |
| 4 weeks | 11.0 ± 0.62***### | −28.6% | 9.8 ± 0.64***### | −35.1% | 13.5 ± 0.67** | −11.2% |
| 6 weeks | 8.7 ± 0.59***## | −43.5% | 8.9 ± 0.64***### | −41.0% | 12.9 ± 0.73** | −15.1% |

TABLE 18-continued

The dynamics of evidence of clinical implications of ADHD by the scale ADHDRS-IV-Home Version

| Treatment stage | ULD anti-S100 + anti-eNOS, n = 48 Value (M ± SE) | Δ from baseline | ULD anti-S100, n = 50 Value (M ± SE) | Δ from baseline | Placebo, n = 50 Value (M ± SE) | Δ from baseline |
|---|---|---|---|---|---|---|
| 8 weeks | 8.6 ± 0.60***## | −44.2% | 9.5 ± 0.76***## | −37.1% | 12.5 ± 0.81*** | −17.8% |
| 12 weeks | 7.6 ± 0.57***###& | −50.6% | 8.7 ± 0.70***### | −42.4% | 12.5 ± 0.82*** | −17.8% |

Note.
The difference is significant in comparison with baseline parameter:
*$p < 0.05$,
**$p < 0.01$,
***$p < 0.001$.
The difference is significant in comparison with placebo group:
$p < 0.05$,
$p < 0.01$,
$p < 0.001$.
The difference is significant in comparison with the group of ULD anti-S100:
&$p < 0.05$.

TABLE 19

The dynamics of severity level of ADHD by the scale CGI-ADHD-Severity

| Parameter | ADHD Severity M ± SE | Δ from baseline |
|---|---|---|
| ULD anti-S100 + anti-eNOS, n = 48 | | |
| Screening | 4.0 ± 0.02 | |
| 4 Weeks | 3.6 ± 0.02** | −10% |
| 12 Weeks | 3.4 ± 0.06*** | −15% |
| ULD anti-S100, n = 50 | | |
| Screening | 4.0 ± 0.03 | |
| 4 Weeks | 3.8 ± 0.06** | −5% |
| 12 Weeks | 3.6 ± 0.08*** | −10% |
| Placebo, n = 50 | | |
| Screening | 4.0 ± 0.01 | |
| 4 Weeks | 3.9 ± 0.05 | −2.5% |
| 12 Weeks | 3.8 ± 0.06*** | −2.5% |

The difference is significant in comparison with the baseline parameter:
**$p < 0.01$,
***$p < 0.001$.

Example 12

Double blind, placebo-controlled clinical study of a combination of activated potentiated forms of antibodies to the C-terminal fragment of the angiotensin II AT1-receptor, in a mixture of homeopathic dilutions of C12, C30, C200, with activated potentiated form of antibodies to endothelial NO-synthase, in a mixture of homeopathic dilutions of C12, C30, C200, in human patients with chronic heart failure to evaluate key parameters of the CHF pathology.

80 patients (CHF of II-IV functional class (FC), left ventricular ejection fraction (LVEF) less than 40%) were divided in 4 equal treatment and control groups for a 6 months study. The background therapy was not discontinued (bisoprolol β-blocker, ACE inhibitor enalapril, aspirin (unless contraindicated); administration of diuretics, nitrates, digoxin was also admitted). Group 1 received the activated potentiated form of antibodies to a C-terminal fragment of the angiotensin II AT1-receptor (mixture of homeopathic dilutions C12, C30, C200) (3 tablets/day, n=20). Group 2 received the activated potentiated form of antibodies to endothelial NO-synthase (mixture of homeopathic dilutions C12, C30, C200) (3 tablets/day, n=20). Group 3 received the combination pharmaceutical composition comprising both activated potentiated form of antibodies to a C-terminal fragment of angiotensin II AT1-receptor (mixture of homeopathic dilutions C12, C30, C200) and activated potentiated form of antibodies to endothelial NO-synthase (mixture of homeopathic dilutions C12, C30, \ C200) (3 tablets/day, n=20). Group 4 received placebo (3 tablets/day, n=20). The groups were comparable in the initial study parameters: in age and sex, and severity (class of CHF and LVEF) and duration of the disease.

Before and after treatment, the patients were evaluated for the effect of the administered medications on vascular remodeling and endothelium dysfunction that is important for the CHF process and progression. The effects of the medications on the processes of vascular remodeling were evaluated by pulse wave velocity (PWV) ("Colson" system) in the carotid-femoral (CF) (elastic type) and carotid-radial (CR) (muscle type) segments of arteries.

Table 20 shows the dynamics in the rates of pulse wave velocity in the carotid-femoral (CF) (elastic type) and carotid-radial (CR) (muscle type) segments of arteries.

TABLE 20

| Groups/Parameters | ULDs[1] of Abs[2] to C-terminal fragment of AT1 receptor of angiotensin II | | | ULD of Abs to endothelial NO-synthase | | | Combination of ULDs of Abs to C-end fragment of AT1 receptor of angiotensine II and ULD of Abs to endothelial NO-synthase | | | Placebo | | |
|---|---|---|---|---|---|---|---|---|---|---|---|---|
| | ^ | & | Δ% | ^ | & | Δ% | ^ | & | Δ% | ^ | & | Δ% |
| CF, m/c | 9.7 ± 0.5 | 8 ± 0.6 | −14.8* | 10.1 ± 0.5 | 9.8 ± 0.4 | −2.97 | 10.8 ± 0.3 | 8.6 ± 0.6 | −20.3* | 8.2 ± 0.4 | 8.2 ± 0.5 | 0.1 |
| CR, m/c | 8.6 ± 0.2 | 8.9 ± 0.3 | 2.9 | 8.8 ± 0.1 | 8.3 ± 0.3 | −5.7 | 8.9 ± 0.5 | 7.6 ± 0.7 | −15.6*#$ | 9.1 ± 0.3 | 9.7 ± 0.3 | 6.4* |

^ denotes initial value
& denotes 6 month after beginning of administration
*denotes difference from initial value is verifiable with p value <0.05.
denotes difference from the group receiving ULDs of Abs to C-terminal fragment AT1 receptor angiotensin II with verifiable difference in p value of <0.05.
$denotes difference from the group receiving ULDs of Abs to endothelial NO-synthase with verifiable difference in p value of <0.05.
[1]ULD denotes ultra-low doses.
[2]Abs denotes antibodies.

After 6 months of treatment, only group 3 showed a proven effect of the claimed pharmaceutical composition on the stiffness of muscular type arteries. Group 1 which received ULD of antibodies to a C-terminal fragment of angiotensin II AT1-receptor, and group 3 which received the combination pharmaceutical composition of the invention showed a proven increase in the stiffness of elastic type arteries.

Example 13

Double blind, placebo-controlled clinical study of a combination of activated potentiated forms of antibodies to the C-terminal fragment of angiotensin II AT1-receptor, in a mixture of homeopathic dilutions of C12, C30, C200, with activated potentiated form of antibodies to endothelial NO-synthase, in a mixture of homeopathic dilutions of C12, C30, C200, in human patients with chronic heart failure to evaluate key measurement of quality of life.

80 patients (CHF of II-IV functional class (FC), left ventricular ejection fraction (LVEF) less than 40%) were divided in 4 equal treatment and control groups for a 6 months study. The background therapy was not discontinued (bisoprolol β-blocker, ACE inhibitor enalapril, aspirin (unless contraindicated); administration of diuretics, nitrates, digoxin was also admitted). Group 1 received the activated potentiated form of antibodies to a C-terminal fragment of angiotensin II AT1-receptor (mixture of homeopathic dilutions C12, C30, C200) (3 tablets/day, n=20). Group 2 received the activated potentiated form of antibodies to endothelial NO-synthase (mixture of homeopathic dilutions C12, C30, C200) (3 tablets/day, n=20). Group 3 received the combination pharmaceutical composition comprising both activated potentiated form of antibodies to a C-terminal fragment of angiotensin II AT1-receptor (mixture of homeopathic dilutions C12, C30, C200) and activated potentiated form of antibodies to endothelial NO-synthase (mixture of homeopathic dilutions C12, C30, \ C200) (3 tablets/day, n=20). Group 4 received placebo (3 tablets/day, n=20). The groups were comparable in the initial study parameters: in age and sex, and severity (class of CHF and LVEF) and duration of the disease. Before and after treatment, the patients were evaluated for the life quality (Minnesota and Kansas questionnaires), morphological parameters of the heart, and tolerance to physical exercise.

After 6 months of treatment, the patients in group 1 treated with ULD of antibodies to a C-terminal fragment of angiotensin II AT1-receptor showed a significant improvement of the life quality, improvement of the left ventricular systolic function, and an increased tolerance to physical exercise. Group 2 showed a proven decrease in the anxiety and depression levels and in the life quality, which were evaluated using the Kansas questionnaire. The study confirmed that the maximum therapeutic effect was achieved with the combination pharmaceutical composition of the invention in combination with the standard CHF therapy, which was administered to patients from group 3 that showed a proven positive dynamics in all parameters under study.

The combination of activated (potentiated) forms of antibodies to a C-terminal fragment of angiotensin II AT1-receptor and to endothelial nitric oxide synthase (NO-synthase) in the pharmaceutical composition of the invention (combination drug) provides an unexpected synergistic therapeutic effect implying an enhanced influence on vascular remodeling and endothelium dysfunction that is critical for the CHF process and progression, as also on the improvement of the patients' life quality, on morphological parameters of the heart and tolerance to physical exercise, which is confirmed by clinical trials.

The results are set forth in Table 21.

TABLE 21

| Groups/Parameters | ULD[1] of Abs[2] to C-terminal fragment of AT1 receptor of angiotensin II | | | ULD of Abs to endothelial NO-synthase | | |
|---|---|---|---|---|---|---|
| | ^ | & | Δ% | ^ | & | Δ% |
| Minnesota[3] | 47.5 ± 2.8 | 39.1 ± 3.8** | −17.6 | 48.1 ± 3.7 | 40.8 ± 3.8 | −15.2 |
| Kansas[4] | 82.1 ± 2.3 | 70.1 ± 5.5*** | −14.6 | 81.5 ± 2.5 | 72.0 ± 8.2* | −11.7 |
| HADS[5] | 15.3 ± 1.0 | 12.5 ± 0.9** | −18.5 | 16.2 ± 1.7 | 11.34 ± 2.1*** | −30.3 |
| FC CHF[6] | 2.7 ± 0.1 | 2.2 ± 0.1*** | −17.3 | 2.9 ± 0.1 | 2.7 ± 0.2 | −7.3 |
| FF LV[7] | 27.1 ± 0.9 | 33.6 ± 1.5** | 24.0 | 28.2 ± 1.5 | 25.3 ± 1.7 | 10.3 |
| 6-minute walk test | 378.7 ± 12.4 | 419.6 ± 13.7*** | 10.8 | 383.1 ± 15.3 | 416.8 ± 17.2 | 8.8 |

TABLE 21-continued

| Groups/<br>Parameters | Combination of ULD of Abs to C-terminal fragment of AT1 receptor of angiotensine II and ULD of Abs to endothelial NO-synthase | | | Placebo | | |
|---|---|---|---|---|---|---|
| | ^ | & | Δ% | ^ | & | Δ% |
| Minnesota[3] | 43.9 ± 2.8 | 32.0 ± 4.9***$ | −27.1 | 48.3 ± 3.7 | 42.4 ± 2.9** | −12.2 |
| Kansas[4] | 87.7 ± 2.3 | 65.7 ± 7.3***$ | −25.1 | 83.8 ± 3.5 | 60.3 ± 6.8 | −7.2 |
| HADS[5] | 16.2 ± 1.3 | 8.4 ± 0.9***#$$ | −48.1 | 17.3 ± 1.1 | 15.9 ± 1.1 | −8.1 |
| FC CHF[6] | 3.0 ± 0.2 | 1.9 ± 0.1***#$ | −36.6 | 2.7 ± 0.1 | 2.5 ± 0.1 | −6.2 |
| FF LV[7] | 25.3 ± 1.1 | 34.6 ± 1.9***#$ | 36.7 | 26.4 ± 1.1 | 28.0 ± 1.4 | 6.3 |
| 6-minute walk test | 378.7 ± 12.4 | 450.1 ± 17.7**#$ | 18.9 | 390.5 ± 11.9 | 409.1 ± 11.5 | 4.8 |

*, , *p values <0.05, 0.01 and 0.001, respectively
difference from group receiving ULDs of Abs to C-terminal fragment AT1 of angiotensin receptor II with verifiable with p value <0.05
$, $$difference from the group receiving ULDs of Abs to endothelial NO-synthase is verifiable at p values of 0.05 and 0.01, respectively.
[1]ULD means ultra low doses
[2]Abs means antibodies
[3]"Minnesota" denotes Minnesota Questionnaire
[4]"Kansas" denotes Kansas Questionnaire
[5]HADS denotes HADS total score
[6]FC CHF denotes patients with chronic heart failure, functional class
[7]FF LV denotes fraction of functioning of left vertical.

Example 14

To study properties of the proposed pharmaceutical composition in the treatment of patients with a benign prostatic hyperplasia, 300 mg pills were used, saturated with the pharmaceutical composition containing water-alcohol solutions (6 mg/pill) of activated-potentiated rabbit polyclonal affinity purified antibodies to prostate specific antigen (anti-PSA) and endothelial NO synthase (anti-eNOS) in ultra low doses (ULD), produced by ultra dilution of the initial matrix solution $100^{12}$, $100^{30}$, $100^{200}$ times, equivalent to the mixture of centesimal homeopathic dilutions C12, C30, C200 (ULD anti-PSA+anti-eNOS), and 300 mg pills, saturated with the pharmaceutical composition containing water-alcohol solutions (3 mg/pill) of activated potentiated rabbit polyclonal affinity purified antibodies to prostate specific antigen in ultra low doses (ULD), obtained by an ultra dilution of the initial matrix solution $100^{12}$, $100^{30}$, $100^{200}$ times, equivalent to the mixture of centesimal homeopathic dilutions C12, C30, C200 (ULD anti-PSA).

Benign prostatic hyperplasia (BPH) is one of the most frequently occurring disorders in males (Bruskewitz R. C., 2003; Rosen R., 2003): on the one hand, epidemiological studies, carried out in Russia, point to a gradual increase in frequency of BPH from 11.3% in 40-49 year olds to 81.4% in 80 year olds (Gorilovskiy, L. M., 1999); on the other hand, demographic studies conducted by WHO confirm a significant increase in the population over 60 years old, surpassing any other age group growth.

The main symptoms of benign prostatic hyperplasia are lower urinary tract symptoms, which can cause significant discomfort and decrease quality of life (Bruskewitz R. C., 2003; Lepor H., 2004; O'Leary M. P., 2005). In severe cases, the disease can be accompanied by complications, such as acute urinary retention, urinary tract infection, erythruria, kidney failure (Stepanov, V. N., 1999; Jacobsen S. J., 1997; Lepor H., 2004). BPH is also associated with development of erectile dysfunction in patients (Bruskewitz R. C., 2003; Daly M P, 2005).

An open-label comparative parallel group study of efficacy and safety the of pharmaceutical compositions containing ULD anti-PSA+ULD anti-eNOS and ULD anti-PSA in ameliorating urinary disturbances to caused by benign prostatic hyperplasia (BPH), included 40 patients selected in accordance with inclusions/exclusions criteria. Patients were randomized in 2 groups, one group received 1 pill 3 times per day during 12 weeks (n=21) of a ULD anti-PSA+anti-eNOS, and another one 1 pill 3 times per day during 12 weeks (n=19) of a ULD anti-PSA. The groups were comparable in age, severity of BPH symptoms, urination parameters and prostate volume.

The study included patients over 45 years old with a history of BPH with corresponding symptoms of lower urinary tract for no less than 6 months, IPSS≥13, prostate volume according to transrectal ultrasonography ≥30 cm3, with maximum urinary flow speed of ≥4 ml/s and ≤5 ml/sc and minimum residual urine volume equal to 125 ml, with PSA level ≤4 ng/ml. A necessary inclusion criterion was absence of intake of the following medications in the medical records: finasteride, dutasteride, or other experimental drug 6 months prior to inclusion in the study, α1-adrenoreceptor blockers and herbal medications 4 weeks prior to the inclusion into the study, any inhibitors of phosphodiesterase type 5 and other erectile dysfunction treatments 4 weeks prior to the inclusion into the study.

The study did not include patients undergone invasive methods of treatment of BPH, including transurethral prostatic resection, thermotherapy, transurethral needle ablation, stent angioplasty and other; with malignant oncological disease, acute urination delay, bladder stones, urethral stricture, Marion's disease, genitourinary system infections in the phase of active inflammation and others.

Clinical efficacy of pharmaceutical compositions was assessed by the improvement of clinical symptoms of lower urinary tract, evaluated using IPSS questionnaire (International Prostate Symptom Score), urination parameters (maximum and average urinary flow speed, urination volume, volume of residual urine) and prostate volume based on the data of transurethral ultrasound (TU), and also erectile function was evaluated based on the data obtained from IIEF questionnaire (International Index of Erectile Function). Results of the study are shown in tables 22 and 23.

TABLE 22

| | ULD anti-PSA | | | | ULD anti-PSA + ULD anti-eNOS | | | |
|---|---|---|---|---|---|---|---|---|
| | n/N (%)[1] | In., aver. | 12 weeks., aver. | Δ, cp | n/N (%)[1] | In., aver. | 12 weeks., aver. | Δ, cp |
| IPSS, score | 19/19 (100.0) | 17.8 | 11.9 | −5.9 | 20/21 (95.2) | 16.0 | 10.5 | −5.6 |
| QoL/, score (quality of life) | 19/19 (100.0) | 3.4 | 2.4 | −1.0 | 20/21 (95.2) | 3.4 | 2.3 | −1.1 |
| IIEF, score | 2/19 (10.5) | 17.8 | 18.6 | 0.8 | 4/21 (19.0) | 17.5 | 18.9 | 1.4 |
| Qmax, ml/s (maximum urine rate) | 16/19 (84.2) | 10.8 | 13.1 | 2.2 | 15/21 (71.4) | 11.7 | 13.7 | 2.0 |
| Qave, ml/s (average urine rate) | 15/19 (78.9) | 5.8 | 7.1 | 1.3 | 18/21 (85.7) | 5.8 | 7.1 | 1.3 |
| V, ml (volume of urination) | 10/19 (52.6) | 218.6 | 206.8 | −11.8 | 15/21 (71.4) | 203.7 | 252.0 | 48.3 |
| RV, ml (residual volume of urine) | 15-19 (78.9) | 23.6 | 19.4 | −4.3 | 14/21 (66.6) | 19.1 | 14.1 | −5.0 |
| PV, cm$^3$ (prostate volume) | 18/19 (94.7) | 55.9 | 48.9 | −7.0 | 15/21 (71.4) | 57.0 | 52.4 | −4.6 |

[1] the numerator is a number of patients (n) showing improvement, denominator is total number of patients in the study (N).

TABLE 23

Dynamics of subscales of obstructive and irritative symptoms, and question 7 of IPSS questionnaire

| | ULD anti-PSA | | ULD anti-PSA + anti-eNOS | |
|---|---|---|---|---|
| | M ± SD Visit 1 | M ± SD Visit 2 | M ± SD Visit 1 | M ± SD Visit 2 |
| Obstructive | 10.0 ± 3.02# | 6.5 ± 2.81*** | 8.2 ± 2.96 | 6.0 ± 3.39** |
| Irrit. | 7.5 ± 2.21& | 5.3 ± 1.90*** | 7.8 ± 2.16& | 4.5 ± 2.34*** |
| 7$^{th}$ question | 2.1 ± 0.78 | 1.9 ± 0.75 | 2.3 ± 0.90 | 1.4 ± 0.98*** |
| Obstr., %[2] | | −33.4 ± 26.85 | | −25.2 ± 34.50 |
| Irrit., %[2] | | −28.2 ± 1730 | | −40.3 ± 30.35 |
| 7$^{th}$ question, %[2] | | −2.0 ± 49.61## | | −37.7 ± 39.23 |

*p < 0.05 vs baseline;
**p < 0.01 vs vaseline;
***p < 0.001 vs baseline
p < 0.01 vs ULD anti-PSA
[2] shows decrease compared to the baseline in %, average group value The given data confirm that both ULD anti-PSA, and ULD anti-PSA+ULD anti-eNOS were used to effectively treat symptoms of lower urinary tract, increase average and maximum urinary flow speed, improve quality of life of patients (Table 22). The course of the was not long (12 weeks), therefore, a decrease in prostate volume was not observed in any study group. ULD anti-PSA did not effect the volume of urination, which increased only in 52.6% patients, on average the group showed some statistically insignificant decrease of urination volume by 11.8 ml (5.4%) compared to the baseline values. At the same time, patients, treated with ULD anti-PSA+ULD anti-eNOS, showed an increase in urination volume in 71.4%, and on average, an increase in volume was 48.3 ml (23.7%) compared to the baseline.

An analysis of dynamics of obstructive and irritative symptoms according to IPSS subscales as well as nucturia evidence (question 7 of IPSS) showed that both pharmaceutical compositions contributed to a decrease of obstruction and irritative symptoms, and also a decrease of nucturia symptoms. At the same time, a ULD anti-PSA+anti-eNOS was more effective compared to a ULD anti-PSA in decreasing irritative symptoms of lower urinary tract (28.2% vs. 40.3%, p<0.05) and nighttime urination urges (2.0% vs. 37.7%,).

It should be noted, that ULD anti-PSA+ULD anti-eNOS is also more effective compared to ULD anti-PSA in improving erectile function in patients. In ULD anti-PSA+ULD anti-eNOS group, the total IIEF (International Index of Erectile Dysfunction) score increased by 19% in patients (in ULD anti-PSA group by 10.5%), an average increase of IIEF score in ULD anti-PSA+ULD anti-eNOS group was 8% vs 4.5% in a ULD anti-PSA group.

The pharmaceutical compositions showed excellent safety profile, no adverse effects related to the administered medications were observed in the course of study.

Therefore, ULD anti-PSA+ULD anti-eNOS showed better efficacy compared to that of ULD anti-PSA in treating urination problems caused by benign prostatic hyperplasia. In addition, a greater positive effect of ULD anti-PSA+ULD anti-eNOS on erectile function of patients compared to ULD anti-PSA was revealed.

What is claimed is:

1. A method for administering a homeopathically potentized form of antibodies to a subject, said method comprising administering to said subject a combination comprising a homeopathically potentized form of an antibody to an endogenous biological molecule and a homeopathically potentized form of an antibody to endothelial NO-synthase.

2. A method for administering a homeopathically potentized form of antibodies to a subject, said method comprising administering a combination of a homeopathically potentized form of an antibody to an endogenous biological molecule and a homeopathically potentized form of an antibody to endothelial NO-synthase to said subject.

3. The method of claim 2, wherein said endogenous biological molecule is S-100 protein.

4. The method of claim 2, wherein said endogenous biological molecule is prostate specific antigen.

5. The method of claim 2, wherein said activated-potentiated form an antibody to an endogenous biological molecule is an antibody to insulin receptor.

6. The method of claim 2, wherein said activated-potentiated form an antibody to an endogenous biological molecule is an antibody to angiotensin receptor II.

7. The method of claim 1, wherein said endogenous biological molecule is S-100 protein.

8. The method of claim 1, wherein said endogenous biological molecule is prostate specific antigen.

* * * * *